US008053636B2

(12) United States Patent
Van Thournout et al.

(10) Patent No.: US 8,053,636 B2
(45) Date of Patent: Nov. 8, 2011

(54) STRESS TOLERANT COTTON PLANTS

(75) Inventors: Michel Van Thournout, Sint-Michiels (BE); Arlette Reynaerts, Drongen (BE); John Jacobs, Merelbeke (BE)

(73) Assignee: Bayer Bioscience N.V., Ghent (BE)

( * ) Notice: Subject to any disclaimer, the term of this patent is extended or adjusted under 35 U.S.C. 154(b) by 876 days.

(21) Appl. No.: 11/666,465

(22) PCT Filed: Oct. 27, 2005

(86) PCT No.: PCT/EP2005/011657
§ 371 (c)(1),
(2), (4) Date: Apr. 27, 2007

(87) PCT Pub. No.: WO2006/045633
PCT Pub. Date: May 4, 2006

(65) Prior Publication Data
US 2009/0013431 A1    Jan. 8, 2009

Related U.S. Application Data

(60) Provisional application No. 60/628,597, filed on Nov. 17, 2004.

(30) Foreign Application Priority Data

Oct. 29, 2004    (EP) ................................... 04077984

(51) Int. Cl.
*A01H 1/00*    (2006.01)
*C12N 15/82*    (2006.01)
*C12N 15/87*    (2006.01)
(52) U.S. Cl. ........................ 800/285; 800/314; 800/278
(58) Field of Classification Search .................. None
See application file for complete search history.

(56) References Cited

U.S. PATENT DOCUMENTS

| 5,004,863 | A | 4/1991 | Umbeck |
| 5,510,471 | A | 4/1996 | Lebrun et al. |
| 6,483,013 | B1 | 11/2002 | Reynaerts et al. |
| 6,566,587 | B1 | 5/2003 | Lebrun et al. |
| 6,693,185 | B2 * | 2/2004 | Babiychuk et al. ......... 536/23.6 |
| 2009/0064371 | A1 * | 3/2009 | Metzlaff et al. .............. 800/278 |

FOREIGN PATENT DOCUMENTS

| EP | 04077624.7 | 9/2004 |
| WO | WO 92/15675 | 9/1992 |
| WO | WO 99/37789 | 7/1999 |
| WO | WO 00/04173 | 1/2000 |
| WO | WO 02/066972 | 8/2002 |
| WO | WO 03/076619 | 9/2003 |

OTHER PUBLICATIONS

Klahre et al., PNAS, 2002, vol. 99, pp. 11981-11986.*
Thomas et al., Plant J., 2001, vol. 25, pp. 417-425.*
Alvarez-Gonzalez, et al., "Poly(ADP-ribose) Catabolism in Mammalian Cells exposed to DNA-damaging agents", Mutation Research, vol. 218, p. 67-74, 1989.
Amor, et al., "The involvement of Poly(ADP-ribose) Polymerase in the Oxidative Stress responses in Plants", FEBS Letters, vol. 440, p. 1-7, 1998.
Babiychuk, et al., "Efficient Gene tagging in *Arabidopsis thaliana* using a gene trap approach", Proc. Natl. Acad. Sci. USA, vol. 94, p. 12722-12727, Nov. 1997.
Babiychuk, et al., "Higher Plants Possess two structurally different Poly(ADP-ribose) Polymerases", The Plant Journal, vol. 15, No. 5, p. 635-645, 1998.
Baulcombe, "RNA Silencing in Plants", Nature, vol. 431, p. 356-363, Sep. 16, 2004.
Chen, et al., "Poly(ADP-ribose) Polymerase in Plant Nuclei", Eur. J. Biochem., vol. 224, p. 135-142, Aug. 1994.
Cornelissen, et al., "Nuclear Transcriptional Activity of the Tobacco Plastid *psbA* Promoter", Nucleic Acids Research, vol. 17, No. 1, 1989.
De Block, et al., "Poly(ADP-ribose) polymerase in plants affects energy homeostasis, cell death and stress tolerance", The Plant Journal, vol. 41, p. 95-106, 2005.
De Greve, et al., "Nucleotide Sequence and Transcript Map of the *Agrobacterium tumefaciens* Ti Plasmid-Encoded Octopine Synthase Gene", Journal of Molecular and Applied Genetics, No. 6, p. 499-511, 1982.
de Murcia, et al., "Poly(ADP-ribose) polymerase: a molecular nick-sensor", TIBS, vol. 19, p. 172-176, Apr. 1994.
Duesterhaus, et al., "Development of a Laboratory Screening Test for the Evaluation of Cold Tolerance in Cotton Seed Germination", Proceedings of the Beltwide Cotton Conference, vol. 1, p. 621-623, 1999.
Duesterhaus, et al., "A screening test for the evaluation of cold tolerance in Cottonseed Germination and emergence", Proceedings of the Beltwide Cotton Conference, vol. 1, p. 596-599, 2000.
Ikejima, et al., "The Zinc fingers of Human Poly(ADP-ribose) Polymerase are Differntially Required for the Recognition of DNA Breaks and Nicks and the Consequent Enzyme Activation", The Journal of Biological Chemistry, vol. 265, No. 35, p. 21907-21913, Dec. 15, 1990.
Jones, et al., "High Level expression of introduced Chimaeric genes in regenerated transformed plants", The EMBO Journal, vol. 4, No. 10, p. 2411-2418, 1985.
Kameshita, et al., Poly(ADP-Ribose) Synthetase: Separation and Identification of Three Proteolytic Fragments as the Substrate-Binding Domain, The DNA-Binding Domain, and the Automodification Domain, The Journal of Biological Chemistry, vol. 259, No. 8, p. 4770-4776, Apr. 25, 1984.
Lepiniec, et al., "Characterization of an *Arabidopsis thaliana* cDNA homologue to animal Poly(ADP-ribose) Polymerase", FEBS Letters, vol. 364, p. 103-108, 1995.
Lindahl, et al., "Post-translational modification of Poly(ADP-ribiose) Polymerase induced by DNA Strand breaks", TIBS, vol. 20, p. 405-411, Oct. 1995.
Mahajan, et al., "Purification and cDNA Cloning of Maize Poly(ADP)-Ribose Polymerase", Plant Physiol., vol. 118, p. 895-905, 1998.

(Continued)

*Primary Examiner* — Li Zheng
(74) *Attorney, Agent, or Firm* — Hunton & Williams LLP

(57) ABSTRACT

The invention relates to the use of cotton parp2 gene or cDNA sequences to obtain stress tolerant cotton plants. Various cotton parp2 sequences are also provided.

33 Claims, 4 Drawing Sheets

OTHER PUBLICATIONS

Needleman, et al., "A General Method Applicable to the Search for Similarities in the Amino Acid Sequence of Two Proteins", J. Mol. Biol., vol. 48, p. 443-453, 1970.

O'Farrell, "ADP-ribosylation reaction in plants", Biochimie, vol. 77, p. 486-491, 1995.

Odell, et al., "Identification of DNA sequences required for activity of the cauliflower mosiac virus 35S promoter", Nature, vol. 313, p. 810-812, Feb. 28, 1985.

Payne, et al., "Cytological detection of poly (ADP-ribose) polymerase", Exp. Cell Res., vol. 99, p. 428-432, 1976.

Rosche, et al., Genomic Structure and Expression of the pyruvate, orthophosphate dikinase gene of the dicotyledonous $C_4$ plant *Flaveria trinervia* (Asteraceae), Plant Molecular Biology, vol. 29, p. 663-678, 1995.

Schulze, et al., "Laboratory Tests used to screen for chilling tolerance in Cotton Genotypes", Proceedings of the Beltwide Cotton Conference, vol. 2, p. 1240-1243, 1996.

Schulze, et al., "Evaluation of Chilling Tolerance in Cotton Genotypes", Proceedings of the Beltwide Cotton Conference, vol. 2, p. 1383-1385, 1997.

Verdaguer, et al., "Isolation and Expression in Transgenic tobacco and rice plants, of the cassava vein mosaic virus (CVMV) promoter", Plant Molecular Biology, vol. 31, p. 1129-1139, 1996.

Willmitzer, et al., "Poly(ADP-ribose) Synthesis in Plants", ADP-Ribosylation Reactions (Hayashi, O. and Ueda, K., eds) New York: Academic Press, p. 241-252, 1982.

Zambryski, "Basic Processes Underlying *Agrobacterium*-Mediated DNA Transfer to Plant Cells", Annu. Rev. Genet., vol. 22, p. 1-30, 1988.

Deblock et al., "Generating Stress Tolerant Crops by Economizing Energy Consumption," Pflanzenschutz-Nachrichten Bayer, pp. 105-110 (2004).

Metzlaff, "Biotechnology in Agriculture: Shaping the Future," Slide 1-16, Science Room (2004).

* cited by examiner

```
GV1   MIKNVKIEEFGVRVIGANSCGVLKHICRRINVYPSISFLHSQTISPALCSSKNMARKLKVGQL
cDNA  ------------------------------------------------------------
GV2   ---------------------------------------------------MASKLKAGQL

GV1   RDELAQRGLDTIGTKPLLVLRLEDALLKERKKEEENGGKANNAIGNNKRKRGRESDVCNNEDS
CDNA  ------------------------------------------------------------
GV2   RDELAQRGLDTIGTKPLLVLRLEDALLKERKKEEENGGKANNAIGNNKRKRGRESDVCSNEDS

GV1   DKVNAVEEFRQMNVKQLREQATLRRLSTVGTKKELLERLCEDADKNPLPVK---EEEEEEEE
CDNA  ------------------------------------------------------------
GV2   DKVNAVEEFRQMNVKQLREQATLRGLSTVGTKKELLERLCEDADKNPLPVKVEEEEEEEEEE

GV1   EEEEKESSKEEKIVTATKKGVAVLDQGIPDDIKAHYH-----------------------
CDNA  -------------YSDEEGVAVLDQGIPDDIKAHYHVLQK--------------------
GV2   EEEEKESRKEEKIVTATKKGVAVLDQGIPDEIKAHYHVLQKASLCCLNSIFEPVILKNILPAC

GV1   ----------------------GDDIYDAMLNQTNVGQNNNKFFVIQLLESDDSKTYMVHNRW
CDNA  ----------------------GDDIYDAMLNQTNVGQNNNKFFVIQLLESDDSKTYMVHNRW
GV2   FILCYNIHLQNRRINILSSVIQGDHIYDAMLNQTNVGQNNNKFFVIQLLESDDSKTYMVHNRW

GV1   GRVGVKGQIKLHGPFTSRQAAIDEFQTKFFNKTKNYWYNRKDFVCHPKCYTLLEMDYDEKEKE
CDNA  GRVGVKGQIKLHGPFTSRQAAIDEFQTKFFNKTKNYWYNRKDFVCHPKCYTLLEMDYDEKEKE
GV2   GRVGVKGQIKLHGPFTSRQAAIDVFQTKFFNKTKNYWYNRKDFVCHPKCYTLLEMDYDEKEKD

GV1   SDVKRKANSSIGAQLRETKLEQRVAKFISIICNISMMKQQMMEIGYNADKLPLGKLSKSTILK
CDNA  SDVKRKANSSIGAQLRETKLEQRVAKFISIICNISMMKQQMMEIGYNADKLPLGKLSKSTILK
GV2   SDVKRKANSSIGAQLRETKLEQRVAKFISVICNISMMKQQMMEIGYNADKLPLGKLSKSTILK

GV1   GYDVLKKIADVIDQSNRSKLEQLSSEFYTVIPHDFGFRKMRESSSSSPPLTIPNNNITTDTEL
CDNA  GYDVLKKIADVIDQSNRSKLEQLSSEFYTVIPHDFGFRKMR--------------------
GV2   GYDILKKIADVIDQSNRSKLEQLSSEFYTVIPHDFGFRKMRESSSSSPPLTIPNNNITTDAEL

GV1   YVAGDFVIDTPQKLKKKLEMVEALGEIEVASKLLMDDITMEEDPLYYRYQQLHCELFPLDNDT
CDNA  ----DFVIDTPQKLKKKLEMVEALGEIEVASKLLMDDITMEEDPLYYRYQQLHCELFPLDNDT
GV2   YVAGDFVIDKPQKLKKKLEMVEALGEIEVASKLLMDDITMEEDPLYYRYQQLHCELFPLDNDT

GV1   EEFAMIVKYIQNTHAQTHSNYTVDVVQIFAVRRDGESERFKKFSGTKNRMLLWHGSRLTNWTG
CDNA  EEFALIVKYIQNTHAQTHSNYTVDVVQIFKVTRDGESERFKKFSGTKNRMLLWHGSRLTNWTG
GV2   EEFALIVKYIQNTHAQTHSNYTVDVVQIFKVTRDGESERFKKFSGTKNRMLLWHGSRLTNWTG

GV1   ILSQGLRIAPPEAPATGYMFGKGVYFADMFSKSANYCYTNSAFTTGVLLLCEVVLQSVQMIFL
cDNA  ILSQGLRIAPPEAPATGYMFGKGVYFADMFSKSANYCYTNSAFTTGVLLLCE----------
GV2   ILSQGLRIAPPEAPATGYMFGKGVYFADMFSKSANYCYTNSAFTTGVLLLCE----------

GV1   VALGDMAELLQAKSDADKLPDGKLSTKGVGATALDPSEAQSLDDGVVVPLGKPKEQKRKGALL
cDNA  VALGDMAELLQ-KSDADKLPDGKLSTKGVGATAPDPSEAQSLDDGVVV--------------
GV2   VALGDMAELLQAKSDADKLPDGKLSTKGVGATAPDPSEAQSLDDGVVVPLGKPKEQNRKGALL

GV1   YNEYVVYNVDQIRMRYLIQVSFKYTK
cDNA  --------------------------
GV2   YNEYIVYNVDQIRMRYLIQVSFKYTK
```

Fig. 4

SEQUENCE LISTING

```
<160> NUMBER OF SEQ ID NOS: 26

<210> SEQ ID NO 1
<211> LENGTH: 25
<212> TYPE: DNA
<213> ORGANISM: Artificial Sequence
<220> FEATURE:
<223> OTHER INFORMATION: Oligonucleotide P1a
<220> FEATURE:
<221> NAME/KEY: variation
<222> LOCATION: (4)..(4)
<223> OTHER INFORMATION: t OR c
<220> FEATURE:
<221> NAME/KEY: variation
<222> LOCATION: (11)..(11)
<223> OTHER INFORMATION: g OR t

<400> SEQUENCE: 1
ggtygccaag kggaacaaca acacc                                         25

<210> SEQ ID NO 2
<211> LENGTH: 29
<212> TYPE: DNA
<213> ORGANISM: Artificial Sequence
<220> FEATURE:
<223> OTHER INFORMATION: Oligonucleotide P1b
<220> FEATURE:
<221> NAME/KEY: variation
<222> LOCATION: (10)..(10)
<223> OTHER INFORMATION: a OR g OR t
<220> FEATURE:
<221> NAME/KEY: variation
<222> LOCATION: (13)..(13)
<223> OTHER INFORMATION: g OR a
<220> FEATURE:
<221> NAME/KEY: variation
<222> LOCATION: (17)..(17)
<223> OTHER INFORMATION: g OR t
```

```
<220> FEATURE:
<221> NAME/KEY: variation
<222> LOCATION: (18)..(18)
<223> OTHER INFORMATION: a OR c
<220> FEATURE:
<221> NAME/KEY: variation
<222> LOCATION: (21)..(21)
<223> OTHER INFORMATION: g OR a
<220> FEATURE:
<221> NAME/KEY: variation
<222> LOCATION: (22)..(22)
<223> OTHER INFORMATION: a OR c
<220> FEATURE:
<221> NAME/KEY: variation
<222> LOCATION: (26)..(26)
<223> OTHER INFORMATION: a OR c

<400> SEQUENCE: 2
ggatgatccd ttrtatkmtc rmtacmagc                                29

<210> SEQ ID NO 3
<211> LENGTH: 29
<212> TYPE: DNA
<213> ORGANISM: Artificial Sequence
<220> FEATURE:
<223> OTHER INFORMATION: Oligonucleotide P1c
<220> FEATURE:
<221> NAME/KEY: variation
<222> LOCATION: (6)..(6)
<223> OTHER INFORMATION: g OR a
<220> FEATURE:
<221> NAME/KEY: variation
<222> LOCATION: (9)..(9)
<223> OTHER INFORMATION: g OR c OR t
<220> FEATURE:
<221> NAME/KEY: variation
<222> LOCATION: (12)..(12)
<223> OTHER INFORMATION: a OR t
<220> FEATURE:
<221> NAME/KEY: variation
<222> LOCATION: (15)..(15)
<223> OTHER INFORMATION: a OR c OR t
<220> FEATURE:
<221> NAME/KEY: variation
<222> LOCATION: (18)..(18)
<223> OTHER INFORMATION: g OR c
<220> FEATURE:
<221> NAME/KEY: variation
<222> LOCATION: (21)..(21)
<223> OTHER INFORMATION: g OR a
<220> FEATURE:
<221> NAME/KEY: variation
<222> LOCATION: (23)..(23)
<223> OTHER INFORMATION: g OR a
<220> FEATURE:
<221> NAME/KEY: variation
<222> LOCATION: (27)..(27)
<223> OTHER INFORMATION: g OR a

<400> SEQUENCE: 3
gagaaratbg twachgcsac rargaargg                                29

<210> SEQ ID NO 4
<211> LENGTH: 26
<212> TYPE: DNA
<213> ORGANISM: Artificial Sequence
<220> FEATURE:
<223> OTHER INFORMATION: Oligonucleotide P1x

<400> SEQUENCE: 4
caagaggaaa cagttcacag tgaagc                                   26

<210> SEQ ID NO 5
<211> LENGTH: 426
```

```
<212> TYPE: DNA
<213> ORGANISM: Artificial Sequence
<220> FEATURE:
<223> OTHER INFORMATION: Cotton parp2 cDNA 1_1

<400> SEQUENCE: 5
accagcagca tcactgtgaa ctgtttcctc ttgacaatga tactgaggag ttcgctttga     60
ttgtaaagta tattcagaat actcatgctc agacacattc aaattataca gttgatgttg    120
ttcaaatatt caaggtgaca agagacggtg aaagtgaacg ctttaaaaag ttttctggaa    180
caaaaaatag aatgctgttg tggcatggtt ctcggcttac taactggact ggcattctgt    240
cccaaggttt gcgcattgct ccacctgaag cgcctgccac gggttatatg tttgggaagg    300
gggtttactt tgctgatatg ttctccaaaa gtgcaaatta ttgctatact aattctgcct    360
tcacaacagg ggtgttgctt ctatgtgagg ttgccctggg tgacatggct gagcttctac    420
aagcta                                                              426

<210> SEQ ID NO 6
<211> LENGTH: 573
<212> TYPE: DNA
<213> ORGANISM: Artificial Sequence
<220> FEATURE:
<223> OTHER INFORMATION: cDNA cotton parp2 part 1 variant 2

<400> SEQUENCE: 6
tggatgatcc gttgtatgat caataccagc agcttcactg tgaactgttt cctcttgaca     60
atgatactga ggagttcgct ttgattgtaa agtatattca gaatactcat gctcagacac    120
attcaaatta tacagttgat gttgttcaaa tattcaaggt gacaagagac ggtgaaagtg    180
aacgctttaa aaagttttct ggaacaaaaa atagaatgct gttgtggcat ggttctcggc    240
ttactaactg gactggcatt ctgtcccaag gtttgcgcat tgctccacct gaagcgcctg    300 ccacggggtta tatgtttggg aaggggggttt actttgctga tatgttctcc aaaagtgcaa    360
attattgcta tactaattct gccttcacaa caggggtgtt gcttctatgt gaggttgccc    420
tgggtgacat ggctgagctt ctacaagcta aaagcgatgc tgataagctg ccggatggga    480
agttgagcac aaaaggtgtt ggtgcaactg caccggatcc ttctgaagcc cagtcacttg    540
atgatggtgt tgttgttccc cttggcgaat cca                                573

<210> SEQ ID NO 7
<211> LENGTH: 566
<212> TYPE: DNA
<213> ORGANISM: Artificial Sequence
<220> FEATURE:
<223> OTHER INFORMATION: cDNA cotton parp2 part 1 variant 3

<400> SEQUENCE: 7
tggatgatcc attgtattct cgctaccagc agcttcactg tgaactgttt cctcttgaca     60
atgatactga ggagttcgct ttgattgtaa agtatattca gaatactcat gctcagacac    120
attcaaatta tacagttgat gttgttcaaa tattcaaggc gacaagagac ggtgaaagtg    180
aacgctttaa aaagttttct ggaacaaaaa atagaatgct gttgtggcat ggttctcggc    240
ttactaactg gaccggcatt ctgtcccaag gtttgcgcat tgctccacct gaagcgcctg    300 ccacggggtta tatgtttggg aaggggggttt actttgctga tatgttctcc aaaagtgcaa    360
attattgcta tactaattct gccttcacaa ctgggggtgtt gcttctatgt gaggttgccc    420
tgggtgacat ggctgagctt ctacaagcta aaagcgatgc tgataagctg ccggatggga    480
agttgagcac aaaaggtgtt ggtgcaactg caccggatcc ttctgaagcc cagtcacttg    540
```

```
atgatggtgt tgttgttcca cttgga                                          566
```

<210> SEQ ID NO 8
<211> LENGTH: 881
<212> TYPE: DNA
<213> ORGANISM: Artificial Sequence
<220> FEATURE:
<223> OTHER INFORMATION: cDNA cotton parp2 part 2 variant 1

<400> SEQUENCE: 8

```
gagaagatgg ttactgcgac gaggaagggt ggctgttctg gatcaaggga tcccagatga     60
cataaaggct cattatcatg ttctacaaaa gggtgatgat atctatgatg ccatgttaaa    120
tcagacgaat gttgggcaaa acaataacaa attctttgtg atccagcttc tagaatctga    180
tgactcgaag acatacatgg ttcataacag atggggtaga gttggtgtga agggtcaaat    240
taagttacat ggcccctttta cttcacgaca agccgcaatt gatgagtttc aaaccaaatt    300
ctttaacaag accaaaaact attggtacaa cagaaaagac tttgtttgtc acccaaagtg    360
ctacaccttg ctggagatgg actatgatga aaagaaaag gaatctgatg tcaaaagaaa    420
ggctaactct tccattggtg ctcaattgcg ggagacaaag cttggacaac gtgttgctaa    480
gtttatctct attatatgca atatcagcat gatgaagcaa caaatgatgg aaataggata    540
caatgctgac aagttgcctc ttggtaagct aagcaaatcc acaattttaa aggggtatga    600
tgtcttaaag aaaattgctg atgtgattga ccagtcaaac aggagcaagc ttgagcaatt    660
aagttcggaa ttttacaccg tgattccaca tgattttgga tttagaaaaa tgcgtgattt    720
tgtcatcgac acacctcaga agttgaaaaa gaagttggaa atggttgaag ccccgggaga    780
aatagaggtc gcatcaaaat tattaatgga tgacattacg atggaggaag atcctttata    840
ttatcggtac caacagcttc actgtgaact gtttcctctt g                        881
```

<210> SEQ ID NO 9
<211> LENGTH: 882
<212> TYPE: DNA
<213> ORGANISM: Artificial Sequence
<220> FEATURE:
<223> OTHER INFORMATION: cDNA parp2 part 2 variant 2

<400> SEQUENCE: 9

```
gagaaaattg ttaccgcgac aaggaagggg tggctgttct ggatcaaggg atcccagatg     60
acataaaggc tcattatcat gttctacaaa agggtgatga tatctatgat gccatgttaa    120
atcagacgaa tgttgggcaa acaataaca aattctttgt gatccagctt ctagaatctg    180
atgactcgaa gacatacatg gttcataaca gatggggtag agttggtgtg aagggtcaaa    240
ttaagttaca tggccccttt acttcacgac aagccgcaat tgatgagttt caaaccaaat    300
tctttaacaa gaccaaaaac tattggtaca acagaaaaga ctttgtttgt cacccaaagt    360
gctacaccttt gctggagatg gactatgatg aaaagaaaag gaatctgat gtcaaaagaa    420
aggctaactc ttccattggt gctcaattgc gggagacaaa gcttgaacaa cgtgttgcta    480
agtttatctc tattatgtgc aatatcagca tgatgaagca caaatgatg gaaataggat    540
acaatgctga aagttgcct cttggtaagc taagcaaatc cacaattta aaggggtatg    600
atgtcttaaa gaaaattgct gatgtgattg accagtcaaa caggagcaag cttgagcaat    660
taagttcgga attttacacc gtgattccac tgattttgg atttagaaaaa atgcgtgatt    720
tcgtcatcga cacacctcag aagttgaaaa agaagttgga aatggttgaa gccctgggag    780
aaatagaggt cgcatcaaaa ttattaatgg atgacattac gatggaggaa gatcctttat    840
```

| attatcggta ccaacagctt cactgtgaac tgtttcctct tg | 882 |

```
<210> SEQ ID NO 10
<211> LENGTH: 869
<212> TYPE: DNA
<213> ORGANISM: Artificial Sequence
<220> FEATURE:
<223> OTHER INFORMATION: cDNA parp2 part 2 variant 3

<400> SEQUENCE: 10
```

| cagccacgag aagggggtgg ctgttctgga tcaagggatc ccagacgaca taaaggctca | 60 |
| ttatcatgtc ctacaaaagg gtgatgatat ctatgatgcc atgttaaatc agacgaatgt | 120 |
| tgggcaaaac aataacaaat tctttgtgat ccagcttcta gaatctgatg actcgaagac | 180 |
| atacatggtt cataacagat ggggtagagt tggtgtgaag ggtcaaatta agttacatgg | 240 |
| cccctttact tcacgacaag ccgcaattga tgagtttcaa accaaattct taacaagac | 300 |
| caaaaactat tggtacaaca gaaaagactt tgtttgtcac ccaaagtgct acaccttgct | 360 |
| ggagatggac tatgatgaaa agaaaagga tctgatgtc aaaagaaagg ctaactcttc | 420 |
| cattggtgct caattgcggg agacagagct gaacaacgt gttgctaagt ttatctctat | 480 |
| tatatgcaat atcagcatga tgaagcaaca atgatggaa ataggataca atgctgacaa | 540 |
| gttgcctctt ggtaagctaa gcaaatccac aattttaaag gggtatgatg tcttaaagaa | 600 |
| aattgctgat gtgattgacc agtcaaacag gagcaagctt gagcaattaa gttcggaatt | 660 |
| ttacaccgtg attccacatg attttggatt tagaaaaatg cgtgatttg tcatcgacac | 720 |
| acctcagaag ttgaaaaaga gttggaaat ggttgaagcc ctgggagaaa tagaggtcgc | 780 |
| atctaaatta ttaatggatg acattacgat ggaggaagat cctttatatt atcggtacca | 840 |
| acagcttcac tgtgaactgt ttcctcttg | 869 |

```
<210> SEQ ID NO 11
<211> LENGTH: 880
<212> TYPE: DNA
<213> ORGANISM: Artificial Sequence
<220> FEATURE:
<223> OTHER INFORMATION: cDNA parp2 part 2 variant 4

<400> SEQUENCE: 11
```

| agaagatcgt aacagcgacg aggaagggt ggctgttctg gatcaaggga tcccagatga | 60 |
| gataaaggct cattatcatg ttctacaaaa gggtgatcat atctatgatg ccatgttaaa | 120 |
| tcagacgaat gttgggcaaa acaataacaa gttctttgtg atccagcttc tagaatctga | 180 |
| tgactcaaag acatacatgg ttcataatag atggggtaga gttggtgtga agggtcaaat | 240 |
| taagttacat ggcccccttta cttcacgaca ggctgcaatt gatgtgtttc aaaccaagtt | 300 |
| ctttaacaag accaaaaact attggtacaa cagaaaagac tttgtttgtc acccaaagtg | 360 |
| ctacaccttg ctggagatgg actatgatga aaaagaaaag gattctgatg tcaaaagaaa | 420 |
| ggctaactct tccattggtg ctcaattgcg ggagacaaag cttgaacaac gtgttgctaa | 480 |
| gtttatctct gttatatgca atatcagcat gatgaagcaa caaatgatgg aaataggata | 540 |
| caatgctgac aagttgcctc ttggtaagct aagcaaatcc acaattttaa aggggtatga | 600 |
| tatcttaaag aaaattgctg atgtgattga ccagtcaaac aggagcaagc ttgagcaatt | 660 |
| aagttcggaa ttttacaccg tgattccaca tgattttgga tttagaaaaa tgcgtgattt | 720 |
| tgtcatcgac aaacctcaga gttgaaaaa gaagttggaa atggttgaag ccctgggaga | 780 |
| aatagaggtc gcatcaaaat tattaatgga tgacattacg atggaggaag atcctttata | 840 |

-continued

```
ttatcggtac cagcagcttc actgtgaact gtttcctctt                    880
```

<210> SEQ ID NO 12
<211> LENGTH: 1384
<212> TYPE: DNA
<213> ORGANISM: Artificial Sequence
<220> FEATURE:
<223> OTHER INFORMATION: cDNA parp2 (fused)
<220> FEATURE:
<221> NAME/KEY: CDS
<222> LOCATION: (3)..(1382)
<223> OTHER INFORMATION: partial amino acid sequence of cotton parp2
      protein
<220> FEATURE:
<221> NAME/KEY: variant
<222> LOCATION: (9)..(9)
<223> OTHER INFORMATION: g OR c OR t

<400> SEQUENCE: 12

```
ga gaa gat bgt tac agc gac gag gaa ggg gtg gct gtt ctg gat caa       47
   Glu Asp Xaa Tyr Ser Asp Glu Glu Gly Val Ala Val Leu Asp Gln
   1               5                  10                  15 ggg atc cca gat gac ata aag gct cat tat cat gtt cta caa aag ggt      95
Gly Ile Pro Asp Asp Ile Lys Ala His Tyr His Val Leu Gln Lys Gly
                20                  25                  30 gat gat atc tat gat gcc atg tta aat cag acg aat gtt ggg caa aac     143
Asp Asp Ile Tyr Asp Ala Met Leu Asn Gln Thr Asn Val Gly Gln Asn
            35                  40                  45 aat aac aaa ttc ttt gtg atc cag ctt cta gaa tct gat gac tcg aag     191
Asn Asn Lys Phe Phe Val Ile Gln Leu Leu Glu Ser Asp Asp Ser Lys
        50                  55                  60 aca tac atg gtt cat aac aga tgg ggt aga gtt ggt gtg aag ggt caa     239
Thr Tyr Met Val His Asn Arg Trp Gly Arg Val Gly Val Lys Gly Gln
    65                  70                  75 att aag tta cat ggc ccc ttt act tca cga caa gcc gca att gat gag     287
Ile Lys Leu His Gly Pro Phe Thr Ser Arg Gln Ala Ala Ile Asp Glu
80                  85                  90                  95 ttt caa acc aaa ttc ttt aac aag acc aaa aac tat tgg tac aac aga     335
Phe Gln Thr Lys Phe Phe Asn Lys Thr Lys Asn Tyr Trp Tyr Asn Arg
                100                 105                 110 aaa gac ttt gtt tgt cac cca aag tgc tac acc ttg ctg gag atg gac     383
Lys Asp Phe Val Cys His Pro Lys Cys Tyr Thr Leu Leu Glu Met Asp
            115                 120                 125 tat gat gaa aaa gaa aag gaa tct gat gtc aaa aga aag gct aac tct     431
Tyr Asp Glu Lys Glu Lys Glu Ser Asp Val Lys Arg Lys Ala Asn Ser
        130                 135                 140 tcc att ggt gct caa ttg cgg gag aca aag ctt gaa caa cgt gtt gct     479
Ser Ile Gly Ala Gln Leu Arg Glu Thr Lys Leu Glu Gln Arg Val Ala
    145                 150                 155 aag ttt atc tct att ata tgc aat atc agc atg atg aag caa caa atg     527
Lys Phe Ile Ser Ile Ile Cys Asn Ile Ser Met Met Lys Gln Gln Met
160                 165                 170                 175 atg gaa ata gga tac aat gct gac aag ttg cct ctt ggt aag cta agc     575
Met Glu Ile Gly Tyr Asn Ala Asp Lys Leu Pro Leu Gly Lys Leu Ser
                180                 185                 190 aaa tcc aca att tta aag ggg tat gat gtc tta aag aaa att gct gat     623
Lys Ser Thr Ile Leu Lys Gly Tyr Asp Val Leu Lys Lys Ile Ala Asp
            195                 200                 205 gtg att gac cag tca aac agg agc aag ctt gag caa tta agt tcg gaa     671
Val Ile Asp Gln Ser Asn Arg Ser Lys Leu Glu Gln Leu Ser Ser Glu
        210                 215                 220 ttt tac acc gtg att cca cat gat ttt gga ttt aga aaa atg cgt gat     719
Phe Tyr Thr Val Ile Pro His Asp Phe Gly Phe Arg Lys Met Arg Asp
```

|  |  |  |  |  |  |  |  |  |  |  |  |  |  |  |  |
|---|---|---|---|---|---|---|---|---|---|---|---|---|---|---|---|
| | | 225 | | | | 230 | | | | | 235 | | | | |
| ttt | gtc | atc | gac | aca | cct | cag | aag | ttg | aaa | aag | aag | ttg | gaa | atg | gtt | 767
| Phe | Val | Ile | Asp | Thr | Pro | Gln | Lys | Leu | Lys | Lys | Lys | Leu | Glu | Met | Val |
| 240 | | | | | 245 | | | | | 250 | | | | | 255 |
| gaa | gcc | ctg | gga | gaa | ata | gag | gtc | gca | tca | aaa | tta | tta | atg | gat | gac | 815
| Glu | Ala | Leu | Gly | Glu | Ile | Glu | Val | Ala | Ser | Lys | Leu | Leu | Met | Asp | Asp |
| | | | | | 260 | | | | | 265 | | | | | 270 |
| att | acg | atg | gag | gaa | gat | cct | tta | tat | tat | cgg | tac | caa | cag | ctt | cac | 863
| Ile | Thr | Met | Glu | Glu | Asp | Pro | Leu | Tyr | Tyr | Arg | Tyr | Gln | Gln | Leu | His |
| | | | | 275 | | | | | 280 | | | | | 285 | |
| tgt | gaa | ctg | ttt | cct | ctt | gac | aat | gat | act | gag | gag | ttc | gct | ttg | att | 911
| Cys | Glu | Leu | Phe | Pro | Leu | Asp | Asn | Asp | Thr | Glu | Glu | Phe | Ala | Leu | Ile |
| | | | 290 | | | | | 295 | | | | | 300 | | |
| gta | aag | tat | att | cag | aat | act | cat | gct | cag | aca | cat | tca | aat | tat | aca | 959
| Val | Lys | Tyr | Ile | Gln | Asn | Thr | His | Ala | Gln | Thr | His | Ser | Asn | Tyr | Thr |
| | 305 | | | | | 310 | | | | | 315 | | | | |
| gtt | gat | gtt | gtt | caa | ata | ttc | aag | gtg | aca | aga | gac | ggt | gaa | agt | gaa | 1007
| Val | Asp | Val | Val | Gln | Ile | Phe | Lys | Val | Thr | Arg | Asp | Gly | Glu | Ser | Glu |
| 320 | | | | | 325 | | | | | 330 | | | | | 335 |
| cgc | ttt | aaa | aag | ttt | tct | gga | aca | aaa | aat | aga | atg | ctg | ttg | tgg | cat | 1055
| Arg | Phe | Lys | Lys | Phe | Ser | Gly | Thr | Lys | Asn | Arg | Met | Leu | Leu | Trp | His |
| | | | | 340 | | | | | 345 | | | | | 350 | |
| ggt | tct | cgg | ctt | act | aac | tgg | act | ggc | att | ctg | tcc | caa | ggt | ttg | cgc | 1103
| Gly | Ser | Arg | Leu | Thr | Asn | Trp | Thr | Gly | Ile | Leu | Ser | Gln | Gly | Leu | Arg |
| | | 355 | | | | | 360 | | | | | 365 | | | |
| att | gct | cca | cct | gaa | gcg | cct | gcc | acg | ggt | tat | atg | ttt | ggg | aag | ggg | 1151
| Ile | Ala | Pro | Pro | Glu | Ala | Pro | Ala | Thr | Gly | Tyr | Met | Phe | Gly | Lys | Gly |
| | | 370 | | | | | 375 | | | | | 380 | | | |
| gtt | tac | ttt | gct | gat | atg | ttc | tcc | aaa | agt | gca | aat | tat | tgc | tat | act | 1199
| Val | Tyr | Phe | Ala | Asp | Met | Phe | Ser | Lys | Ser | Ala | Asn | Tyr | Cys | Tyr | Thr |
| 385 | | | | | 390 | | | | | 395 | | | | | |
| aat | tct | gcc | ttc | aca | aca | ggg | gtg | ttg | ctt | cta | tgt | gag | gtt | gcc | ctg | 1247
| Asn | Ser | Ala | Phe | Thr | Thr | Gly | Val | Leu | Leu | Leu | Cys | Glu | Val | Ala | Leu |
| 400 | | | | | 405 | | | | | 410 | | | | | 415 |
| ggt | gac | atg | gct | gag | ctt | cta | caa | gct | aaa | agc | gat | gct | gat | aag | ctg | 1295
| Gly | Asp | Met | Ala | Glu | Leu | Leu | Gln | Ala | Lys | Ser | Asp | Ala | Asp | Lys | Leu |
| | | | | 420 | | | | | 425 | | | | | 430 | |
| ccg | gat | ggg | aag | ttg | agc | aca | aaa | ggt | gtt | ggt | gca | act | gca | ccg | gat | 1343
| Pro | Asp | Gly | Lys | Leu | Ser | Thr | Lys | Gly | Val | Gly | Ala | Thr | Ala | Pro | Asp |
| | | 435 | | | | | 440 | | | | | 445 | | | |
| cct | tct | gaa | gcc | cag | tca | ctt | gat | gat | ggt | gtt | gtt | gtt | cc | | | 1384
| Pro | Ser | Glu | Ala | Gln | Ser | Leu | Asp | Asp | Gly | Val | Val | Val | | | |
| | | 450 | | | | | 455 | | | | | 460 | | | |

<210> SEQ ID NO 13
<211> LENGTH: 460
<212> TYPE: PRT
<213> ORGANISM: Artificial Sequence
<220> FEATURE:
<221> NAME/KEY: misc_feature
<222> LOCATION: (3)..(3)
<223> OTHER INFORMATION: Xaa can be Gly OR Arg OR Cys
<220> FEATURE:
<223> OTHER INFORMATION: Synthetic Construct

<400> SEQUENCE: 13

| Glu | Asp | Xaa | Tyr | Ser | Asp | Glu | Glu | Gly | Val | Ala | Val | Leu | Asp | Gln | Gly |
|---|---|---|---|---|---|---|---|---|---|---|---|---|---|---|---|
| 1 | | | | 5 | | | | | 10 | | | | | 15 | |

| Ile | Pro | Asp | Asp | Ile | Lys | Ala | His | Tyr | His | Val | Leu | Gln | Lys | Gly | Asp |
|---|---|---|---|---|---|---|---|---|---|---|---|---|---|---|---|
| | | | 20 | | | | | 25 | | | | | 30 | | |

| Asp | Ile | Tyr | Asp | Ala | Met | Leu | Asn | Gln | Thr | Asn | Val | Gly | Gln | Asn | Asn |
|---|---|---|---|---|---|---|---|---|---|---|---|---|---|---|---|
| | | 35 | | | | | 40 | | | | | 45 | | | |

-continued

```
Asn Lys Phe Phe Val Ile Gln Leu Leu Glu Ser Asp Asp Ser Lys Thr
    50                  55                  60
Tyr Met Val His Asn Arg Trp Gly Arg Val Gly Val Lys Gly Gln Ile
65                  70                  75                  80
Lys Leu His Gly Pro Phe Thr Ser Arg Gln Ala Ala Ile Asp Glu Phe
                85                  90                  95
Gln Thr Lys Phe Phe Asn Lys Thr Lys Asn Tyr Trp Tyr Asn Arg Lys
            100                 105                 110
Asp Phe Val Cys His Pro Lys Cys Tyr Thr Leu Leu Glu Met Asp Tyr
            115                 120                 125
Asp Glu Lys Glu Lys Glu Ser Asp Val Lys Arg Lys Ala Asn Ser Ser
            130                 135                 140
Ile Gly Ala Gln Leu Arg Glu Thr Lys Leu Glu Gln Arg Val Ala Lys
145                 150                 155                 160
Phe Ile Ser Ile Ile Cys Asn Ile Ser Met Met Lys Gln Gln Met Met
                165                 170                 175
Glu Ile Gly Tyr Asn Ala Asp Lys Leu Pro Leu Gly Lys Leu Ser Lys
                180                 185                 190
Ser Thr Ile Leu Lys Gly Tyr Asp Val Leu Lys Lys Ile Ala Asp Val
                195                 200                 205
Ile Asp Gln Ser Asn Arg Ser Lys Leu Glu Gln Leu Ser Ser Glu Phe
210                 215                 220
Tyr Thr Val Ile Pro His Asp Phe Gly Phe Arg Lys Met Arg Asp Phe
225                 230                 235                 240
Val Ile Asp Thr Pro Gln Lys Leu Lys Lys Leu Glu Met Val Glu
                245                 250                 255
Ala Leu Gly Glu Ile Glu Val Ala Ser Lys Leu Leu Met Asp Asp Ile
                260                 265                 270
Thr Met Glu Glu Asp Pro Leu Tyr Tyr Arg Tyr Gln Gln Leu His Cys
                275                 280                 285
Glu Leu Phe Pro Leu Asp Asn Asp Thr Glu Glu Phe Ala Leu Ile Val
                290                 295                 300
Lys Tyr Ile Gln Asn Thr His Ala Gln Thr His Ser Asn Tyr Thr Val
305                 310                 315                 320
Asp Val Val Gln Ile Phe Lys Val Thr Arg Asp Gly Glu Ser Glu Arg
                325                 330                 335
Phe Lys Lys Phe Ser Gly Thr Lys Asn Arg Met Leu Leu Trp His Gly
                340                 345                 350
Ser Arg Leu Thr Asn Trp Thr Gly Ile Leu Ser Gln Gly Leu Arg Ile
                355                 360                 365
Ala Pro Pro Glu Ala Pro Ala Thr Gly Tyr Met Phe Gly Lys Gly Val
                370                 375                 380
Tyr Phe Ala Asp Met Phe Ser Lys Ser Ala Asn Tyr Cys Tyr Thr Asn
385                 390                 395                 400
Ser Ala Phe Thr Thr Gly Val Leu Leu Leu Cys Glu Val Ala Leu Gly
                405                 410                 415
Asp Met Ala Glu Leu Leu Gln Ala Lys Ser Asp Ala Asp Lys Leu Pro
                420                 425                 430
Asp Gly Lys Leu Ser Thr Lys Gly Val Gly Ala Thr Ala Pro Asp Pro
                435                 440                 445
Ser Glu Ala Gln Ser Leu Asp Asp Gly Val Val Val
450                 455                 460
```

```
<210> SEQ ID NO 14
<211> LENGTH: 5616
<212> TYPE: DNA
<213> ORGANISM: Artificial Sequence
<220> FEATURE:
<223> OTHER INFORMATION: T-DNA vector pTMT01
<220> FEATURE:
<221> NAME/KEY: misc_feature
<222> LOCATION: (1)..(25)
<223> OTHER INFORMATION: LB: left border repeat from the T-DNA of
      Agrobacterium tumefaciens (Zambryski 1988)
<220> FEATURE:
<221> NAME/KEY: misc_feature
<222> LOCATION: (25)..(439)
<223> OTHER INFORMATION: 3'nos: sequence including the 3' untranslated
      region of the nopaline synthase gene from the T-DNA of pTiT37 as
      described by Depicker et al. 1982. (counter clockwise)
<220> FEATURE:
<221> NAME/KEY: misc_feature
<222> LOCATION: (440)..(1777)
<223> OTHER INFORMATION: 2mepsps(EagI): the coding sequence (no PvuII)
      of the double-mutated 5-enol-pyruvylshikimate-3-phosphate synthase
      gene of Zea mays (corn) (Lebrun et al. 2003). (counter clockwise)
<220> FEATURE:
<221> NAME/KEY: misc_feature
<222> LOCATION: (1778)..(2150)
<223> OTHER INFORMATION: TPotp C: the optimized transit peptide as
      described by Lebrun et al. (1996). (counter clockwise)
<220> FEATURE:
<221> NAME/KEY: misc_feature
<222> LOCATION: (2151)..(2685)
<223> OTHER INFORMATION: Pcsvmv XYZ: sequence including the promoter
      region of the Cassava Vein Mosaic Virus (Verdaguer et al. 1996).
      (counter clockwise)
<220> FEATURE:
<221> NAME/KEY: misc_feature
<222> LOCATION: (2686)..(3191)
<223> OTHER INFORMATION: P35s2: sequence including the promoter region
      of the Cauliflower Mosaic Virus 35S transcript (Odell et al.
      1985). (clockwise)
<220> FEATURE:
<221> NAME/KEY: misc_feature
<222> LOCATION: (3192)..(3617)
<223> OTHER INFORMATION: parp2Gh(C-terminal): sequence including part of
      the coding sequence of the Gossypium hirsutum (cotton) non
      classical-type poly(ADP-ribose) polymerase. (clockwise)
<220> FEATURE:
<221> NAME/KEY: misc_feature
<222> LOCATION: (3649)..(4423)
<223> OTHER INFORMATION: intron pdk: second intron of the pyruvate
      orthophosphate dikinase gene from Flaveria trinervia as described
      by Rosche and Westhoff (1995). (clockwise)
<220> FEATURE:
<221> NAME/KEY: misc_feature
<222> LOCATION: (4424)..(4851)
<223> OTHER INFORMATION: parp2Gh(C-terminal): sequence including part of
      the coding sequence of the Gossypium hirsutum (cotton) non
      classical-type poly(ADP-ribose) polymerase. (counter clockwise)
<220> FEATURE:
<221> NAME/KEY: misc_feature
<222> LOCATION: (4852)..(5591)
<223> OTHER INFORMATION: 3' ocs sequence including the 3' untranslated
      region of the octopine synthase gene of Agrobacterium tumefaciens
      as described by De Greve et al. (1982). (clockwise)
<220> FEATURE:
<221> NAME/KEY: misc_feature
<222> LOCATION: (5592)..(5616)
<223> OTHER INFORMATION: RB: right border repeat from the T-DNA of
      Agrobacterium tumefaciens (Zambryski 1988)
<220> FEATURE:
<221> NAME/KEY: misc_feature
<222> LOCATION: (5592)..(5616)
<223> OTHER INFORMATION: RB: right border repeat from the T-DNA of
      Agrobacterium tumefaciens (Zambryski 1988)

<400> SEQUENCE: 14
cggcaggata tattcaattg taaatggctc catggcgatc gctacctggc tggcgaaagg    60
gggatgtgct gcaaggcgat taagttgggt aacgccaggg ttttcccagt cacgacgttg   120
```

| | |
|---|---:|
| taaaacgacg gccagtgaat tgcggccgca attcccgatc tagtaacata gatgacaccg | 180 |
| cgcgcgataa tttatcctag tttgcgcgct atattttgtt ttctatcgcg tattaaatgt | 240 |
| ataattgcgg gactctaatc ataaaaaccc atctcataaa taacgtcatg cattacatgt | 300 |
| taattattac atgcttaacg taattcaaca gaaattatat gataatcatc gcaagaccgg | 360 |
| caacaggatt caatcttaag aaactttatt gccaaatgtt tgaacgatcg gggaaattcg | 420 |
| tcgaagcttc ttctagagct taattcttga cgaaagtgct cagcacatcg aagtagtcgg | 480 |
| ggaaggtctt ccgggtgcac ccagggtccc ggatggtgac ggggacctcg gcacaggcgg | 540 |
| caagggagaa ggccatcgcc atcctgtggt cgtcgtacgt gtcgatcgcc gtcacgttca | 600 |
| gcttctccgg cggcgtgatg atgcagtagt ccggcccttc ctcaacagat gctcccagct | 660 |
| tggttagctc cgtccggatc gcaaccatcc tctcggtctc ctttactctc caggaagcca | 720 |
| cgtctctgat ggctgtcggg ccatcggcaa gagggcaac cacagcaaga gtcatggcga | 780 |
| catcaggcat cttgttcatg ttgacatcaa tcgccttgag gtgtttcctc ccaaatggct | 840 |
| cccgcggtgg gccagtaaca gttacgctag tctcggtcca tgtaaccttc gctcccatca | 900 |
| tctccagtac ctcagcaaac ttcacatcac cctgcaaact ggtggtgcca caaccttcca | 960 |
| cagtcacagt ccctccagta attgcagcac cagccaagaa atagcttgcg cttgaggcat | 1020 |
| caccttcaac ataggcattt ttaggggact tgtattttg acctccctta atgtagaatc | 1080 |
| tgtcccagct atcagaatgc tctgctttca caccaaaacg ctccatcaat ctcaatgtca | 1140 |
| tttcgacgta cggaatggag attaatttat caatgatttc aatctccaca tccccaagag | 1200 |
| ccaaaggagc agccatcagc aaggcactca agtactgact gctgatggag ccagacagct | 1260 |
| tgaccttgcc accaggtagc cctccgattc cattgacacg aacaggtggg cagtcagtgc | 1320 |
| caaggaaaca atcaacatct gcaccaagct gcttcaatcc gacaaccaag tcgccaatgg | 1380 |
| gtctctccct cattcttggt actccatcaa gcacgtaagt tgcatttcca ccagcagcag | 1440 |
| taacggccgc tgtcaaggac cgcattgcga ttccagcatt ccccaagaag agctgcactt | 1500 |
| cctctttagc atcctcaact gggaactttc caccacagcc aacaactaca gctcttttgg | 1560 |
| cagctttgtc cgcttcgaca gagagaccaa gagtcctcaa ggccccgagc atgtagtgga | 1620 |
| catcctcact gttcagcagg ttatcaacca ctgttgtccc ctcggacagg gcggcgagta | 1680 |
| ggaggatccg gttggaaagc gacttggacc ccggcagctt gacggtgccg gagatctcct | 1740 |
| tgatgggctg cagcacgatc tcctcggcgc cggccatgca ccggatcctt ccgccgttgc | 1800 |
| tgacgttgcc gaggcttctg gaggagcggc gggcgacggg gaggctggcg gtggacttga | 1860 |
| gcccctggaa cggagcgacg gcggtggccg acgaggccat catcacggtg gcgccatag | 1920 |
| acagcggcgg caggtacgac agcgtctcga acttcttgtt gccgtaggcc ggccacacct | 1980 |
| gcatacattg aactcttcca ccgttgctgg gaagggtgga gaagtcgtta gccttcttgg | 2040 |
| tggtggggaa ggcggcgttg gacttaaggc cggtgaacgg agccaccatg ttggcctgag | 2100 |
| caggggcggt ccggctaacg gtcgcgactg aggaggagat cgaagccatg gccgctttta | 2160 |
| gaattgagat ctacaaactt acaaatttct ctgaagttgt atcctcagta cttcaaagaa | 2220 |
| aatagcttac accaaatttt ttcttgtttt cacaaatgcc gaacttggtt ccttatatag | 2280 |
| gaaaactcaa gggcaaaaat gacacggaaa aatataaaag gataagtagt gggggataag | 2340 |
| attcctttgt gataaggtta ctttccgccc ttacattttc caccttacat gtgtcctcta | 2400 |
| tgtctctttc acaatcaccg accttatctt cttctttttca ttgttgtcgt cagtgcttac | 2460 |
| gtcttcaaga ttctttttctt cgcctggttc ttcttttttca atttctacgt attcttcttc | 2520 |

```
gtattctggc agtataggat cttgtatctg tacattcttc attttttgaac ataggttgca    2580
tatgtgccgc atattgatct gcttcttgct gagctcacat aatacttcca tagttttttcc    2640
cgtaaacatt ggattcttga tgctacatct tggataatta ccttctggaa gcttatcgat    2700
accgtcgagg gcatatggcg cgccgcggcc gctttacgac tcaatgacaa gaagaaaatc    2760
ttcgtcaaca tggtggagca cgacactctc gtctactcca agaatatcaa agatacagtc    2820
tcagaagacc aaagggctat tgagactttt caacaaaggg taatatcggg aaacctcctc    2880
ggattccatt gcccagctat ctgtcacttc atcaaaagga cagtagaaaa ggaaggtggc    2940
acctacaaat gccatcattg cgataaagga aaggctatcg ttcaagatgc ctctgccgac    3000
agtggtccca agatggaccc ccacccacg aggagcatcg tggaaaaaga agacgttcca    3060
accacgtctt caaagcaagt ggattgatgt gatatctcca ctgacgtaag ggatgacgca    3120
caatcccact atccttcgca agacccttcc tctatataag gaagttcatt tcatttggag    3180
aggactcgag taccagcagc atcactgtga actgtttcct cttgacaatg atactgagga    3240
gttcgctttg attgtaaagt atattcagaa tactcatgct cagacacatt caaattatac    3300
agttgatgtt gttcaaatat tcaaggtgac aagagacggt gaaagtgaac gctttaaaaa    3360
gttttctgga acaaaaaata gaatgctgtt gtggcatggt tctcggctta ctaactggac    3420
tggcattctg tcccaaggtt tgcgcattgc tccacctgaa gcgcctgcca cgggttatat    3480
gtttgggaag ggggtttact ttgctgatat gttctccaaa agtgcaaatt attgctatac    3540
taattctgcc ttcacaacag gggtgttgct tctatgtgag gttgccctgg gtgacatggc    3600
tgagcttcta caagctaggt accccagctt ggtaaggaaa taattatttt cttttttcct    3660
tttagtataa aatagttaag tgatgttaat tagtatgatt ataataatat agttgttata    3720
attgtgaaaa aataaattat aaatatattg tttacataaa caacatagta atgtaaaaaa    3780
atatgacaag tgatgtgtaa gacgaagaag ataaaagttg agagtaagta tattattttt    3840
aatgaatttg atcgaacatg taagatgata tactagcatt aatatttgtt ttaatcataa    3900
tagtaattct agctggtttg atgaattaaa tatcaatgat aaaatactat agtaaaaata    3960
agaataaaata aattaaaata atattttttt atgattaata gtttattata taattaaata    4020
tctataccat tactaaatat tttagtttaa agttaataa atattttgtt agaaattcca    4080
atctgcttgt aatttatcaa taaacaaaat attaaataac aagctaaagt aacaaataat    4140
atcaaactaa tagaaacagt aatctaatgt aacaaaacat aatctaatgc taatataaca    4200
aagcgcaaga tctatcattt tatatagtat tattttcaat caacattctt attaatttct    4260
aaataatact tgtagtttta ttaacttcta aatggattga ctattaatta aatgaattag    4320
tcgaacatga ataaacaagg taacatgata gatcatgtca ttgtgttatc attgatctta    4380
catttggatt gattacagtt gggaagctgg gttcgaaatc gattagcttg tagaagctca    4440
gccatgtcac ccagggcaac ctcacataga agcaacaccc ctgttgtgaa ggcagaatta    4500
gtatagcaat aatttgcact tttggagaac atatcagcaa agtaaacccc cttcccaaac    4560
atataacccg tggcaggcgc ttcaggtgga gcaatgcgca aaccttggga cagaatgcca    4620
gtccagttag taagccgaga accatgccac aacagcattc tattttttgt tccagaaaac    4680
tttttaaagc gttcactttc accgtctctt gtcaccttga atatttgaac aacatcaact    4740
gtataatttg aatgtgtctg agcatgagta ttctgaatat actttacaat caaagcgaac    4800
tcctcagtat cattgtcaag aggaaacagt tcacagtgaa gctgctggta tctagagtcc    4860
tgctttaatg agatatgcga gacgcctatg atcgcatgat atttgctttc aattctgttg    4920
```

```
tgcacgttgt aaaaaacctg agcatgtgta gctcagatcc ttaccgccgg tttcggttca    4980
ttctaatgaa tatatcaccc gttactatcg tatttttatg aataatattc tccgttcaat    5040
ttactgattg taccctacta cttatatgta caatattaaa atgaaaacaa tatattgtgc    5100
tgaataggtt tatagcgaca tctatgatag agcgccacaa taacaaacaa ttgcgtttta    5160
ttattacaaa tccaatttta aaaaagcgg cagaaccggt caaacctaaa agactgatta    5220
cataaatctt attcaaattt caaaaggccc caggggctag tatctacgac acaccgagcg    5280
gcgaactaat aacgttcact gaagggaact ccggttcccc gccggcgcgc atgggtgaga    5340
ttccttgaag ttgagtattg gccgtccgct ctaccgaaag ttacgggcac cattcaaccc    5400
ggtccagcac ggcggccggg taaccgactt gctgccccga gaattatgca gcatttttt    5460 ggtgtatgtg ggccccaaat gaagtgcagg tcaaaccttg acagtgacga caaatcgttg    5520
ggcgggtcca gggcgaattt tgcgacaaca tgtcgaggct cagcaggacc tgcaggtcga    5580
cggccgagta ctggcaggat ataccgtt gtaatt                                5616
```

```
<210> SEQ ID NO 15
<211> LENGTH: 457
<212> TYPE: PRT
<213> ORGANISM: Artificial Sequence
<220> FEATURE:
<223> OTHER INFORMATION: Variant cotton parp2 fragments
<220> FEATURE:
<221> NAME/KEY: VARIANT
<222> LOCATION: (1)..(1)
<223> OTHER INFORMATION: Xaa can be Tyr OR Phe OR Trp
<220> FEATURE:
<221> NAME/KEY: VARIANT
<222> LOCATION: (2)..(2)
<223> OTHER INFORMATION: Xaa can be Ser OR Thr
<220> FEATURE:
<221> NAME/KEY: VARIANT
<222> LOCATION: (3)..(3)
<223> OTHER INFORMATION: Xaa can be Asp OR Glu
<220> FEATURE:
<221> NAME/KEY: VARIANT
<222> LOCATION: (4)..(4)
<223> OTHER INFORMATION: Xaa can be Asp OR Glu
<220> FEATURE:
<221> NAME/KEY: VARIANT
<222> LOCATION: (5)..(5)
<223> OTHER INFORMATION: Xaa can be Asp OR Glu
<220> FEATURE:
<221> NAME/KEY: VARIANT
<222> LOCATION: (6)..(6)
<223> OTHER INFORMATION: Xaa can be Gly OR Ala OR Val OR Leu OR Ile
<220> FEATURE:
<221> NAME/KEY: VARIANT
<222> LOCATION: (7)..(7)
<223> OTHER INFORMATION: Xaa can be Val OR Ala OR Gly OR Leu OR Ile
<220> FEATURE:
<221> NAME/KEY: VARIANT
<222> LOCATION: (8)..(8)
<223> OTHER INFORMATION: Xaa can be Ala OR Val OR Gly OR Leu OR Ile
<220> FEATURE:
<221> NAME/KEY: VARIANT
<222> LOCATION: (9)..(9)
<223> OTHER INFORMATION: Xaa can be Val OR Ala OR Gly OR Leu OR Ile
<220> FEATURE:
<221> NAME/KEY: VARIANT
<222> LOCATION: (10)..(10)
<223> OTHER INFORMATION: Xaa can be Leu OR Ala OR Gly OR Val OR Ile
<220> FEATURE:
<221> NAME/KEY: VARIANT
<222> LOCATION: (11)..(11)
<223> OTHER INFORMATION: Xaa can be Asp OR Glu
<220> FEATURE:
<221> NAME/KEY: VARIANT
<222> LOCATION: (12)..(12)
<223> OTHER INFORMATION: Xaa can be Gln OR Asn
```

```
<220> FEATURE:
<221> NAME/KEY: VARIANT
<222> LOCATION: (13)..(13)
<223> OTHER INFORMATION: Xaa can be Gly OR Ala OR Val OR Leu OR Ile
<220> FEATURE:
<221> NAME/KEY: VARIANT
<222> LOCATION: (14)..(14)
<223> OTHER INFORMATION: Xaa can be Ile OR Ala OR Val OR Leu OR Gly
<220> FEATURE:
<221> NAME/KEY: VARIANT
<222> LOCATION: (16)..(16)
<223> OTHER INFORMATION: Xaa can be Asp OR Glu
<220> FEATURE:
<221> NAME/KEY: VARIANT
<222> LOCATION: (17)..(17)
<223> OTHER INFORMATION: Xaa can be Asp OR Glu
<220> FEATURE:
<221> NAME/KEY: VARIANT
<222> LOCATION: (18)..(18)
<223> OTHER INFORMATION: Xaa can be Ile OR Ala OR Val OR Gly OR Leu
<220> FEATURE:
<221> NAME/KEY: VARIANT
<222> LOCATION: (19)..(19)
<223> OTHER INFORMATION: Xaa can be Lys OR Arg OR His
<220> FEATURE:
<221> NAME/KEY: VARIANT
<222> LOCATION: (20)..(20)
<223> OTHER INFORMATION: Xaa can be Ala OR Val OR Leu OR Ile OR Gly
<220> FEATURE:
<221> NAME/KEY: VARIANT
<222> LOCATION: (21)..(21)
<223> OTHER INFORMATION: Xaa can be His OR Arg OR Lys
<220> FEATURE:
<221> NAME/KEY: VARIANT
<222> LOCATION: (22)..(22)
<223> OTHER INFORMATION: Xaa can be Tyr OR Phe OR Trp
<220> FEATURE:
<221> NAME/KEY: VARIANT
<222> LOCATION: (23)..(23)
<223> OTHER INFORMATION: Xaa can be His OR Arg OR Lys
<220> FEATURE:
<221> NAME/KEY: VARIANT
<222> LOCATION: (24)..(24)
<223> OTHER INFORMATION: Xaa can be Val OR Ala OR Ile OR Leu OR Gly
<220> FEATURE:
<221> NAME/KEY: VARIANT
<222> LOCATION: (25)..(25)
<223> OTHER INFORMATION: Xaa can be Leu OR Ala OR Ile OR Val OR Gly
<220> FEATURE:
<221> NAME/KEY: VARIANT
<222> LOCATION: (26)..(26)
<223> OTHER INFORMATION: Xaa can be Gln OR Asn
<220> FEATURE:
<221> NAME/KEY: VARIANT
<222> LOCATION: (27)..(27)
<223> OTHER INFORMATION: Xaa can be Lys OR Arg OR His
<220> FEATURE:
<221> NAME/KEY: VARIANT
<222> LOCATION: (28)..(28)
<223> OTHER INFORMATION: Xaa can be Gly OR Val OR Leu OR Ile OR Ala
<220> FEATURE:
<221> NAME/KEY: VARIANT
<222> LOCATION: (29)..(29)
<223> OTHER INFORMATION: Xaa can be Asp OR Glu
<220> FEATURE:
<221> NAME/KEY: VARIANT
<222> LOCATION: (30)..(30)
<223> OTHER INFORMATION: Xaa can be Asp OR Glu
<220> FEATURE:
<221> NAME/KEY: VARIANT
<222> LOCATION: (31)..(31)
<223> OTHER INFORMATION: Xaa can be Ile OR Leu OR Gly OR Val OR Ala
<220> FEATURE:
<221> NAME/KEY: VARIANT
<222> LOCATION: (32)..(32)
<223> OTHER INFORMATION: Xaa can be Tyr OR Phe OR Trp
<220> FEATURE:
<221> NAME/KEY: VARIANT
<222> LOCATION: (33)..(33)
<223> OTHER INFORMATION: Xaa can be Asp OR Glu
```

```
<220> FEATURE:
<221> NAME/KEY: VARIANT
<222> LOCATION: (34)..(34)
<223> OTHER INFORMATION: Xaa can be Ala OR Gly OR Val OR Leu OR Ile
<220> FEATURE:
<221> NAME/KEY: VARIANT
<222> LOCATION: (36)..(36)
<223> OTHER INFORMATION: Xaa can be Leu OR Gly OR Val OR Ile OR Ala
<220> FEATURE:
<221> NAME/KEY: VARIANT
<222> LOCATION: (37)..(37)
<223> OTHER INFORMATION: Xaa can be Asn OR Gln
<220> FEATURE:
<221> NAME/KEY: VARIANT
<222> LOCATION: (38)..(38)
<223> OTHER INFORMATION: Xaa can be Gln OR Asn
<220> FEATURE:
<221> NAME/KEY: VARIANT
<222> LOCATION: (39)..(39)
<223> OTHER INFORMATION: Xaa can be Thr OR Ser
<220> FEATURE:
<221> NAME/KEY: VARIANT
<222> LOCATION: (40)..(40)
<223> OTHER INFORMATION: Xaa can be Asn OR Gln
<220> FEATURE:
<221> NAME/KEY: VARIANT
<222> LOCATION: (41)..(41)
<223> OTHER INFORMATION: Xaa can be Val OR Ala OR Gly OR Ile OR Leu
<220> FEATURE:
<221> NAME/KEY: VARIANT
<222> LOCATION: (42)..(42)
<223> OTHER INFORMATION: Xaa can be Gly OR Val OR Ala OR Ile OR Leu
<220> FEATURE:
<221> NAME/KEY: VARIANT
<222> LOCATION: (43)..(43)
<223> OTHER INFORMATION: Xaa can be Gln OR Asn
<220> FEATURE:
<221> NAME/KEY: VARIANT
<222> LOCATION: (44)..(44)
<223> OTHER INFORMATION: Xaa can be Asn OR Gln
<220> FEATURE:
<221> NAME/KEY: VARIANT
<222> LOCATION: (45)..(45)
<223> OTHER INFORMATION: Xaa can be Asn OR Gln
<220> FEATURE:
<221> NAME/KEY: VARIANT
<222> LOCATION: (46)..(46)
<223> OTHER INFORMATION: Xaa can be Asn OR Gln
<220> FEATURE:
<221> NAME/KEY: VARIANT
<222> LOCATION: (47)..(47)
<223> OTHER INFORMATION: Xaa can be Lys OR Arg OR His
<220> FEATURE:
<221> NAME/KEY: VARIANT
<222> LOCATION: (48)..(48)
<223> OTHER INFORMATION: Xaa can be Phe OR Tyr OR Trp
<220> FEATURE:
<221> NAME/KEY: VARIANT
<222> LOCATION: (49)..(49)
<223> OTHER INFORMATION: Xaa can be Phe OR Tyr OR Trp
<220> FEATURE:
<221> NAME/KEY: VARIANT
<222> LOCATION: (50)..(50)
<223> OTHER INFORMATION: Xaa can be Val OR Gly OR Ile OR Leu OR Ala
<220> FEATURE:
<221> NAME/KEY: VARIANT
<222> LOCATION: (51)..(51)
<223> OTHER INFORMATION: Xaa can be Ile OR Gly OR Val OR Leu OR Ala
<220> FEATURE:
<221> NAME/KEY: VARIANT
<222> LOCATION: (52)..(52)
<223> OTHER INFORMATION: Xaa can be Gln OR Asn
<220> FEATURE:
<221> NAME/KEY: VARIANT
<222> LOCATION: (53)..(53)
<223> OTHER INFORMATION: Xaa can be Leu OR Gly OR Val OR Ile OR Ala
<220> FEATURE:
<221> NAME/KEY: VARIANT
<222> LOCATION: (54)..(54)
<223> OTHER INFORMATION: Xaa can be Leu OR Gly OR Val OR Ile OR Ala
```

-continued

```
<220> FEATURE:
<221> NAME/KEY: VARIANT
<222> LOCATION: (55)..(55)
<223> OTHER INFORMATION: Xaa can be Glu OR Asp
<220> FEATURE:
<221> NAME/KEY: VARIANT
<222> LOCATION: (56)..(56)
<223> OTHER INFORMATION: Xaa can be Ser OR Thr
<220> FEATURE:
<221> NAME/KEY: VARIANT
<222> LOCATION: (57)..(57)
<223> OTHER INFORMATION: Xaa can be Asp OR Glu
<220> FEATURE:
<221> NAME/KEY: VARIANT
<222> LOCATION: (58)..(58)
<223> OTHER INFORMATION: Xaa can be Asp OR Glu
<220> FEATURE:
<221> NAME/KEY: VARIANT
<222> LOCATION: (59)..(59)
<223> OTHER INFORMATION: Xaa can be Ser OR Thr
<220> FEATURE:
<221> NAME/KEY: VARIANT
<222> LOCATION: (60)..(60)
<223> OTHER INFORMATION: Xaa can be Lys OR Arg OR His
<220> FEATURE:
<221> NAME/KEY: VARIANT
<222> LOCATION: (61)..(61)
<223> OTHER INFORMATION: Xaa can be Thr OR Ser
<220> FEATURE:
<221> NAME/KEY: VARIANT
<222> LOCATION: (62)..(62)
<223> OTHER INFORMATION: Xaa can be Tyr OR Phe OR Trp
<220> FEATURE:
<221> NAME/KEY: VARIANT
<222> LOCATION: (64)..(64)
<223> OTHER INFORMATION: Xaa can be Val OR Gly OR Ile OR Leu OR Ala
<220> FEATURE:
<221> NAME/KEY: VARIANT
<222> LOCATION: (65)..(65)
<223> OTHER INFORMATION: Xaa can be His OR Arg OR Lys
<220> FEATURE:
<221> NAME/KEY: VARIANT
<222> LOCATION: (66)..(66)
<223> OTHER INFORMATION: Xaa can be Asn  OR Gln
<220> FEATURE:
<221> NAME/KEY: VARIANT
<222> LOCATION: (67)..(67)
<223> OTHER INFORMATION: Xaa can be Arg OR His OR Lys
<220> FEATURE:
<221> NAME/KEY: VARIANT
<222> LOCATION: (68)..(68)
<223> OTHER INFORMATION: Xaa can be Trp OR Phe OR Tyr
<220> FEATURE:
<221> NAME/KEY: VARIANT
<222> LOCATION: (69)..(69)
<223> OTHER INFORMATION: Xaa can be Gly OR Ala OR Val OR Ile OR Leu
<220> FEATURE:
<221> NAME/KEY: VARIANT
<222> LOCATION: (70)..(70)
<223> OTHER INFORMATION: Xaa can be Arg OR Lys OR His
<220> FEATURE:
<221> NAME/KEY: VARIANT
<222> LOCATION: (71)..(71)
<223> OTHER INFORMATION: Xaa can be Val OR Gly OR Ala OR Ile OR Leu
<220> FEATURE:
<221> NAME/KEY: VARIANT
<222> LOCATION: (72)..(72)
<223> OTHER INFORMATION: Xaa can be Gly OR Val OR Ala OR Ile OR Leu
<220> FEATURE:
<221> NAME/KEY: VARIANT
<222> LOCATION: (73)..(73)
<223> OTHER INFORMATION: Xaa can be Val OR Arg OR His
<220> FEATURE:
<221> NAME/KEY: VARIANT
<222> LOCATION: (74)..(74)
<223> OTHER INFORMATION: Xaa can be Lys OR Val OR Ala OR Ile OR Leu
<220> FEATURE:
<221> NAME/KEY: VARIANT
<222> LOCATION: (75)..(75)
<223> OTHER INFORMATION: Xaa can be Gly OR Asn
```

```
<220> FEATURE:
<221> NAME/KEY: VARIANT
<222> LOCATION: (76)..(76)
<223> OTHER INFORMATION: Xaa can be Gln OR Gly OR Val OR Leu OR Ala
<220> FEATURE:
<221> NAME/KEY: VARIANT
<222> LOCATION: (77)..(77)
<223> OTHER INFORMATION: Xaa can be Ile OR Arg OR His
<220> FEATURE:
<221> NAME/KEY: VARIANT
<222> LOCATION: (78)..(78)
<223> OTHER INFORMATION: Xaa can be Lys OR Gly OR Ile OR Val OR Ala
<220> FEATURE:
<221> NAME/KEY: VARIANT
<222> LOCATION: (79)..(79)
<223> OTHER INFORMATION: Xaa can be Leu OR Arg OR Lys
<220> FEATURE:
<221> NAME/KEY: VARIANT
<222> LOCATION: (80)..(80)
<223> OTHER INFORMATION: Xaa can be His OR Ile OR Ala OR Leu OR Val
<220> FEATURE:
<221> NAME/KEY: VARIANT
<222> LOCATION: (83)..(83)
<223> OTHER INFORMATION: Xaa can be Phe OR Tyr OR Trp
<220> FEATURE:
<221> NAME/KEY: VARIANT
<222> LOCATION: (84)..(84)
<223> OTHER INFORMATION: Xaa can be Thr OR Ser
<220> FEATURE:
<221> NAME/KEY: VARIANT
<222> LOCATION: (85)..(85)
<223> OTHER INFORMATION: Xaa can be Ser OR Thr
<220> FEATURE:
<221> NAME/KEY: VARIANT
<222> LOCATION: (86)..(86)
<223> OTHER INFORMATION: Xaa can be Arg OR Lys OR His
<220> FEATURE:
<221> NAME/KEY: VARIANT
<222> LOCATION: (87)..(87)
<223> OTHER INFORMATION: Xaa can be Gln OR Asn
<220> FEATURE:
<221> NAME/KEY: VARIANT
<222> LOCATION: (88)..(88)
<223> OTHER INFORMATION: Xaa can be Ala OR Gly OR Ile OR Leu OR Val
<220> FEATURE:
<221> NAME/KEY: VARIANT
<222> LOCATION: (89)..(89)
<223> OTHER INFORMATION: Xaa can be Ala OR Gly OR Ile OR Leu OR Val
<220> FEATURE:
<221> NAME/KEY: VARIANT
<222> LOCATION: (90)..(90)
<223> OTHER INFORMATION: Xaa can be Ile OR Gly OR Ala OR Leu OR Val
<220> FEATURE:
<221> NAME/KEY: VARIANT
<222> LOCATION: (91)..(91)
<223> OTHER INFORMATION: Xaa can be Asp OR Glu
<220> FEATURE:
<221> NAME/KEY: VARIANT
<222> LOCATION: (92)..(92)
<223> OTHER INFORMATION: Xaa can be Glu OR Asp
<220> FEATURE:
<221> NAME/KEY: VARIANT
<222> LOCATION: (93)..(93)
<223> OTHER INFORMATION: Xaa can be Phe OR Tyr OR Trp
<220> FEATURE:
<221> NAME/KEY: VARIANT
<222> LOCATION: (94)..(94)
<223> OTHER INFORMATION: Xaa can be Gln OR Asn
<220> FEATURE:
<221> NAME/KEY: VARIANT
<222> LOCATION: (95)..(95)
<223> OTHER INFORMATION: Xaa can be Thr OR Ser
<220> FEATURE:
<221> NAME/KEY: VARIANT
<222> LOCATION: (96)..(96)
<223> OTHER INFORMATION: Xaa can be Lys OR Arg OR His
<220> FEATURE:
<221> NAME/KEY: VARIANT
<222> LOCATION: (97)..(97)
<223> OTHER INFORMATION: Xaa can be Phe OR Tyr OR  Trp
```

```
<220> FEATURE:
<221> NAME/KEY: VARIANT
<222> LOCATION: (98)..(98)
<223> OTHER INFORMATION: Xaa can be Phe OR Tyr OR  Trp
<220> FEATURE:
<221> NAME/KEY: VARIANT
<222> LOCATION: (99)..(99)
<223> OTHER INFORMATION: Xaa can be Asn OR Gln
<220> FEATURE:
<221> NAME/KEY: VARIANT
<222> LOCATION: (100)..(100)
<223> OTHER INFORMATION: Xaa can be Lys OR Arg OR His
<220> FEATURE:
<221> NAME/KEY: VARIANT
<222> LOCATION: (101)..(101)
<223> OTHER INFORMATION: Xaa can be Thr OR Ser
<220> FEATURE:
<221> NAME/KEY: VARIANT
<222> LOCATION: (102)..(102)
<223> OTHER INFORMATION: Xaa can be Lys OR Arg OR His
<220> FEATURE:
<221> NAME/KEY: VARIANT
<222> LOCATION: (103)..(103)
<223> OTHER INFORMATION: Xaa can be Asn OR Gln
<220> FEATURE:
<221> NAME/KEY: VARIANT
<222> LOCATION: (104)..(104)
<223> OTHER INFORMATION: Xaa can be Tyr OR Phe OR Trp
<220> FEATURE:
<221> NAME/KEY: VARIANT
<222> LOCATION: (105)..(105)
<223> OTHER INFORMATION: Xaa can be Trp OR Phe OR Tyr
<220> FEATURE:
<221> NAME/KEY: VARIANT
<222> LOCATION: (106)..(106)
<223> OTHER INFORMATION: Xaa can be Tyr OR Phe OR Trp
<220> FEATURE:
<221> NAME/KEY: VARIANT
<222> LOCATION: (107)..(107)
<223> OTHER INFORMATION: Xaa can be Asn OR Gln
<220> FEATURE:
<221> NAME/KEY: VARIANT
<222> LOCATION: (108)..(108)
<223> OTHER INFORMATION: Xaa can be Arg OR Lys OR His
<220> FEATURE:
<221> NAME/KEY: VARIANT
<222> LOCATION: (109)..(109)
<223> OTHER INFORMATION: Xaa can be Lys OR Arg OR His
<220> FEATURE:
<221> NAME/KEY: VARIANT
<222> LOCATION: (110)..(110)
<223> OTHER INFORMATION: Xaa can be Asp OR Glu
<220> FEATURE:
<221> NAME/KEY: VARIANT
<222> LOCATION: (111)..(111)
<223> OTHER INFORMATION: Xaa can be Phe OR Tyr OR Trp
<220> FEATURE:
<221> NAME/KEY: VARIANT
<222> LOCATION: (112)..(112)
<223> OTHER INFORMATION: Xaa can be Val OR Gly OR Ile OR Leu OR Ala
<220> FEATURE:
<221> NAME/KEY: VARIANT
<222> LOCATION: (114)..(114)
<223> OTHER INFORMATION: Xaa can be Arg OR Lys
<220> FEATURE:
<221> NAME/KEY: VARIANT
<222> LOCATION: (116)..(116)
<223> OTHER INFORMATION: Xaa can be Lys OR Arg OR His
<220> FEATURE:
<221> NAME/KEY: VARIANT
<222> LOCATION: (118)..(118)
<223> OTHER INFORMATION: Xaa can be Tyr OR Phe OR Trp
<220> FEATURE:
<221> NAME/KEY: VARIANT
<222> LOCATION: (119)..(119)
<223> OTHER INFORMATION: Xaa can be Thr OR Ser
<220> FEATURE:
<221> NAME/KEY: VARIANT
<222> LOCATION: (120)..(120)
<223> OTHER INFORMATION: Xaa can be Leu OR Gly OR Ala OR Val OR Ile
```

```
<220> FEATURE:
<221> NAME/KEY: VARIANT
<222> LOCATION: (121)..(121)
<223> OTHER INFORMATION: Xaa can be Leu OR Gly OR Ala OR Val OR Ile
<220> FEATURE:
<221> NAME/KEY: VARIANT
<222> LOCATION: (122)..(122)
<223> OTHER INFORMATION: Xaa can be Glu OR Asp
<220> FEATURE:
<221> NAME/KEY: VARIANT
<222> LOCATION: (124)..(124)
<223> OTHER INFORMATION: Xaa can be Asp OR Glu
<220> FEATURE:
<221> NAME/KEY: VARIANT
<222> LOCATION: (125)..(125)
<223> OTHER INFORMATION: Xaa can be Tyr OR Phe OR Trp
<220> FEATURE:
<221> NAME/KEY: VARIANT
<222> LOCATION: (126)..(126)
<223> OTHER INFORMATION: Xaa can be Asp OR Glu
<220> FEATURE:
<221> NAME/KEY: VARIANT
<222> LOCATION: (127)..(127)
<223> OTHER INFORMATION: Xaa can be Glu OR Asp
<220> FEATURE:
<221> NAME/KEY: VARIANT
<222> LOCATION: (128)..(128)
<223> OTHER INFORMATION: Xaa can be Lys OR Arg OR His
<220> FEATURE:
<221> NAME/KEY: VARIANT
<222> LOCATION: (129)..(129)
<223> OTHER INFORMATION: Xaa can be Glu OR Asp
<220> FEATURE:
<221> NAME/KEY: VARIANT
<222> LOCATION: (130)..(130)
<223> OTHER INFORMATION: Xaa can be Lys OR Arg OR His
<220> FEATURE:
<221> NAME/KEY: VARIANT
<222> LOCATION: (131)..(131)
<223> OTHER INFORMATION: Xaa can be Glu OR Asp
<220> FEATURE:
<221> NAME/KEY: VARIANT
<222> LOCATION: (132)..(132)
<223> OTHER INFORMATION: Xaa can be Ser OR Thr
<220> FEATURE:
<221> NAME/KEY: VARIANT
<222> LOCATION: (133)..(133)
<223> OTHER INFORMATION: Xaa can be Asp OR Glu
<220> FEATURE:
<221> NAME/KEY: VARIANT
<222> LOCATION: (134)..(134)
<223> OTHER INFORMATION: Xaa can be Val OR Gly OR Ala OR Ile OR Leu
<220> FEATURE:
<221> NAME/KEY: VARIANT
<222> LOCATION: (135)..(135)
<223> OTHER INFORMATION: Xaa can be Lys OR Arg OR His
<220> FEATURE:
<221> NAME/KEY: VARIANT
<222> LOCATION: (136)..(136)
<223> OTHER INFORMATION: Xaa can be Arg OR Lys OR His
<220> FEATURE:
<221> NAME/KEY: VARIANT
<222> LOCATION: (137)..(137)
<223> OTHER INFORMATION: Xaa can be Lys OR Arg OR His
<220> FEATURE:
<221> NAME/KEY: VARIANT
<222> LOCATION: (138)..(138)
<223> OTHER INFORMATION: Xaa can be Ala OR Gly OR Ile OR Leu OR Val
<220> FEATURE:
<221> NAME/KEY: VARIANT
<222> LOCATION: (139)..(139)
<223> OTHER INFORMATION: Xaa can be Asn OR Gln
<220> FEATURE:
<221> NAME/KEY: VARIANT
<222> LOCATION: (140)..(140)
<223> OTHER INFORMATION: Xaa can be Ser OR Thr
<220> FEATURE:
<221> NAME/KEY: VARIANT
<222> LOCATION: (141)..(141)
<223> OTHER INFORMATION: Xaa can be Ser OR Thr
```

```
<220> FEATURE:
<221> NAME/KEY: VARIANT
<222> LOCATION: (142)..(142)
<223> OTHER INFORMATION: Xaa can be Ile OR Gly OR Val OR Leu OR Ala
<220> FEATURE:
<221> NAME/KEY: VARIANT
<222> LOCATION: (143)..(143)
<223> OTHER INFORMATION: Xaa can be Gly OR Ile OR Val OR Leu OR Ala
<220> FEATURE:
<221> NAME/KEY: VARIANT
<222> LOCATION: (144)..(144)
<223> OTHER INFORMATION: Xaa can be Ala OR Ile OR Val OR Leu OR Gly
<220> FEATURE:
<221> NAME/KEY: VARIANT
<222> LOCATION: (145)..(145)
<223> OTHER INFORMATION: Xaa can be Gln OR Asn
<220> FEATURE:
<221> NAME/KEY: VARIANT
<222> LOCATION: (146)..(146)
<223> OTHER INFORMATION: Xaa can be Leu OR Gly OR Val OR Ile OR Ala
<220> FEATURE:
<221> NAME/KEY: VARIANT
<222> LOCATION: (147)..(147)
<223> OTHER INFORMATION: Xaa can be Arg OR Lys OR His
<220> FEATURE:
<221> NAME/KEY: VARIANT
<222> LOCATION: (148)..(148)
<223> OTHER INFORMATION: Xaa can be Glu OR Asp
<220> FEATURE:
<221> NAME/KEY: VARIANT
<222> LOCATION: (149)..(149)
<223> OTHER INFORMATION: Xaa can be Thr OR Ser
<220> FEATURE:
<221> NAME/KEY: VARIANT
<222> LOCATION: (150)..(150)
<223> OTHER INFORMATION: Xaa can be Lys OR Arg OR His
<220> FEATURE:
<221> NAME/KEY: VARIANT
<222> LOCATION: (151)..(151)
<223> OTHER INFORMATION: Xaa can be Leu OR Gly OR Val OR Ile OR Ala
<220> FEATURE:
<221> NAME/KEY: VARIANT
<222> LOCATION: (152)..(152)
<223> OTHER INFORMATION: Xaa can be Glu OR Asp
<220> FEATURE:
<221> NAME/KEY: VARIANT
<222> LOCATION: (153)..(153)
<223> OTHER INFORMATION: Xaa can be Gln OR Asn
<220> FEATURE:
<221> NAME/KEY: VARIANT
<222> LOCATION: (154)..(154)
<223> OTHER INFORMATION: Xaa can be Arg OR Lys OR His
<220> FEATURE:
<221> NAME/KEY: VARIANT
<222> LOCATION: (155)..(155)
<223> OTHER INFORMATION: Xaa can be Val OR Gly OR Ile OR Leu OR Ala
<220> FEATURE:
<221> NAME/KEY: VARIANT
<222> LOCATION: (156)..(156)
<223> OTHER INFORMATION: Xaa can be Ala OR Gly OR Ile OR Leu OR Val
<220> FEATURE:
<221> NAME/KEY: VARIANT
<222> LOCATION: (157)..(157)
<223> OTHER INFORMATION: Xaa can be Lys OR Arg OR His
<220> FEATURE:
<221> NAME/KEY: VARIANT
<222> LOCATION: (158)..(158)
<223> OTHER INFORMATION: Xaa can be Phe OR Tyr OR Trp
<220> FEATURE:
<221> NAME/KEY: VARIANT
<222> LOCATION: (159)..(159)
<223> OTHER INFORMATION: Xaa can be Ile OR Gly OR Ala OR Val OR Leu
<220> FEATURE:
<221> NAME/KEY: VARIANT
<222> LOCATION: (160)..(160)
<223> OTHER INFORMATION: Xaa can be Ser OR Thr
<220> FEATURE:
<221> NAME/KEY: VARIANT
<222> LOCATION: (161)..(161)
<223> OTHER INFORMATION: Xaa can be Ile OR Gly OR Ala OR Val OR Leu
```

```
-continued

<220> FEATURE:
<221> NAME/KEY: VARIANT
<222> LOCATION: (162)..(162)
<223> OTHER INFORMATION: Xaa can be Ile OR Gly OR Ala OR Val OR Leu
<220> FEATURE:
<221> NAME/KEY: VARIANT
<222> LOCATION: (164)..(164)
<223> OTHER INFORMATION: Xaa can be Asn OR Gln
<220> FEATURE:
<221> NAME/KEY: VARIANT
<222> LOCATION: (165)..(165)
<223> OTHER INFORMATION: Xaa can be Ile OR Gly OR Ala OR Val OR Leu
<220> FEATURE:
<221> NAME/KEY: VARIANT
<222> LOCATION: (166)..(166)
<223> OTHER INFORMATION: Xaa can be Ser OR Thr
<220> FEATURE:
<221> NAME/KEY: VARIANT
<222> LOCATION: (169)..(169)
<223> OTHER INFORMATION: Xaa can be Lys OR Arg OR His
<220> FEATURE:
<221> NAME/KEY: VARIANT
<222> LOCATION: (170)..(170)
<223> OTHER INFORMATION: Xaa can be Gln OR Asn
<220> FEATURE:
<221> NAME/KEY: VARIANT
<222> LOCATION: (171)..(171)
<223> OTHER INFORMATION: Xaa can be Gln OR Asn
<220> FEATURE:
<221> NAME/KEY: VARIANT
<222> LOCATION: (174)..(174)
<223> OTHER INFORMATION: Xaa can be Glu OR Asp
<220> FEATURE:
<221> NAME/KEY: VARIANT
<222> LOCATION: (175)..(175)
<223> OTHER INFORMATION: Xaa can be Ile OR Gly OR Val OR Leu OR Ala
<220> FEATURE:
<221> NAME/KEY: VARIANT
<222> LOCATION: (176)..(176)
<223> OTHER INFORMATION: Xaa can be Gly OR Ile OR Val OR Leu OR Ala
<220> FEATURE:
<221> NAME/KEY: VARIANT
<222> LOCATION: (177)..(177)
<223> OTHER INFORMATION: Xaa can be Tyr OR Phe OR Trp
<220> FEATURE:
<221> NAME/KEY: VARIANT
<222> LOCATION: (178)..(178)
<223> OTHER INFORMATION: Xaa can be Asn OR Gln
<220> FEATURE:
<221> NAME/KEY: VARIANT
<222> LOCATION: (179)..(179)
<223> OTHER INFORMATION: Xaa can be Ala OR Gly OR Val OR Ile OR Leu
<220> FEATURE:
<221> NAME/KEY: VARIANT
<222> LOCATION: (180)..(180)
<223> OTHER INFORMATION: Xaa can be Asp OR Glu
<220> FEATURE:
<221> NAME/KEY: VARIANT
<222> LOCATION: (181)..(181)
<223> OTHER INFORMATION: Xaa can be Lys OR Arg OR His
<220> FEATURE:
<221> NAME/KEY: VARIANT
<222> LOCATION: (182)..(182)
<223> OTHER INFORMATION: Xaa can be Leu OR Gly OR Val OR Ile OR Ala
<220> FEATURE:
<221> NAME/KEY: VARIANT
<222> LOCATION: (184)..(184)
<223> OTHER INFORMATION: Xaa can be Leu OR Gly OR Val OR Ile OR Ala
<220> FEATURE:
<221> NAME/KEY: VARIANT
<222> LOCATION: (185)..(185)
<223> OTHER INFORMATION: Xaa can be Gly OR Leu OR Val OR Ile OR Ala
<220> FEATURE:
<221> NAME/KEY: VARIANT
<222> LOCATION: (186)..(186)
<223> OTHER INFORMATION: Xaa can be Lys OR Arg OR His
<220> FEATURE:
<221> NAME/KEY: VARIANT
<222> LOCATION: (187)..(187)
<223> OTHER INFORMATION: Xaa can be Leu OR Gly OR Val OR Ile OR Ala
```

```
<220> FEATURE:
<221> NAME/KEY: VARIANT
<222> LOCATION: (188)..(188)
<223> OTHER INFORMATION: Xaa can be Ser OR Thr
<220> FEATURE:
<221> NAME/KEY: VARIANT
<222> LOCATION: (189)..(189)
<223> OTHER INFORMATION: Xaa can be Lys OR Arg OR His
<220> FEATURE:
<221> NAME/KEY: VARIANT
<222> LOCATION: (190)..(190)
<223> OTHER INFORMATION: Xaa can be Ser OR Thr
<220> FEATURE:
<221> NAME/KEY: VARIANT
<222> LOCATION: (191)..(191)
<223> OTHER INFORMATION: Xaa can be Thr OR Ser
<220> FEATURE:
<221> NAME/KEY: VARIANT
<222> LOCATION: (192)..(192)
<223> OTHER INFORMATION: Xaa can be Ile OR Gly OR Val OR Leu OR Ala
<220> FEATURE:
<221> NAME/KEY: VARIANT
<222> LOCATION: (193)..(193)
<223> OTHER INFORMATION: Xaa can be Leu OR Gly OR Val OR Ile OR Ala
<220> FEATURE:
<221> NAME/KEY: VARIANT
<222> LOCATION: (194)..(194)
<223> OTHER INFORMATION: Xaa can be Lys OR Arg OR His
<220> FEATURE:
<221> NAME/KEY: VARIANT
<222> LOCATION: (195)..(195)
<223> OTHER INFORMATION: Xaa can be Gly OR Ile OR Leu OR Val OR Ala
<220> FEATURE:
<221> NAME/KEY: VARIANT
<222> LOCATION: (196)..(196)
<223> OTHER INFORMATION: Xaa can be Tyr OR Phe OR Trp
<220> FEATURE:
<221> NAME/KEY: VARIANT
<222> LOCATION: (197)..(197)
<223> OTHER INFORMATION: Xaa can be Asp OR Glu
<220> FEATURE:
<221> NAME/KEY: VARIANT
<222> LOCATION: (198)..(198)
<223> OTHER INFORMATION: Xaa can be Val OR Ile OR Ala OR Leu OR Gly
<220> FEATURE:
<221> NAME/KEY: VARIANT
<222> LOCATION: (199)..(199)
<223> OTHER INFORMATION: Xaa can be Leu OR Ile OR Ala OR Val OR Gly
<220> FEATURE:
<221> NAME/KEY: VARIANT
<222> LOCATION: (200)..(200)
<223> OTHER INFORMATION: Xaa can be Lys OR Arg OR His
<220> FEATURE:
<221> NAME/KEY: VARIANT
<222> LOCATION: (201)..(201)
<223> OTHER INFORMATION: Xaa can be Lys OR Arg OR His
<220> FEATURE:
<221> NAME/KEY: VARIANT
<222> LOCATION: (202)..(202)
<223> OTHER INFORMATION: Xaa can be Ile OR Gly OR Val OR Leu OR Ala
<220> FEATURE:
<221> NAME/KEY: VARIANT
<222> LOCATION: (203)..(203)
<223> OTHER INFORMATION: Xaa can be Ala OR Gly OR Val OR Leu OR Ile
<220> FEATURE:
<221> NAME/KEY: VARIANT
<222> LOCATION: (204)..(204)
<223> OTHER INFORMATION: Xaa can be Asp OR Glu
<220> FEATURE:
<221> NAME/KEY: VARIANT
<222> LOCATION: (205)..(205)
<223> OTHER INFORMATION: Xaa can be Val OR Gly OR Leu OR Ile OR Ala
<220> FEATURE:
<221> NAME/KEY: VARIANT
<222> LOCATION: (206)..(206)
<223> OTHER INFORMATION: Xaa can be Ile OR Gly OR Leu OR Val OR Ala
<220> FEATURE:
<221> NAME/KEY: VARIANT
<222> LOCATION: (207)..(207)
<223> OTHER INFORMATION: Xaa can be Asp OR Glu
```

```
<220> FEATURE:
<221> NAME/KEY: VARIANT
<222> LOCATION: (208)..(208)
<223> OTHER INFORMATION: Xaa can be Gln OR Asn
<220> FEATURE:
<221> NAME/KEY: VARIANT
<222> LOCATION: (209)..(209)
<223> OTHER INFORMATION: Xaa can be Ser OR Thr
<220> FEATURE:
<221> NAME/KEY: VARIANT
<222> LOCATION: (210)..(210)
<223> OTHER INFORMATION: Xaa can be Asn OR Gln
<220> FEATURE:
<221> NAME/KEY: VARIANT
<222> LOCATION: (211)..(211)
<223> OTHER INFORMATION: Xaa can be Arg OR His
<220> FEATURE:
<221> NAME/KEY: VARIANT
<222> LOCATION: (212)..(212)
<223> OTHER INFORMATION: Xaa can be Ser OR Thr
<220> FEATURE:
<221> NAME/KEY: VARIANT
<222> LOCATION: (213)..(213)
<223> OTHER INFORMATION: Xaa can be Arg OR His
<220> FEATURE:
<221> NAME/KEY: VARIANT
<222> LOCATION: (214)..(214)
<223> OTHER INFORMATION: Xaa can be Leu OR Gly OR Val OR Ala OR Ile
<220> FEATURE:
<221> NAME/KEY: VARIANT
<222> LOCATION: (215)..(215)
<223> OTHER INFORMATION: Xaa can be Glu OR Asp
<220> FEATURE:
<221> NAME/KEY: VARIANT
<222> LOCATION: (216)..(216)
<223> OTHER INFORMATION: Xaa can be Gln OR Asn
<220> FEATURE:
<221> NAME/KEY: VARIANT
<222> LOCATION: (217)..(217)
<223> OTHER INFORMATION: Xaa can be Leu OR Gly OR Val OR Ile OR Ala
<220> FEATURE:
<221> NAME/KEY: VARIANT
<222> LOCATION: (218)..(218)
<223> OTHER INFORMATION: Xaa can be Ser OR Thr
<220> FEATURE:
<221> NAME/KEY: VARIANT
<222> LOCATION: (219)..(219)
<223> OTHER INFORMATION: Xaa can be Ser OR Thr
<220> FEATURE:
<221> NAME/KEY: VARIANT
<222> LOCATION: (220)..(220)
<223> OTHER INFORMATION: Xaa can be Glu OR Asp
<220> FEATURE:
<221> NAME/KEY: VARIANT
<222> LOCATION: (221)..(221)
<223> OTHER INFORMATION: Xaa can be Phe OR Tyr OR Trp
<220> FEATURE:
<221> NAME/KEY: VARIANT
<222> LOCATION: (222)..(222)
<223> OTHER INFORMATION: Xaa can be Tyr OR Phe OR Trp
<220> FEATURE:
<221> NAME/KEY: VARIANT
<222> LOCATION: (223)..(223)
<223> OTHER INFORMATION: Xaa can be Thr OR Ser
<220> FEATURE:
<221> NAME/KEY: VARIANT
<222> LOCATION: (224)..(224)
<223> OTHER INFORMATION: Xaa can be Val OR Gly OR Ile OR Leu OR Ala
<220> FEATURE:
<221> NAME/KEY: VARIANT
<222> LOCATION: (225)..(225)
<223> OTHER INFORMATION: Xaa can be Ile OR Gly OR Val OR Leu OR Ala
<220> FEATURE:
<221> NAME/KEY: VARIANT
<222> LOCATION: (227)..(227)
<223> OTHER INFORMATION: Xaa can be His OR Arg OR Lys
<220> FEATURE:
<221> NAME/KEY: VARIANT
<222> LOCATION: (228)..(228)
<223> OTHER INFORMATION: Xaa can be Asp OR Glu
```

```
-continued

<220> FEATURE:
<221> NAME/KEY: VARIANT
<222> LOCATION: (229)..(229)
<223> OTHER INFORMATION: Xaa can be Phe OR Tyr OR Trp
<220> FEATURE:
<221> NAME/KEY: VARIANT
<222> LOCATION: (230)..(230)
<223> OTHER INFORMATION: Xaa can be Gly OR Ile OR Leu OR Ala OR Val
<220> FEATURE:
<221> NAME/KEY: VARIANT
<222> LOCATION: (231)..(231)
<223> OTHER INFORMATION: Xaa can be Phe OR Tyr OR Trp
<220> FEATURE:
<221> NAME/KEY: VARIANT
<222> LOCATION: (232)..(232)
<223> OTHER INFORMATION: Xaa can be Arg OR His OR Lys
<220> FEATURE:
<221> NAME/KEY: VARIANT
<222> LOCATION: (233)..(233)
<223> OTHER INFORMATION: Xaa can be Lys OR Arg OR Lys
<220> FEATURE:
<221> NAME/KEY: VARIANT
<222> LOCATION: (235)..(235)
<223> OTHER INFORMATION: Xaa can be Arg OR His OR Lys
<220> FEATURE:
<221> NAME/KEY: VARIANT
<222> LOCATION: (236)..(236)
<223> OTHER INFORMATION: Xaa can be Asp OR Glu
<220> FEATURE:
<221> NAME/KEY: VARIANT
<222> LOCATION: (237)..(237)
<223> OTHER INFORMATION: Xaa can be Phe OR Tyr OR Trp
<220> FEATURE:
<221> NAME/KEY: VARIANT
<222> LOCATION: (238)..(238)
<223> OTHER INFORMATION: Xaa can be Val OR Gly OR Ile OR Leu OR Ala
<220> FEATURE:
<221> NAME/KEY: VARIANT
<222> LOCATION: (239)..(239)
<223> OTHER INFORMATION: Xaa can be Ile OR Gly OR Val OR Leu OR Ala
<220> FEATURE:
<221> NAME/KEY: VARIANT
<222> LOCATION: (240)..(240)
<223> OTHER INFORMATION: Xaa can be Asp OR Glu
<220> FEATURE:
<221> NAME/KEY: VARIANT
<222> LOCATION: (241)..(241)
<223> OTHER INFORMATION: Xaa can be Thr OR Ser
<220> FEATURE:
<221> NAME/KEY: VARIANT
<222> LOCATION: (243)..(243)
<223> OTHER INFORMATION: Xaa can be Gln OR Asn
<220> FEATURE:
<221> NAME/KEY: VARIANT
<222> LOCATION: (244)..(244)
<223> OTHER INFORMATION: Xaa can be Lys OR Arg OR His
<220> FEATURE:
<221> NAME/KEY: VARIANT
<222> LOCATION: (245)..(245)
<223> OTHER INFORMATION: Xaa can be Leu OR Gly OR Val OR Ile OR Ala
<220> FEATURE:
<221> NAME/KEY: VARIANT
<222> LOCATION: (246)..(246)
<223> OTHER INFORMATION: Xaa can be Lys OR Arg OR His
<220> FEATURE:
<221> NAME/KEY: VARIANT
<222> LOCATION: (247)..(247)
<223> OTHER INFORMATION: Xaa can be Lys OR Arg OR His
<220> FEATURE:
<221> NAME/KEY: VARIANT
<222> LOCATION: (248)..(248)
<223> OTHER INFORMATION: Xaa can be Lys OR Arg OR His
<220> FEATURE:
<221> NAME/KEY: VARIANT
<222> LOCATION: (249)..(249)
<223> OTHER INFORMATION: Xaa can be Leu OR Gly OR Ile OR Val OR Ala
<220> FEATURE:
<221> NAME/KEY: VARIANT
<222> LOCATION: (250)..(250)
<223> OTHER INFORMATION: Xaa can be Glu OR Asp
```

```
<220> FEATURE:
<221> NAME/KEY: VARIANT
<222> LOCATION: (252)..(252)
<223> OTHER INFORMATION: Xaa can be Val OR Gly OR Ile OR Leu OR Ala
<220> FEATURE:
<221> NAME/KEY: VARIANT
<222> LOCATION: (253)..(253)
<223> OTHER INFORMATION: Xaa can be Glu OR Asp
<220> FEATURE:
<221> NAME/KEY: VARIANT
<222> LOCATION: (254)..(254)
<223> OTHER INFORMATION: Xaa can be Ala OR Gly OR Ile OR Val OR Leu
<220> FEATURE:
<221> NAME/KEY: VARIANT
<222> LOCATION: (255)..(255)
<223> OTHER INFORMATION: Xaa can be Leu OR Gly OR Ile OR Val OR Ala
<220> FEATURE:
<221> NAME/KEY: VARIANT
<222> LOCATION: (256)..(256)
<223> OTHER INFORMATION: Xaa can be Gly OR Leu OR Ile OR Val OR Ala
<220> FEATURE:
<221> NAME/KEY: VARIANT
<222> LOCATION: (257)..(257)
<223> OTHER INFORMATION: Xaa can be Glu OR Asp
<220> FEATURE:
<221> NAME/KEY: VARIANT
<222> LOCATION: (258)..(258)
<223> OTHER INFORMATION: Xaa can be Ile OR Gly OR Leu OR Val OR Ala
<220> FEATURE:
<221> NAME/KEY: VARIANT
<222> LOCATION: (259)..(259)
<223> OTHER INFORMATION: Xaa can be Glu OR Asp
<220> FEATURE:
<221> NAME/KEY: VARIANT
<222> LOCATION: (260)..(260)
<223> OTHER INFORMATION: Xaa can be Val OR Gly OR Ile OR Leu OR Ala
<220> FEATURE:
<221> NAME/KEY: VARIANT
<222> LOCATION: (261)..(261)
<223> OTHER INFORMATION: Xaa can be Ala OR Gly OR Ile OR Leu OR Val
<220> FEATURE:
<221> NAME/KEY: VARIANT
<222> LOCATION: (262)..(262)
<223> OTHER INFORMATION: Xaa can be Ser OR Thr
<220> FEATURE:
<221> NAME/KEY: VARIANT
<222> LOCATION: (263)..(263)
<223> OTHER INFORMATION: Xaa can be Lys OR Arg OR His
<220> FEATURE:
<221> NAME/KEY: VARIANT
<222> LOCATION: (264)..(264)
<223> OTHER INFORMATION: Xaa can be Leu OR Gly OR Ala OR Ile OR Val
<220> FEATURE:
<221> NAME/KEY: VARIANT
<222> LOCATION: (265)..(265)
<223> OTHER INFORMATION: Xaa can be Leu OR Gly OR Ala OR Ile OR Val
<220> FEATURE:
<221> NAME/KEY: VARIANT
<222> LOCATION: (267)..(267)
<223> OTHER INFORMATION: Xaa can be Asp OR Glu
<220> FEATURE:
<221> NAME/KEY: VARIANT
<222> LOCATION: (268)..(268)
<223> OTHER INFORMATION: Xaa can be Asp OR Glu
<220> FEATURE:
<221> NAME/KEY: VARIANT
<222> LOCATION: (269)..(269)
<223> OTHER INFORMATION: Xaa can be Ile OR Gly OR Leu OR Val OR Ala
<220> FEATURE:
<221> NAME/KEY: VARIANT
<222> LOCATION: (270)..(270)
<223> OTHER INFORMATION: Xaa can be Thr OR Ser
<220> FEATURE:
<221> NAME/KEY: VARIANT
<222> LOCATION: (272)..(272)
<223> OTHER INFORMATION: Xaa can be Glu OR Asp
<220> FEATURE:
<221> NAME/KEY: VARIANT
<222> LOCATION: (273)..(273)
<223> OTHER INFORMATION: Xaa can be Glu OR Asp
```

```
<220> FEATURE:
<221> NAME/KEY: VARIANT
<222> LOCATION: (274)..(274)
<223> OTHER INFORMATION: Xaa can be Arp OR Glu
<220> FEATURE:
<221> NAME/KEY: VARIANT
<222> LOCATION: (276)..(276)
<223> OTHER INFORMATION: Xaa can be Leu OR Gly OR Val OR Ile OR Ala
<220> FEATURE:
<221> NAME/KEY: VARIANT
<222> LOCATION: (277)..(277)
<223> OTHER INFORMATION: Xaa can be Tyr OR Phe OR Trp
<220> FEATURE:
<221> NAME/KEY: VARIANT
<222> LOCATION: (278)..(278)
<223> OTHER INFORMATION: Xaa can be Tyr OR Phe OR Trp
<220> FEATURE:
<221> NAME/KEY: VARIANT
<222> LOCATION: (279)..(279)
<223> OTHER INFORMATION: Xaa can be Arg OR Lys OR His
<220> FEATURE:
<221> NAME/KEY: VARIANT
<222> LOCATION: (280)..(280)
<223> OTHER INFORMATION: Xaa can be Tyr OR Phe OR Trp
<220> FEATURE:
<221> NAME/KEY: VARIANT
<222> LOCATION: (281)..(281)
<223> OTHER INFORMATION: Xaa can be Gln OR Asn
<220> FEATURE:
<221> NAME/KEY: VARIANT
<222> LOCATION: (282)..(282)
<223> OTHER INFORMATION: Xaa can be Gln OR Asn
<220> FEATURE:
<221> NAME/KEY: VARIANT
<222> LOCATION: (283)..(283)
<223> OTHER INFORMATION: Xaa can be Leu OR Gly OR Ile OR Val OR Ala
<220> FEATURE:
<221> NAME/KEY: VARIANT
<222> LOCATION: (284)..(284)
<223> OTHER INFORMATION: Xaa can be His OR Lys OR Arg
<220> FEATURE:
<221> NAME/KEY: VARIANT
<222> LOCATION: (286)..(286)
<223> OTHER INFORMATION: Xaa can be Glu OR Asp
<220> FEATURE:
<221> NAME/KEY: VARIANT
<222> LOCATION: (287)..(287)
<223> OTHER INFORMATION: Xaa can be Leu OR Gly OR Ile OR Val OR Ala
<220> FEATURE:
<221> NAME/KEY: VARIANT
<222> LOCATION: (288)..(288)
<223> OTHER INFORMATION: Xaa can be Phe OR Tyr OR Trp
<220> FEATURE:
<221> NAME/KEY: VARIANT
<222> LOCATION: (290)..(290)
<223> OTHER INFORMATION: Xaa can be Leu OR Gly OR Val OR Ile OR Ala
<220> FEATURE:
<221> NAME/KEY: VARIANT
<222> LOCATION: (291)..(291)
<223> OTHER INFORMATION: Xaa can be Asp OR Glu
<220> FEATURE:
<221> NAME/KEY: VARIANT
<222> LOCATION: (292)..(292)
<223> OTHER INFORMATION: Xaa can be Asn OR Gln
<220> FEATURE:
<221> NAME/KEY: VARIANT
<222> LOCATION: (293)..(293)
<223> OTHER INFORMATION: Xaa can be Asp OR Glu
<220> FEATURE:
<221> NAME/KEY: VARIANT
<222> LOCATION: (294)..(294)
<223> OTHER INFORMATION: Xaa can be Thr OR Ser
<220> FEATURE:
<221> NAME/KEY: VARIANT
<222> LOCATION: (295)..(295)
<223> OTHER INFORMATION: Xaa can be Glu OR Asp
<220> FEATURE:
<221> NAME/KEY: VARIANT
<222> LOCATION: (296)..(296)
<223> OTHER INFORMATION: Xaa can be Glu OR Asp
```

```
<220> FEATURE:
<221> NAME/KEY: VARIANT
<222> LOCATION: (297)..(297)
<223> OTHER INFORMATION: Xaa can be Phe OR Tyr OR Trp
<220> FEATURE:
<221> NAME/KEY: VARIANT
<222> LOCATION: (298)..(298)
<223> OTHER INFORMATION: Xaa can be Ala OR Gly OR Ile OR Val OR Leu
<220> FEATURE:
<221> NAME/KEY: VARIANT
<222> LOCATION: (299)..(299)
<223> OTHER INFORMATION: Xaa can be Leu OR Gly OR Ile OR Val OR Ala
<220> FEATURE:
<221> NAME/KEY: VARIANT
<222> LOCATION: (300)..(300)
<223> OTHER INFORMATION: Xaa can be Ile OR Gly OR Leu OR Val OR Ala
<220> FEATURE:
<221> NAME/KEY: VARIANT
<222> LOCATION: (301)..(301)
<223> OTHER INFORMATION: Xaa can be val OR Gly OR Leu OR Ile OR Ala
<220> FEATURE:
<221> NAME/KEY: VARIANT
<222> LOCATION: (302)..(302)
<223> OTHER INFORMATION: Xaa can be Lys OR Arg OR His
<220> FEATURE:
<221> NAME/KEY: VARIANT
<222> LOCATION: (303)..(303)
<223> OTHER INFORMATION: Xaa can be Tyr OR Phe OR Trp
<220> FEATURE:
<221> NAME/KEY: VARIANT
<222> LOCATION: (304)..(304)
<223> OTHER INFORMATION: Xaa can be Ile OR Gly OR Leu OR Val OR Ala
<220> FEATURE:
<221> NAME/KEY: VARIANT
<222> LOCATION: (305)..(305)
<223> OTHER INFORMATION: Xaa can be Gln OR Asn
<220> FEATURE:
<221> NAME/KEY: VARIANT
<222> LOCATION: (306)..(306)
<223> OTHER INFORMATION: Xaa can be Asn OR Gln
<220> FEATURE:
<221> NAME/KEY: VARIANT
<222> LOCATION: (307)..(307)
<223> OTHER INFORMATION: Xaa can be Thr OR Ser
<220> FEATURE:
<221> NAME/KEY: VARIANT
<222> LOCATION: (308)..(308)
<223> OTHER INFORMATION: Xaa can be His OR Arg OR Lys
<220> FEATURE:
<221> NAME/KEY: VARIANT
<222> LOCATION: (309)..(309)
<223> OTHER INFORMATION: Xaa can be Ala OR Gly OR Ile OR Val OR Leu
<220> FEATURE:
<221> NAME/KEY: VARIANT
<222> LOCATION: (310)..(310)
<223> OTHER INFORMATION: Xaa can be Gln OR Asn
<220> FEATURE:
<221> NAME/KEY: VARIANT
<222> LOCATION: (311)..(311)
<223> OTHER INFORMATION: Xaa can be Thr OR Ser
<220> FEATURE:
<221> NAME/KEY: VARIANT
<222> LOCATION: (312)..(312)
<223> OTHER INFORMATION: Xaa can be His OR Arg OR Lys
<220> FEATURE:
<221> NAME/KEY: VARIANT
<222> LOCATION: (313)..(313)
<223> OTHER INFORMATION: Xaa can be Ser OR Thr
<220> FEATURE:
<221> NAME/KEY: VARIANT
<222> LOCATION: (314)..(314)
<223> OTHER INFORMATION: Xaa can be Asn OR Gln
<220> FEATURE:
<221> NAME/KEY: VARIANT
<222> LOCATION: (315)..(315)
<223> OTHER INFORMATION: Xaa can be Tyr OR Phe OR Trp
<220> FEATURE:
<221> NAME/KEY: VARIANT
<222> LOCATION: (316)..(316)
<223> OTHER INFORMATION: Xaa can be Thr OR Ser
```

-continued

```
<220> FEATURE:
<221> NAME/KEY: VARIANT
<222> LOCATION: (317)..(317)
<223> OTHER INFORMATION: Xaa can be Val OR Gly OR Ile OR Leu OR Ala
<220> FEATURE:
<221> NAME/KEY: VARIANT
<222> LOCATION: (318)..(318)
<223> OTHER INFORMATION: Xaa can be Asp OR Glu
<220> FEATURE:
<221> NAME/KEY: VARIANT
<222> LOCATION: (319)..(319)
<223> OTHER INFORMATION: Xaa can be Val OR Gly OR Ile OR Leu OR Ala
<220> FEATURE:
<221> NAME/KEY: VARIANT
<222> LOCATION: (320)..(320)
<223> OTHER INFORMATION: Xaa can be Val OR Gly OR Ile OR Leu OR Ala
<220> FEATURE:
<221> NAME/KEY: VARIANT
<222> LOCATION: (321)..(321)
<223> OTHER INFORMATION: Xaa can be Gln OR Asn
<220> FEATURE:
<221> NAME/KEY: VARIANT
<222> LOCATION: (322)..(322)
<223> OTHER INFORMATION: Xaa can be Ile OR Gly OR Leu OR Val OR Ala
<220> FEATURE:
<221> NAME/KEY: VARIANT
<222> LOCATION: (323)..(323)
<223> OTHER INFORMATION: Xaa can be Phe OR Tyr OR Trp
<220> FEATURE:
<221> NAME/KEY: VARIANT
<222> LOCATION: (324)..(324)
<223> OTHER INFORMATION: Xaa can be Lys OR Arg OR His
<220> FEATURE:
<221> NAME/KEY: VARIANT
<222> LOCATION: (325)..(325)
<223> OTHER INFORMATION: Xaa can be Val OR Gly OR Ile OR Leu OR Ala
<220> FEATURE:
<221> NAME/KEY: VARIANT
<222> LOCATION: (326)..(326)
<223> OTHER INFORMATION: Xaa can be Thr OR Ser
<220> FEATURE:
<221> NAME/KEY: VARIANT
<222> LOCATION: (327)..(327)
<223> OTHER INFORMATION: Xaa can be Arg OR Lys OR His
<220> FEATURE:
<221> NAME/KEY: VARIANT
<222> LOCATION: (328)..(328)
<223> OTHER INFORMATION: Xaa can be Asp OR Glu
<220> FEATURE:
<221> NAME/KEY: VARIANT
<222> LOCATION: (329)..(329)
<223> OTHER INFORMATION: Xaa can be Gly OR Ala OR Val OR Ile OR Leu
<220> FEATURE:
<221> NAME/KEY: VARIANT
<222> LOCATION: (330)..(330)
<223> OTHER INFORMATION: Xaa can be Glu OR Asp
<220> FEATURE:
<221> NAME/KEY: VARIANT
<222> LOCATION: (331)..(331)
<223> OTHER INFORMATION: Xaa can be Ser OR Thr
<220> FEATURE:
<221> NAME/KEY: VARIANT
<222> LOCATION: (332)..(332)
<223> OTHER INFORMATION: Xaa can be Glu OR Asp
<220> FEATURE:
<221> NAME/KEY: VARIANT
<222> LOCATION: (333)..(333)
<223> OTHER INFORMATION: Xaa can be Arg OR Lys OR His
<220> FEATURE:
<221> NAME/KEY: VARIANT
<222> LOCATION: (334)..(334)
<223> OTHER INFORMATION: Xaa can be Phe OR Tyr OR Trp
<220> FEATURE:
<221> NAME/KEY: VARIANT
<222> LOCATION: (335)..(335)
<223> OTHER INFORMATION: Xaa can be Lys OR Arg OR His
<220> FEATURE:
<221> NAME/KEY: VARIANT
<222> LOCATION: (336)..(336)
<223> OTHER INFORMATION: Xaa can be Lys OR Arg OR His
```

```
<220> FEATURE:
<221> NAME/KEY: VARIANT
<222> LOCATION: (337)..(337)
<223> OTHER INFORMATION: Xaa can be Phe OR Tyr OR Trp
<220> FEATURE:
<221> NAME/KEY: VARIANT
<222> LOCATION: (338)..(338)
<223> OTHER INFORMATION: Xaa can be Ser OR Thr
<220> FEATURE:
<221> NAME/KEY: VARIANT
<222> LOCATION: (339)..(339)
<223> OTHER INFORMATION: Xaa can be Gly OR Val OR Ile OR Leu OR Ala
<220> FEATURE:
<221> NAME/KEY: VARIANT
<222> LOCATION: (340)..(340)
<223> OTHER INFORMATION: Xaa can be Thr OR Ser
<220> FEATURE:
<221> NAME/KEY: VARIANT
<222> LOCATION: (341)..(341)
<223> OTHER INFORMATION: Xaa can be Lys OR Arg OR His
<220> FEATURE:
<221> NAME/KEY: VARIANT
<222> LOCATION: (342)..(342)
<223> OTHER INFORMATION: Xaa can be Asn OR Gln
<220> FEATURE:
<221> NAME/KEY: VARIANT
<222> LOCATION: (343)..(343)
<223> OTHER INFORMATION: Xaa can be Arg OR Lys OR His
<220> FEATURE:
<221> NAME/KEY: VARIANT
<222> LOCATION: (345)..(345)
<223> OTHER INFORMATION: Xaa can be Leu OR Ile OR Gly OR Val OR Ala
<220> FEATURE:
<221> NAME/KEY: VARIANT
<222> LOCATION: (346)..(346)
<223> OTHER INFORMATION: Xaa can be Leu OR Ile OR Gly OR Val OR Ala
<220> FEATURE:
<221> NAME/KEY: VARIANT
<222> LOCATION: (347)..(347)
<223> OTHER INFORMATION: Xaa can be Trp OR Phe OR Tyr
<220> FEATURE:
<221> NAME/KEY: VARIANT
<222> LOCATION: (348)..(348)
<223> OTHER INFORMATION: Xaa can be His OR Arg OR Lys
<220> FEATURE:
<221> NAME/KEY: VARIANT
<222> LOCATION: (349)..(349)
<223> OTHER INFORMATION: Xaa can be Gly OR Ile OR Val OR Leu OR Ala
<220> FEATURE:
<221> NAME/KEY: VARIANT
<222> LOCATION: (350)..(350)
<223> OTHER INFORMATION: Xaa can be Ser OR Thr
<220> FEATURE:
<221> NAME/KEY: VARIANT
<222> LOCATION: (351)..(351)
<223> OTHER INFORMATION: Xaa can be Arg OR Lys OR His
<220> FEATURE:
<221> NAME/KEY: VARIANT
<222> LOCATION: (352)..(352)
<223> OTHER INFORMATION: Xaa can be Leu OR Gly OR Ile OR Val OR Ala
<220> FEATURE:
<221> NAME/KEY: VARIANT
<222> LOCATION: (353)..(353)
<223> OTHER INFORMATION: Xaa can be Thr OR Ser
<220> FEATURE:
<221> NAME/KEY: VARIANT
<222> LOCATION: (354)..(354)
<223> OTHER INFORMATION: Xaa can be Asn OR Gln
<220> FEATURE:
<221> NAME/KEY: VARIANT
<222> LOCATION: (355)..(355)
<223> OTHER INFORMATION: Xaa can be Trp OR Phe OR Tyr
<220> FEATURE:
<221> NAME/KEY: VARIANT
<222> LOCATION: (356)..(356)
<223> OTHER INFORMATION: Xaa can be Thr OR Ser
<220> FEATURE:
<221> NAME/KEY: VARIANT
<222> LOCATION: (357)..(357)
<223> OTHER INFORMATION: Xaa can be Gly OR Ile OR Ala OR Leu OR Val
```

```
<220> FEATURE:
<221> NAME/KEY: VARIANT
<222> LOCATION: (358)..(358)
<223> OTHER INFORMATION: Xaa can be Ile OR Gly OR Ala OR Leu OR Val
<220> FEATURE:
<221> NAME/KEY: VARIANT
<222> LOCATION: (359)..(359)
<223> OTHER INFORMATION: Xaa can be Leu OR Gly OR Ala OR Ile OR Val
<220> FEATURE:
<221> NAME/KEY: VARIANT
<222> LOCATION: (360)..(360)
<223> OTHER INFORMATION: Xaa can be Ser OR Thr
<220> FEATURE:
<221> NAME/KEY: VARIANT
<222> LOCATION: (361)..(361)
<223> OTHER INFORMATION: Xaa can be Gln OR Asn
<220> FEATURE:
<221> NAME/KEY: VARIANT
<222> LOCATION: (362)..(362)
<223> OTHER INFORMATION: Xaa can be Gly OR Ile OR Val OR Leu OR Ala
<220> FEATURE:
<221> NAME/KEY: VARIANT
<222> LOCATION: (363)..(363)
<223> OTHER INFORMATION: Xaa can be Leu OR Ile OR Val OR Gly OR Ala
<220> FEATURE:
<221> NAME/KEY: VARIANT
<222> LOCATION: (364)..(364)
<223> OTHER INFORMATION: Xaa can be Arg OR Lys OR His
<220> FEATURE:
<221> NAME/KEY: VARIANT
<222> LOCATION: (365)..(365)
<223> OTHER INFORMATION: Xaa can be Ile OR Leu OR Gly OR Val OR Ala
<220> FEATURE:
<221> NAME/KEY: VARIANT
<222> LOCATION: (366)..(366)
<223> OTHER INFORMATION: Xaa can be Ala OR Leu OR Gly OR Val OR Ile
<220> FEATURE:
<221> NAME/KEY: VARIANT
<222> LOCATION: (369)..(369)
<223> OTHER INFORMATION: Xaa can be Glu OR Asp
<220> FEATURE:
<221> NAME/KEY: VARIANT
<222> LOCATION: (370)..(370)
<223> OTHER INFORMATION: Xaa can be Ala OR Gly OR Val OR Ile OR Leu
<220> FEATURE:
<221> NAME/KEY: VARIANT
<222> LOCATION: (372)..(372)
<223> OTHER INFORMATION: Xaa can be Ala OR Gly OR Val OR Ile OR Leu
<220> FEATURE:
<221> NAME/KEY: VARIANT
<222> LOCATION: (381)..(381)
<223> OTHER INFORMATION: Xaa can be Val OR Gly OR Ala OR Ile OR Leu
<220> FEATURE:
<221> NAME/KEY: VARIANT
<222> LOCATION: (382)..(382)
<223> OTHER INFORMATION: Xaa can be Tyr OR Phe OR Trp
<220> FEATURE:
<221> NAME/KEY: VARIANT
<222> LOCATION: (383)..(383)
<223> OTHER INFORMATION: Xaa can be Phe OR Tyr OR Trp
<220> FEATURE:
<221> NAME/KEY: VARIANT
<222> LOCATION: (384)..(384)
<223> OTHER INFORMATION: Xaa can be Ala OR Gly OR Ile OR Val OR Leu
<220> FEATURE:
<221> NAME/KEY: VARIANT
<222> LOCATION: (385)..(385)
<223> OTHER INFORMATION: Xaa can be Asp OR Glu
<220> FEATURE:
<221> NAME/KEY: VARIANT
<222> LOCATION: (387)..(387)
<223> OTHER INFORMATION: Xaa can be Phe OR Tyr OR Trp
<220> FEATURE:
<221> NAME/KEY: VARIANT
<222> LOCATION: (388)..(388)
<223> OTHER INFORMATION: Xaa can be Ser OR Thr
<220> FEATURE:
<221> NAME/KEY: VARIANT
<222> LOCATION: (389)..(389)
<223> OTHER INFORMATION: Xaa can be Lys OR Arg OR His
```

```
-continued

<220> FEATURE:
<221> NAME/KEY: VARIANT
<222> LOCATION: (390)..(390)
<223> OTHER INFORMATION: Xaa can be Ser OR Thr
<220> FEATURE:
<221> NAME/KEY: VARIANT
<222> LOCATION: (391)..(391)
<223> OTHER INFORMATION: Xaa can be Ala OR Gly OR Val OR Ile OR Leu
<220> FEATURE:
<221> NAME/KEY: VARIANT
<222> LOCATION: (392)..(392)
<223> OTHER INFORMATION: Xaa can be Asn OR Gln
<220> FEATURE:
<221> NAME/KEY: VARIANT
<222> LOCATION: (393)..(393)
<223> OTHER INFORMATION: Xaa can be Tyr OR Phe OR Trp
<220> FEATURE:
<221> NAME/KEY: VARIANT
<222> LOCATION: (395)..(395)
<223> OTHER INFORMATION: Xaa can be Tyr OR Phe OR Trp
<220> FEATURE:
<221> NAME/KEY: VARIANT
<222> LOCATION: (396)..(396)
<223> OTHER INFORMATION: Xaa can be Thr OR Ser
<220> FEATURE:
<221> NAME/KEY: VARIANT
<222> LOCATION: (397)..(397)
<223> OTHER INFORMATION: Xaa can be Asn OR Gln
<220> FEATURE:
<221> NAME/KEY: VARIANT
<222> LOCATION: (398)..(398)
<223> OTHER INFORMATION: Xaa can be Ser OR Thr
<220> FEATURE:
<221> NAME/KEY: VARIANT
<222> LOCATION: (399)..(399)
<223> OTHER INFORMATION: Xaa can be Ala OR Gly OR Val OR Ile OR Leu
<220> FEATURE:
<221> NAME/KEY: VARIANT
<222> LOCATION: (400)..(400)
<223> OTHER INFORMATION: Xaa can be Phe OR Tyr OR Trp
<220> FEATURE:
<221> NAME/KEY: VARIANT
<222> LOCATION: (401)..(401)
<223> OTHER INFORMATION: Xaa can be Thr OR Ser
<220> FEATURE:
<221> NAME/KEY: VARIANT
<222> LOCATION: (402)..(402)
<223> OTHER INFORMATION: Xaa can be Thr OR Ser
<220> FEATURE:
<221> NAME/KEY: VARIANT
<222> LOCATION: (403)..(403)
<223> OTHER INFORMATION: Xaa can be Gly OR Ala OR Ile OR Leu OR Val
<220> FEATURE:
<221> NAME/KEY: VARIANT
<222> LOCATION: (404)..(404)
<223> OTHER INFORMATION: Xaa can be Val OR Ala OR Ile OR Leu OR Gly
<220> FEATURE:
<221> NAME/KEY: VARIANT
<222> LOCATION: (405)..(405)
<223> OTHER INFORMATION: Xaa can be Leu OR Ala OR Ile OR Val OR Gly
<220> FEATURE:
<221> NAME/KEY: VARIANT
<222> LOCATION: (406)..(406)
<223> OTHER INFORMATION: Xaa can be Leu OR Ala OR Ile OR Val OR Gly
<220> FEATURE:
<221> NAME/KEY: VARIANT
<222> LOCATION: (407)..(407)
<223> OTHER INFORMATION: Xaa can be Leu OR Ala OR Ile OR Val OR Gly
<220> FEATURE:
<221> NAME/KEY: VARIANT
<222> LOCATION: (409)..(409)
<223> OTHER INFORMATION: Xaa can be Glu OR Asp
<220> FEATURE:
<221> NAME/KEY: VARIANT
<222> LOCATION: (410)..(410)
<223> OTHER INFORMATION: Xaa can be Val OR Ala OR Gly OR Ile OR Leu
<220> FEATURE:
<221> NAME/KEY: VARIANT
<222> LOCATION: (411)..(411)
<223> OTHER INFORMATION: Xaa can be Ala OR Val OR Gly OR Ile OR Leu
```

```
<220> FEATURE:
<221> NAME/KEY: VARIANT
<222> LOCATION: (412)..(412)
<223> OTHER INFORMATION: Xaa can be Leu OR Val OR Gly OR Ile OR Ala
<220> FEATURE:
<221> NAME/KEY: VARIANT
<222> LOCATION: (413)..(413)
<223> OTHER INFORMATION: Xaa can be Gly OR Val OR Leu OR Ile OR Ala
<220> FEATURE:
<221> NAME/KEY: VARIANT
<222> LOCATION: (414)..(414)
<223> OTHER INFORMATION: Xaa can be Asp OR Glu
<220> FEATURE:
<221> NAME/KEY: VARIANT
<222> LOCATION: (416)..(416)
<223> OTHER INFORMATION: Xaa can be Ala OR Gly OR Val OR Ile OR Leu
<220> FEATURE:
<221> NAME/KEY: VARIANT
<222> LOCATION: (417)..(417)
<223> OTHER INFORMATION: Xaa can be Glu OR Asp
<220> FEATURE:
<221> NAME/KEY: VARIANT
<222> LOCATION: (418)..(418)
<223> OTHER INFORMATION: Xaa can be Leu OR Gly OR Val OR Ile OR Ala
<220> FEATURE:
<221> NAME/KEY: VARIANT
<222> LOCATION: (419)..(419)
<223> OTHER INFORMATION: Xaa can be Leu OR Gly OR Val OR Ile OR Ala
<220> FEATURE:
<221> NAME/KEY: VARIANT
<222> LOCATION: (420)..(420)
<223> OTHER INFORMATION: Xaa can be Gln OR Asn
<220> FEATURE:
<221> NAME/KEY: VARIANT
<222> LOCATION: (421)..(421)
<223> OTHER INFORMATION: Xaa can be Ala OR Gly OR Ile OR Leu OR Val
<220> FEATURE:
<221> NAME/KEY: VARIANT
<222> LOCATION: (422)..(422)
<223> OTHER INFORMATION: Xaa can be Lys OR Arg OR His
<220> FEATURE:
<221> NAME/KEY: VARIANT
<222> LOCATION: (423)..(423)
<223> OTHER INFORMATION: Xaa can be Ser OR Thr
<220> FEATURE:
<221> NAME/KEY: VARIANT
<222> LOCATION: (424)..(424)
<223> OTHER INFORMATION: Xaa can be Asp OR Glu
<220> FEATURE:
<221> NAME/KEY: VARIANT
<222> LOCATION: (425)..(425)
<223> OTHER INFORMATION: Xaa can be Ala OR Gly OR Ile OR Val OR Leu
<220> FEATURE:
<221> NAME/KEY: VARIANT
<222> LOCATION: (426)..(426)
<223> OTHER INFORMATION: Xaa can be Asp OR Glu
<220> FEATURE:
<221> NAME/KEY: VARIANT
<222> LOCATION: (427)..(427)
<223> OTHER INFORMATION: Xaa can be Lys OR Arg OR His
<220> FEATURE:
<221> NAME/KEY: VARIANT
<222> LOCATION: (428)..(428)
<223> OTHER INFORMATION: Xaa can be Leu OR Gly OR Ala OR Ile OR Val
<220> FEATURE:
<221> NAME/KEY: VARIANT
<222> LOCATION: (430)..(430)
<223> OTHER INFORMATION: Xaa can be Asp OR Glu
<220> FEATURE:
<221> NAME/KEY: VARIANT
<222> LOCATION: (431)..(431)
<223> OTHER INFORMATION: Xaa can be Gly OR Val OR Ile OR Ala OR Leu
<220> FEATURE:
<221> NAME/KEY: VARIANT
<222> LOCATION: (432)..(432)
<223> OTHER INFORMATION: Xaa can be Lys OR Arg OR His
<220> FEATURE:
<221> NAME/KEY: VARIANT
<222> LOCATION: (433)..(433)
<223> OTHER INFORMATION: Xaa can be Leu OR Gly OR Ile OR Ala OR Val
```

```
<220> FEATURE:
<221> NAME/KEY: VARIANT
<222> LOCATION: (434)..(434)
<223> OTHER INFORMATION: Xaa can be Ser OR Thr
<220> FEATURE:
<221> NAME/KEY: VARIANT
<222> LOCATION: (435)..(435)
<223> OTHER INFORMATION: Xaa can be Thr OR Ser
<220> FEATURE:
<221> NAME/KEY: VARIANT
<222> LOCATION: (436)..(436)
<223> OTHER INFORMATION: Xaa can be Lys OR Arg OR His
<220> FEATURE:
<221> NAME/KEY: VARIANT
<222> LOCATION: (437)..(437)
<223> OTHER INFORMATION: Xaa can be Gly OR Ala OR Ile OR Leu OR Val
<220> FEATURE:
<221> NAME/KEY: VARIANT
<222> LOCATION: (438)..(438)
<223> OTHER INFORMATION: Xaa can be Val OR Ala OR Ile OR Leu OR Gly
<220> FEATURE:
<221> NAME/KEY: VARIANT
<222> LOCATION: (439)..(439)
<223> OTHER INFORMATION: Xaa can be Gly OR Ala OR Ile OR Leu OR Val
<220> FEATURE:
<221> NAME/KEY: VARIANT
<222> LOCATION: (440)..(440)
<223> OTHER INFORMATION: Xaa can be Ala OR Gly OR Ile OR Leu OR Val
<220> FEATURE:
<221> NAME/KEY: VARIANT
<222> LOCATION: (441)..(441)
<223> OTHER INFORMATION: Xaa can be Thr OR Ser
<220> FEATURE:
<221> NAME/KEY: VARIANT
<222> LOCATION: (442)..(442)
<223> OTHER INFORMATION: Xaa can be Ala OR Gly OR Ile OR Val OR Leu
<220> FEATURE:
<221> NAME/KEY: VARIANT
<222> LOCATION: (444)..(444)
<223> OTHER INFORMATION: Xaa can be Asp OR Glu
<220> FEATURE:
<221> NAME/KEY: VARIANT
<222> LOCATION: (446)..(446)
<223> OTHER INFORMATION: Xaa can be Ser OR Thr
<220> FEATURE:
<221> NAME/KEY: VARIANT
<222> LOCATION: (447)..(447)
<223> OTHER INFORMATION: Xaa can be Glu OR Asp
<220> FEATURE:
<221> NAME/KEY: VARIANT
<222> LOCATION: (448)..(448)
<223> OTHER INFORMATION: Xaa can be Ala OR Gly OR Ile OR Val OR Leu
<220> FEATURE:
<221> NAME/KEY: VARIANT
<222> LOCATION: (449)..(449)
<223> OTHER INFORMATION: Xaa can be Gln OR Asn
<220> FEATURE:
<221> NAME/KEY: VARIANT
<222> LOCATION: (450)..(450)
<223> OTHER INFORMATION: Xaa can be Ser OR Thr
<220> FEATURE:
<221> NAME/KEY: VARIANT
<222> LOCATION: (451)..(451)
<223> OTHER INFORMATION: Xaa can be Leu OR Gly OR Ile OR Leu OR Val
<220> FEATURE:
<221> NAME/KEY: VARIANT
<222> LOCATION: (452)..(452)
<223> OTHER INFORMATION: Xaa can be Asp OR Glu
<220> FEATURE:
<221> NAME/KEY: VARIANT
<222> LOCATION: (453)..(453)
<223> OTHER INFORMATION: Xaa can be Asp OR Glu
<220> FEATURE:
<221> NAME/KEY: VARIANT
<222> LOCATION: (454)..(454)
<223> OTHER INFORMATION: Xaa can be Gly OR Ala OR Ile OR Leu OR Val
<220> FEATURE:
<221> NAME/KEY: VARIANT
<222> LOCATION: (455)..(455)
<223> OTHER INFORMATION: Xaa can be Val OR Ala OR Ile OR Leu OR Gly
```

```
<220> FEATURE:
<221> NAME/KEY: VARIANT
<222> LOCATION: (456)..(456)
<223> OTHER INFORMATION: Xaa can be Val OR Ala OR Ile OR Leu OR Gly
<220> FEATURE:
<221> NAME/KEY: VARIANT
<222> LOCATION: (457)..(457)
<223> OTHER INFORMATION: Xaa can be Val OR Ala OR Ile OR Leu OR Gly

<400> SEQUENCE: 15

Xaa Xaa Xaa Xaa Xaa Xaa Xaa Xaa Xaa Xaa Xaa Xaa Xaa Xaa Pro Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Met Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Met Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Gly Pro Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa Xaa
            100                 105                 110

Cys Xaa Pro Xaa Cys Xaa Xaa Xaa Xaa Xaa Met Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Cys Xaa Xaa Xaa Met Met Xaa Xaa Met Met Xaa Xaa Xaa Xaa
            165                 170                 175

Xaa Xaa Xaa Xaa Xaa Pro Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Xaa Xaa Xaa Xaa
            210                 215                 220

Xaa Pro Xaa Xaa Xaa Xaa Xaa Xaa Met Xaa Xaa Xaa Xaa Xaa Xaa Xaa
225                 230                 235                 240

Xaa Pro Xaa Xaa Xaa Xaa Xaa Xaa Xaa Met Xaa Xaa Xaa Xaa Xaa Xaa
            245                 250                 255

Xaa Xaa Xaa Xaa Xaa Xaa Xaa Xaa Met Xaa Xaa Xaa Xaa Xaa Met Xaa
            260                 265                 270

Xaa Xaa Pro Xaa Xaa Xaa Xaa Xaa Xaa Xaa Xaa Xaa Cys Xaa Xaa Xaa
            275                 280                 285

Pro Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Met Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Pro Pro
            355                 360                 365
```

```
Xaa Xaa Pro Xaa Thr Gly Tyr Met Phe Gly Lys Gly Xaa Xaa Xaa Xaa
    370                 375                 380

Xaa Met Xaa Xaa Xaa Xaa Xaa Xaa Cys Xaa Xaa Xaa Xaa Xaa Xaa Xaa
385                 390                 395                 400

Xaa Xaa Xaa Xaa Xaa Xaa Xaa Cys Xaa Xaa Xaa Xaa Xaa Xaa Met Xaa
                405                 410                 415

Xaa Xaa Xaa Xaa Xaa Xaa Xaa Xaa Xaa Xaa Xaa Pro Xaa Xaa Xaa
            420                 425                 430

Xaa Xaa Xaa Xaa Xaa Xaa Xaa Xaa Xaa Pro Xaa Pro Xaa Xaa Xaa
        435                 440                 445

Xaa Xaa Xaa Xaa Xaa Xaa Xaa Xaa Xaa
    450                 455
```

```
<210> SEQ ID NO 16
<211> LENGTH: 20
<212> TYPE: DNA
<213> ORGANISM: Artificial Sequence
<220> FEATURE:
<223> OTHER INFORMATION: Oligonucleotide 1 for cDNA probe

<400> SEQUENCE: 16
aagccctggg agaaatagag                                              20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide 2 for cDNA probe

<400> SEQUENCE: 17
cagttagtaa gccgagaacc                                              20

<210> SEQ ID NO 18
<211> LENGTH: 307
<212> TYPE: DNA
<213> ORGANISM: Artificial Sequence
<220> FEATURE:
<223> OTHER INFORMATION: cDNA probe

<400> SEQUENCE: 18
aagccctggg agaaatagag gtcgcatcaa aattattaat ggatgacatt acgatggagg    60
aagatccttt atattatcgg taccaacagc ttcactgtga actgtttcct cttgacaatg   120
atactgagga gttcgctttg attgtaaagt atattcagaa tactcatgct cagacacatt   180
caaattatac agttgatgtt gttcaaatat tcaaggtgac aagagacggt gaaagtgaac   240
gctttaaaaa gttttctgga acaaaaaata gaatgctgtt gtggcatggt tctcggctta   300
ctaactg                                                            307

<210> SEQ ID NO 19
<211> LENGTH: 8837
<212> TYPE: DNA
<213> ORGANISM: Gossypium hirsutum
<220> FEATURE:
<221> NAME/KEY: misc_feature
<222> LOCATION: (1380)..(1383)
<223> OTHER INFORMATION: exon
<220> FEATURE:
<221> NAME/KEY: misc_feature
<222> LOCATION: (1470)..(1563)
<223> OTHER INFORMATION: exon
<220> FEATURE:
<221> NAME/KEY: misc_feature
<222> LOCATION: (1606)..(1786)
```

```
<223> OTHER INFORMATION: exon
<220> FEATURE:
<221> NAME/KEY: misc_feature
<222> LOCATION: (1868)..(2150)
<223> OTHER INFORMATION: exon
<220> FEATURE:
<221> NAME/KEY: misc_feature
<222> LOCATION: (2243)..(2385)
<223> OTHER INFORMATION: exon
<220> FEATURE:
<221> NAME/KEY: misc_feature
<222> LOCATION: (2531)..(2612)
<223> OTHER INFORMATION: exon
<220> FEATURE:
<221> NAME/KEY: misc_feature
<222> LOCATION: (2799)..(3034)
<223> OTHER INFORMATION: exon
<220> FEATURE:
<221> NAME/KEY: misc_feature
<222> LOCATION: (3226)..(3352)
<223> OTHER INFORMATION: exon
<220> FEATURE:
<221> NAME/KEY: misc_feature
<222> LOCATION: (3519)..(3574)
<223> OTHER INFORMATION: exon
<220> FEATURE:
<221> NAME/KEY: misc_feature
<222> LOCATION: (4044)..(4117)
<223> OTHER INFORMATION: exon
<220> FEATURE:
<221> NAME/KEY: misc_feature
<222> LOCATION: (4258)..(4432)
<223> OTHER INFORMATION: exon
<220> FEATURE:
<221> NAME/KEY: misc_feature
<222> LOCATION: (4598)..(4660)
<223> OTHER INFORMATION: exon
<220> FEATURE:
<221> NAME/KEY: misc_feature
<222> LOCATION: (5244)..(5324)
<223> OTHER INFORMATION: exon
<220> FEATURE:
<221> NAME/KEY: misc_feature
<222> LOCATION: (5517)..(5627)
<223> OTHER INFORMATION: exon
<220> FEATURE:
<221> NAME/KEY: misc_feature
<222> LOCATION: (5726)..(5801)
<223> OTHER INFORMATION: exon
<220> FEATURE:
<221> NAME/KEY: misc_feature
<222> LOCATION: (6027)..(6202)
<223> OTHER INFORMATION: exon
<220> FEATURE:
<221> NAME/KEY: misc_feature
<222> LOCATION: (6547)..(6620)
<223> OTHER INFORMATION: exon
<220> FEATURE:
<221> NAME/KEY: misc_feature
<222> LOCATION: (6848)..(6950)
<223> OTHER INFORMATION: exon
<220> FEATURE:
<221> NAME/KEY: misc_feature
<222> LOCATION: (7048)..(7140)
<223> OTHER INFORMATION: exon
<220> FEATURE:
<221> NAME/KEY: polyA_site
<222> LOCATION: (353)..(7353)

<400> SEQUENCE: 19 aactttgtc atcataagaa atttctgtca cttaaattta aaattttgtt cacttttca      60 ttaaatcatt aacggaatat tggcataacc ttttttatta acataataac aaatttaact   120
ctccaaaatt tataaattat atcaaattag ttttaatttt aaaaaattca aaaaatttaa   180
cccttaactt tacatgctct atcaatctag tctcaattct taaatattaa aaattaatta   240
aaagttaatt tttttataaa aaatatatac aagattatat aaatatagat ttttctcgtt   300
```

```
ttataatatg acatttattt attaaaataa taatattaaa aataaaacaa cttggggaaa    360
gcaaccatga agaagactta agcaaattca aattttctgt cttcttcttc aacattaaca    420
accactatgc tttaggttgt tgcctaaaac gagtttgttg tgtttgaggt tgtgcttgaa    480
gacgggtgtg attggagaag aataggtgag aaaggccgaa gaaaaagaaa ttcttttggg    540
agggaggtag aattaagtta taaattttga taagagttaa aatgcaattt cattattgta    600
ttagatatat aatatattta taattttttaa aaaactaaat taaaacttta tcactttggg   660
agacaaagtc aattttatca ttattaattt ataatttta aagggtaagc aaaacaattt     720
tccaatttta aggattgccc ccttcgtgcc accttcgtag gcgaggatga gatattggaa    780
acccaatagg tggaaggtca tgttggtagc tccacaattg attcatttttt tttaatggca   840
caatgataaa gaatgtgaaa attgaagagt ttggagtaag ggttattggt gccaatagtt    900
gtgggtgaag gcaatgccta gcgttcagta aagtcaacga agactaagga attaagctat    960
cggtataata aataagttat tatttataaa ataaaactag aaaaaaatga aaagcttgga   1020
actgatttaa gtattgtttg tgagtgtttt tagatatcaa tcaataaatt tcatgttaga   1080
aaaagagaaa aataagtatt catttatata tatttatgta ttttttataat tttatatgta   1140
tttttatcga aaaataaact tttaaatgtt ttttttttatt ttttaaagtt ttttgaattt   1200
ttaatttta ataccaaga ttaaattaac agaatgcgta aagttgagag ttaaatttgt     1260
taaattttta agaattagga ccaaattgat agtatgccaa acacgaatga gctacttaat   1320
aaaaaactcg cagaaaccaa aagcatgttg atctaaatgg agctaaaagt cttaaaatca   1380
tgagtaagtt caagggcctt tctttaactc taattagttt ccggtaatt gctgcaagtc    1440
ccaacgggct ttctcttatg ggcacacagg attcggccct atatttggaa ggagtgcttg   1500
gcacggtttt actcttaacg cgaacgagga cgaagtcggt agtgggcagg gcccagaaga   1560
ggcgccaatg gcgatatcgt ggtgggaaag gttctaaaac gacagcgttt tgaagcacat   1620
ttgtcgccgt attaatgtgt atccctccat ttccttctta cattctcaaa cgatttctcc   1680
cgcactttgc tcatcgaaga acatggcaag gaagctgaaa gtaggccagc tccgagacga   1740
actcgcccag cgtgggcttg acacaatcgg gaccaagccc ttactggttg cccaatctac   1800
tttttactct tttatctgc ccctttgttc tttgttcatt tttactgata tgagctgttt    1860
ataacaggtg ctgagactgg aggatgcttt gctcaaggag aggaagaaag aagaggaaaa   1920
tggaggcaag gctaataatg caatcggaaa taacaagaga aaaagaggga gggaatcgga   1980
tgtctgtaat aacgaggatt cggacaaagt caatgccgtt gaggagtttc gacaaatgaa   2040
tgtcaagcaa ttacgcgaac aagctactct tcgacgtctt tccactgttg gcaccaaaaa   2100
ggaacttctc gagaggcttt gtgaagatgc cgacaagaat cctcttcctg gtaagatgat   2160
tttcggtttt attggttcat tttgttggtt agttccattt atgaaagact gaaaggggtt   2220
tctttatttg ttgcgtgggt agttaaagaa gaagaagaag aagaggaaga agaagaagaa   2280
gaagagaagg aaagtagcaa ggaggagaaa atcgttacgg ccacaaagaa aggggtggct   2340
gttctggatc aagggatccc agatgacata aaggctcatt atcatgttct acaaaaggct   2400
agtctttgct gtttgaattc cattttttga gcctgtcatt ttgaaaaata ttttgcctgc   2460
ctgctatatt ctttgttaga atatacattt ccagaacaga agaattaata ttttaatttc   2520
tgtgattcag ggtgatgata tctatgatgc catgttaaat cagacgaatg ttgggcaaaa   2580
caataacaaa ttctttgtga tccagcttct aggttagttc ttcgttataa tgttatgcgt   2640
tttatcccca ctggttttca aatttattgc tttaagtatc tttctcttcc aatttcattt   2700
```

```
gtatagacct atgcacttcc tttttgggga gttttttggg ggggggggat atttgctagt   2760
tctactttga aaatgatttc cttattattt tctcacagaa tctgatgact cgaagacata   2820
catggttcat aacagatggg gtagagttgg tgtgaagggt caaattaagt tacatggccc   2880
ctttacttca cgacaagccg caattgatga gtttcaaacc aaattcttta acaagaccaa   2940
aaactattgg tacaacagaa aagactttgt ttgtcaccca aagtgctaca ccttgctgga   3000
gatggactat gatgaaaaag aaaaggaatc tgatgtgagt tattttaaca cataaacaga   3060
tgacttactg gctcctctac cttctcccac tgtcctcctc tttctaattt gccttaatgt   3120
ttatgaagca caatatttgc ttgcctaaaa tcatgtaatc tatgctagtc ttggagcttt   3180
aattgcctgt tgaatttctt ctgacttctt aattattata ttcaggtcaa aagaaaggct   3240
aactcttcca ttggtgctca attgcgggag acaaagcttg aacaacgtgt tgctaagttt   3300
atctctatta tatgcaatat cagcatgatg aagcaacaaa tgatggaaat aggttagtta   3360
gtttacaatt gttacctgaa ctatttatat acatgagaga tgtctggttc aattttttaag  3420 ccatgtttgc ttcatttggt tttctaaagc cttgtaaaat cctttttatt atattcttgc   3480
ctgctaatat ttcctataaa tgttgtggtt gtctttagga tacaatgctg acaagttgcc   3540
tcttggtaag ctaagcaaat ccacaatttt aaaggtgatt tttcaagaca tgcacaaaac   3600
atttcttttt gaaatctttt gtggttagaa aatataagag acttcagaag gtaaaaaagt   3660
attccacttt ggtgattatt tacatgctag gtatacccttt ctaaactaat tttaaatatt   3720
gacggtctag tctggtcatt gtgtcagtga gtgtaagctg ctttgaactt tttgagcgtt   3780
cagattactt ctttaatctg ccccttaatc tacgtttgga gttgagtacc cctttccat   3840 ccattatggt cccgaacttc ctgctatgct ttgtcttacg atggtttctt gatatcgatc   3900
ttattgcaga tgtctttgtt tcacagtgct tctgcatgct tgttttctca agcctgcagt   3960
aactacaaca ttggcattac atttgttaat tagtatcttt ttttattgaa ataaaaatat   4020
taattatgct tggatatgtt caggggtatg atgtcttaaa gaaaattgct gatgtgattg   4080
accagtcaaa caggagcaag cttgagcaat taagttcgta agaactttaa gttttatcca   4140
acttttgtta gatatgcata atagtaaatg cttatgata ttgggtttat gtttattttc    4200
cgtgaactct tcatgttgaa atgtgaatat cattcgtttt tttctttta attacaggga    4260 attttacacc gtgattccac atgatttgg atttagaaaa atgcgtgagt cttcttcttc    4320
atctcctcct ctaaccatac ccaataacaa tattacaact gacacagaac tatatgtggc   4380
aggtgatttt gtcatcgaca cacctcagaa gttgaaaaag aagttggaaa tggtgatata   4440
tacctaacta ccctctattg ttttaactat ttgcccttgc agcttttagt aacatcaagt   4500
attgttttca tacctgagca tttttacaag tttgtgccaa cttttttagt tgtttccttc    4560
aataagggca atctcagttc ctcttatgta attgaaggtt gaagccctgg gagaaataga   4620
ggtcgcatca aaattattaa tggatgacat tacgatggag gtattttact cctgttctgt   4680
gatgctcttt tctacattct tcccccattt taaatctccc atttcagtga accctttaaa    4740
taagctgaac cgtaagttga tttttaaact actaaaagtt tttgcatgcc taacaagcat   4800
tgcatgcagg acataattgt atttttgctag ccaattgaca atattgtttt cttcatatgc   4860
atcatacata aatagtggat aaagttgagt ttgttgtaga gcttattttt catttatgag   4920
tgctgtattt gtatgacctg taaaccatat ggcctgcagg ctacaaccat gttctatcaa   4980
catttgaact gttgtagttc ttttttttagc caactgctaa aaaatttata caatcgttgt   5040
attatagtga gcttaatttg ggtattagtt aattttagca cccaaatttc ttctatctct   5100
```

```
aatttcttt   gttatactga  tgtgtccata  tatgcataca  tacacaaata  ttgttgagat   5160
gtttatgttt  ttcctgttct  ttctcattag  gttatgtatg  ctctaaaatt  tttctctaac   5220
ttaattttgt  gcggaatgtt  taggaagatc  ctttatatta  tcggtaccaa  cagcttcact   5280
gtgaactgtt  tcctcttgac  aatgatactg  aggagttcgc  tatggtattt  gttcatcttt   5340
gtagcactag  aaatttgaat  tcaaaataaa  acttaagcaa  tttgtaacta  tctgcttttct  5400 ttttggggcc  ctcttccaat  tttgaaaaaa  aattaaattt  gcagaatagt  ttagcaatgc   5460
attttggaaa  ctagcttgtt  tacattttct  ctgttcttt   ttcttccccg  gatcagattg   5520
taaagtatat  tcagaatact  catgctcaga  cacattcaaa  ttatacagtt  gatgttgttc   5580
aaatattcgc  ggtgagaaga  gacggtgaaa  gtgaacgctt  taaaaaggtg  cctctcatga   5640
aatattattt  ccatgttacc  tgtagaatgt  ccgttctacc  aagtgattag  tattggtcta   5700
actttatggt  ttcttacctg  agcagttttc  tggaacaaaa  aatagaatgc  tgttgtggca   5760
tggttctcgg  cttactaact  ggactggcat  tctgtcccaa  ggtctatcct  tttctctttt   5820
gtttctaaat  gtagttatgt  atggagattt  gtgggtagca  tgtgtttcct  attttctcct   5880
gtttctggat  cttgggattg  gcattctgta  tcaaggtcct  tccttttctc  tgtcgttttg   5940
catgttgtcc  aggatgtttg  agtgggatgt  ggaatgtgtt  tgtcaataac  cacatctaac   6000
tgtatcttgt  acttatcatc  catcaggttt  gcgcattgct  ccacctgaag  cgcctgccac   6060
gggttacatg  tttgggaagg  gggtttactt  tgctgatatg  ttctccaaaa  gtgcaaatta   6120
ttgctatact  aattctgcct  tcacgactgg  ggtgttgctt  ctatgtgagg  tagttcttca   6180
atcagttcaa  atgatatttt  tggtaataac  ctggaatata  atgatggttc  caccataaac   6240
cgtgttaaat  tattgtgtca  agtttatgca  tttttatcag  aaattacaat  ccgagtattt   6300
ccttatcaca  gcgactagtt  aaccagatac  tctttgtatc  agtggttcaa  actgattaat   6360
tttcactcag  cgaaaattag  tttcctatca  tgatctcatt  attttgatgc  tgtgcatttg   6420
aattttcttg  gaaatcagaa  attgactgct  tgctacctgt  ttctgcatgt  ctgctttccc   6480
ttgtccttct  gtgtattata  atcattcctt  tggcttatat  ctcataagac  atatatctct   6540
ttttaggttg  ccctgggaga  catggctgag  cttctacaag  ctaaaagcga  tgctgataag   6600
ctgccggatg  ggaagttgag  gtttgtaaat  tttaactaaa  caaattgctt  ataaataact   6660
ggcatatatg  tgtttctaat  aacttaggac  tttccaaatg  cacaactaaa  aaccatgagg   6720
agctttttcc  tgcgtcatgc  catttagagt  ctccctgttta tattgtacca  tttgtgagca   6780
acatcgacat  tagttctgtc  cttctcttt   taaaacatgt  taatatgaca  ttgattctgt   6840
attgcagcac  aaagggtgtt  ggtgcaactg  cactggatcc  ctctgaagcc  cagtcacttg   6900
atgatggtgt  tgtagttccc  ctaggaaaac  caaaggagca  aaaacggaag  gtaagattaa   6960
gaaatttatt  catggaaatc  aatcattttt  tctgaaacta  ataaaatatc  ttatgtttgc   7020
tatatgcatt  tggaatttcc  tttgcagggt  gctttattat  acaatgaata  tgtagtctac   7080
aatgtcgacc  agataaggat  gcgctacttg  attcaagtta  gtttcaaata  tacaaagtag   7140
tagtccgcac  atttgttgat  ttactgcctg  gttttgatag  aattttgatc  tgtaatctat   7200
atgttgtaaa  tgtatgaaac  atatttgcat  ttgctctgta  gcccgtgtat  gataccaggc   7260 agggggacttg tttcatacgt  tttagacaaa  atgaacccca  ttccttttc   ttctctgaaa   7320 ttcgaaatcc  cataggcgta  gtcttagatt  tgaataaatt  tgttattatc  attatcttgg   7380
atttaaatta  ttttgaaata  gtattttga   attagtaact  cgtttatttt  ctataaatag   7440
aggttcctat  caacaataaa  ttaaaggctt  cctttgactt  caatataaac  aacattctgt   7500
```

```
tttggtttca aactgatatt agattgttca aattccattc ttggtgtgtt ttggttaact    7560
tatatcggtt ggtgtaagat tattgtttta aatcaacatt ttctttttct ttttatttaa    7620
ttaatatata taaaatagaa aacatttata agtaccaatt ttaaaacaaa accacatact    7680
cattagatta tttatgaagt gctgattttt tttccaatgc tttcataata tgtttatatc    7740
tcattttaga tgatggcata gcatgaccga tagtcaaact gaaatgatag ggctatacat    7800
acgtcggccg ttatttttaa tagctgtttc tttgttgttg gaagcaaagt caaatatatg    7860
catcaatcaa agcatggaga acttttactt atagcttgtt ggaaattttt tgagtgtatg    7920
accaagtaag gcatttacta caatacccac gacacaacac gctagctagc atttatgtct    7980
ctaaattaga ttttgatgat ggcttctgct cagaatctat gttcttccac cacacaaaat    8040
tggtgttatt aatgggtgac accactgtct gcaatttatt ttagatggac tttcaactgt    8100
gcttgtgtgt acatatagtt ttcttagata aacagagctt ttgagcttca gttttaacta    8160
ttttgtctac tgaaagtcga ttttaagtta attcaggata tcgtattagt gataaatttt    8220
attgatttat tgaaaggaag gggatggaat aagtggtttt tgagaagata tgcgacttgg    8280
tgttttactt gttcgatatg ccatcagtct tacaactctg agtatttgga cacttttttgc    8340 tcctttcttt tgatgttagc acgatttggt aaatgattat gattttcttt ctcttctttt    8400
tcaaaccttg cgaccatagc tttggtttgc ttacatgcac taaatccctg tcatgtatga    8460
cataaggcca tcaaaattgc agggaatccg gatttagttt aaatggttgg tcgatatata    8520
tataaaaaaa agctggtgcc tacatttaca caacagtgaa tcatatcaac ctagggaggc    8580
ccccttcctc acatgctcat tgatacaaaa cactcgaaag cttgcacgtt tgaacccaac    8640
acgcaaagcc tacgtctact tccactgtta cgttattctc ttctgcttct tccaccaaca    8700
caacacaact ggttgaggtt cttcagcctc aagcaagcac acatcatata gaataaataa    8760
ataaatgggc ccataccata aatggtggtg ggacctgata tcatggcacg agattcttga    8820
tccaatggta gccagcc                                                   8837
```

```
<210> SEQ ID NO 20
<211> LENGTH: 8124
<212> TYPE: DNA
<213> ORGANISM: Gossypium hirsutum
<220> FEATURE:
<221> NAME/KEY: misc_feature
<222> LOCATION: (1384)..(1384)
<223> OTHER INFORMATION: transcription start site
<220> FEATURE:
<221> NAME/KEY: misc_feature
<222> LOCATION: (1458)..(1541)
<223> OTHER INFORMATION: exon
<220> FEATURE:
<221> NAME/KEY: misc_feature
<222> LOCATION: (1625)..(1907)
<223> OTHER INFORMATION: exon
<220> FEATURE:
<221> NAME/KEY: misc_feature
<222> LOCATION: (2000)..(2377)
<223> OTHER INFORMATION: exon
<220> FEATURE:
<221> NAME/KEY: misc_feature
<222> LOCATION: (2560)..(2795)
<223> OTHER INFORMATION: exon
<220> FEATURE:
<221> NAME/KEY: misc_feature
<222> LOCATION: (3027)..(3153)
<223> OTHER INFORMATION: exon
<220> FEATURE:
<221> NAME/KEY: misc_feature
<222> LOCATION: (3321)..(3376)
<223> OTHER INFORMATION: exon
```

```
<220> FEATURE:
<221> NAME/KEY: misc_feature
<222> LOCATION: (3840)..(3913)
<223> OTHER INFORMATION: exon
<220> FEATURE:
<221> NAME/KEY: misc_feature
<222> LOCATION: (4053)..(4227)
<223> OTHER INFORMATION: exon
<220> FEATURE:
<221> NAME/KEY: misc_feature
<222> LOCATION: (4392)..(4454)
<223> OTHER INFORMATION: exon
<220> FEATURE:
<221> NAME/KEY: misc_feature
<222> LOCATION: (5044)..(5124)
<223> OTHER INFORMATION: exon
<220> FEATURE:
<221> NAME/KEY: misc_feature
<222> LOCATION: (5317)..(5427)
<223> OTHER INFORMATION: exon
<220> FEATURE:
<221> NAME/KEY: misc_feature
<222> LOCATION: (5526)..(5601)
<223> OTHER INFORMATION: exon
<220> FEATURE:
<221> NAME/KEY: misc_feature
<222> LOCATION: (5812)..(5954)
<223> OTHER INFORMATION: exon
<220> FEATURE:
<221> NAME/KEY: misc_feature
<222> LOCATION: (6332)..(6405)
<223> OTHER INFORMATION: exon
<220> FEATURE:
<221> NAME/KEY: misc_feature
<222> LOCATION: (6633)..(6735)
<223> OTHER INFORMATION: exon
<220> FEATURE:
<221> NAME/KEY: misc_feature
<222> LOCATION: (6833)..(6925)
<223> OTHER INFORMATION: exon
<220> FEATURE:
<221> NAME/KEY: polyA_site
<222> LOCATION: (7138)..(7138)

<400> SEQUENCE: 20
aaccaaaagc atgttgatcc aaatggagtc taaaagcctt aaaatcatga ataagttcaa      60 gggccttct  taaactttaa ttagtcttcc gggaatttgc tgcaagtctc aacgggcttt     120
ctcttttggg cacacaggat tcggccctat atttggaagg agtgcttggc acggttttac     180
tcttaacgca aacgaggacg aagtcagtag tgggcaggga attattggtt ttttaaccgc     240
tctggttgtt tcacaaaaat taaatctaaa aaataatttt aaaaaataat ttattttct     300 aaaaaagtta atatttgtta gtgtttagat taatttgtgt aaaatatttt ctgttgtttg     360
gtagatttct taaaatatt  tcataaaatt attttaatt  aaataaactt acatttgaaa     420
ttttcttatt ttttcatta  tttaattaaa tttattttta tctataattt tatattttat     480 attgttttg  tatatattaa aaatattatg ttaaatttaa attcattaca acatcatttt     540
ttaattacat gactactaac tgagtatttt ttttaaaaat gtgacatcaa caaaattgat     600
aaaaaaatta acgatgtcaa caattggatt tgattttaa  atttaaaaag taaagggact     660
aaattcttga aaataaaagt acaaagacta aattacaaat atgtgaagtg tacatagact     720
tatgacatat tttaacctt  atactacaaa atatttatta ttaatatatt tataattata     780
ataaatattt attattaaaa tattaatata gaatattttc aataatatgt gaataatatt     840
atttaaaatt attatttta  aaatttatta ttaaaataaa attgaaatat taaataattt     900
attaaaataa taattatat  ttattatatt ataatttat  tatatgactta aatataaata    960 attaaatacg tatgtttaat aatattaaaa aaacataata ttttaaatat ttttaaaaat    1020
```

```
aaaaataaaa attattatta atataataat attaaacttg atttaaatta attttttatat      1080 aaaaataaaa ttatatatag ataaatttttt ttttctgaaa atgacttgca cttttttaaaa     1140 gagtaagtca ttttacaaaa aaaaaattgt tttatcttaa tctataaatt attttctatt      1200
gattaaacta ttttttatga aacaaatata aaaaaatata aaaaatattt tctgtaaaat      1260 attttttcata aaactttata gataaatgga ccctaagcga aacaattccg gaagaggctg     1320
caatggcaat atcgtgctgg gaaagctact aaaacgacag cgttttgaag cacatttgtc     1380
accgtataaa aatgtatccc tccatttcct tcttacattc tcaaacgatt tctcccacac     1440
tttgctcatc gaagaacatg gcaagtaagc tgaaagcagg ccagctccga gacgaactcg     1500
cccagcgtgg gcttgacaca atcgggacca agcccttact ggttgcccaa tctgctttt     1560 actcttttta tctgcccctt tgttctttgt tcattttat tgatatgagt tgtttatata      1620
acaggtgctg agactggagg atgctttgct caaggagagg aagaaagaag aggaaaatgg     1680
aggcaaggct aacaatgcaa tcggaaataa caagagaaaa agagggaggg agtcggatgt    1740
ctgtagtaac gaggattcgg acaaagtcaa tgccgttgag gagtttcgac aaatgaatgt    1800
caagcaatta cgcgaacaag ctactcttcg aggccttttcc actgttggca ccaaaaagga   1860
acttctcgag cggctttgtg aagatgccga caagaatcct cttcctggta agatgatttt   1920 cagtttatt ggttcatttt gttggttagt tccatttgtg aaagactgaa aggggtttct    1980
ttatttgttg cgtgggtagt taaagtagaa gaagaagaag aagaagaaga agaagaagaa    2040
gaagaagaag agaaggaaag taggaaggag gagaaaatcg ttacggccac aaagaaaggg    2100
gtggctgttc tggatcaagg gatcccagat gagataaagg ctcattatca tgttctacaa    2160
aaggctagtc tttgttgttt gaattccatt tttgagcctg tcattttgaa aaatattttg    2220
cctgcctgct ttattctttg ttacaatata catttacaga acagaagaat taatatttta    2280
agttctgtga ttcagggtga tcatatctat gatgccatgt taaatcagac gaatgttggg    2340
caaaacaata acaagttctt tgtgatccag cttctaggtt agttcttcgt tataatgtta    2400
tgcgttttct ccccactggt tttcaaattt attgctttaa gtatcttct cttccaattt     2460 catttgtatg gacctatgca cttccttttt ggggagtttt tagggtggga tatttgctag    2520
ttctactttg ataatgattt ccttattatt ttctcacaga atctgatgac tcaaagacat    2580
acatggttca taatagatgg ggtagagttg gtgtgaaggg tcaaattaag ttacatggcc    2640
cctttacttc acgacaagct gcaattgatg tgtttcaaac caagttcttt aacaagacca    2700
aaaactattg gtacaacaga aaagactttg tttgtcaccc aaagtgctac accttgctgg    2760
agatggacta tgatgaaaaa gaaaaggatt ctgatgtgag ttattttaac acataaacag    2820
atgacttact gactcctcta ccttctccca ctgccctcct ctttctgatt tgccttaatg    2880
tttatgaagc acaatatttg cttgcctaaa atcatgtttta aggaaatgag aagaatggga   2940
gagaaggagc atcatataat ctatgctagt cttggagctt taattgcctg ttgaatttct    3000
tctgacttct taattattat attcaggtca aaagaaaggc taactcttcc attggtgctc    3060
aattgcggga gacaaagctt gaacaacgtg ttgctaagtt tatctctgtt atatgcaata    3120
tcagcatgat gaagcaacaa atgatggaaa taggttagtt agcttacaat tgttacctga    3180
actatttata tacatgagag atgtctggtt caattttaa gccatgtttg cttcatttgg    3240
ttttctaaag ccttgtaaaa tcctttttat ttatattctt gcctgctaat atttcctata    3300
aatgttgtgg ttgtctttag gatacaatgc tgacaagttg cctcttggta agctaagcaa    3360
atccacaatt ttaaaggtga ttttttcaaga catgcacaaa acatttcttt ttgaaatctt    3420
```

-continued

```
ttgtggttag aaaatataag agactacaga aggtaaaaaa gtattccact ttggtgatta    3480
tttacatgct aggtatacct ttctaaacta attttaaata ttgaaggtct agtccggtca    3540
ttgtgtcagt gagtgtaagc agctttgaac ttttttgagcg ttcagattac ttctttaatc   3600
tgccccttaa tctacgtttg gagttgagta cccctttttcc atccattatg gtcccgaact   3660
tcctgctatg ctttgtctta tgatgatttc ttgatatcga tcttattgcg gatgtctttg    3720
tttcacggtg cttctgcgtg cttgttttct caagcctgca gtaacattgg cattacattt    3780
gttagttagt atctttttttt attgaaaata aaatattaat tatgcttgga tatgttcagg   3840
ggtatgatat cttaaagaaa attgctgatg tgattgacca gtcaaacagg agcaagcttg    3900
agcaattaag ttcgtaagaa ctttaagttt tttccaactt ttgttagata tgcataatag    3960
taaatgcttt atgatattgg gtttatgttt attttccgtg aactcttcat gttgaaatgt    4020
gaatatcatt cgttttatct tttcaattac agggaatttt acaccgtgat ccacatgat    4080 tttggattta gaaaaatgcg tgagtcttct tcttcatctc ctcctctaac catacccaat    4140
aacaatatta caactgacgc agaactatat gtggcaggtg attttgtcat cgacaaacct   4200
cagaagttga aaagaagtt ggaaatggtg atttatacct aactaccctc tattgtttta    4260
actatctgcc cttgcagctt ttagtaacat caagtattat tttcatgcct gagcatttta    4320
caagtttgtg ccaactttt tagttgtttc cttcaataag ggcaatctca gttcctctta    4380
tgtaattgaa ggttgaagcc ctgggagaaa tagaggtcgc atcaaaatta ttaatggatg   4440
acattacgat ggaggtattt tactcctgtt cggtgatgct cttttctaca ttcttccccc    4500
tttttaaatc tcccatttca gtgaacccctt taaataagct gaaccgtaag ttgagttta    4560 aactactaaa agttttgca tgcctaacaa acattgcatg caggacataa ttgtatttg     4620 ctagccaatt gacaatattg ttttcttcat atgcatcata cataaatatt gtggataaag   4680
ttgagtctgt tgtagagctt attttcatt tatgagtgct gtatttgtat gacttgtaaa    4740
ccatatggcc tgcaggctac aactatgttc tatcaacatt tgaactgtta tagttctttc   4800 ttttttagt caactgctaa aaaaattata caatcgttgt attatagtga gcttaatttg    4860
agcattagtt aattttagca cccaaatttc ttctatctct aatttctttt gttatactga   4920
tgtgtccata tatgcataca tacacaaata ttgttgagat gtttatgttt ttcctgttct   4980
ttctcattag gttatgtatg ctctaaaatt ttcctctaac ttaattttgt gcggaatgtt   5040
taggaagatc ctttatatta tcggtaccag cagcttcact gtgaactgtt tcctcttgac    5100
aatgatactg aggagttcgc tttggtattt gttcatcttt gtagcactag aaatttgaat   5160
ttaacataaa acttaagcaa tttgtaacta tctgctttct ttttggtgcc ctcttccaaa   5220
tttgaaaaaa aaaaaaaatt gcagaatagt ttagcaatgc attttggaaa ctagcttgtt   5280
tacattttct ctgttctttt ttcttccccg gatcagattg taaagtatat tcagaatact   5340
catgctcaga cacattcaaa ttatacagtt gatgttgttc aaatattcaa ggtgacaaga   5400
gacggtgaaa gtgaacgctt taaaaggtg cctctcatga atattattt ccatgttaac    5460 tgtagaatgt cctttctacc aagtgattag tattggtcta actttatggc ttcttacctg   5520
agcagttttc tggaacaaaa aatagaatgc tgttgtggca tggttctcgg cttactaact   5580
ggactggcat tctgtcccaa ggtctatcct tttctctttt gtttctaaat gttgttatgt   5640
atggagattt gtttcctatt ttctcccgtt tctggttctt gcgattggca ttctgtatca   5700
aggtccttcc ttttctctgt tgttttgcat gttgtccagg atgtttgagt gggatgtgga   5760
atgtgtttgt caataaccac atctaactgt atcgtactta tcatccatca ggtttgcgca   5820
```

```
ttgctccacc tgaagcgcct gccacgggtt atatgtttgg gaaggggtt tactttgctg      5880
atatgttctc caaaagtgca aattattgct atactaattc tgccttcaca actggggtgt      5940
tgcttctatg tgaggtagtt cttcaatcag ttcaaattat attttggtaa taacctggaa      6000
tataatgatg gttccaccat aaactgtgtt aaattattgt gtgaagttta tgcattttta      6060
tcagaaatta caatccgaga atttccttat cacagcgact agttaaccag atactctttg      6120
tatcagtggt tcaaactgat tcattttcac tcagcgaaaa ttagtttcct atcatgatct      6180
cattattttg atgctgtgca tttgaatttt cttggaattc agaaattgac tgcttgctac      6240
ctgtttctgc acgtctgctt tcccttgtcc ttctgtgtat tataatcatt cctttggctt      6300
agtatctcat aagacatata tctctttta ggttgccctg ggtgacatgg ctgagcttct      6360
acaagctaaa agcgatgctg ataagctgcc ggatgggaag ttgaggtttg taaattttaa      6420
ctaaacagat tgcttataaa taactggcat atatgtgttt ctaataactt aggactttcc      6480
aaatgcacaa ctaaaaaccg tgaggagctt tttcctgcct tatgccattt agagtctcct      6540
gtttatattg taccatttgt gagcaacatc gacattagtt ctgtcctcct cttttaaaa      6600
catgttaata tgacattgat tctgtattgc agcacaaaag gtgttggtgc aactgcaccg      6660
gatccttctg aagcccagtc acttgatgat ggtgttgtag ttcccctagg aaaaccgaag      6720
gagcaaaacc ggaaggtaag attaagaaat ttattcatgg aaatcaatca ttttttctga      6780
aactaataaa atatcttatg tttgttatat gcatttgaaa tttcctttgc agggtgcttt      6840
attatacaat gaatatatag tctacaatgt cgaccagata aggatgcgct acttgattca      6900
agttagtttc aaatatacaa agtagttgtc cgcacatttg ttgatttact gcctggtttt      6960
gatagaattt tgatctgtaa tctatatgtt gtaaatgtat gaaacatatt tgcatttgct      7020
ctgtagcccg tgtatgatac caggcagggg acttgtttca tacgttttag acaaaatgaa      7080
ccccattcct ttttcttctc tgaaattcga aatcctatag gcgtagtctt agatttgaat      7140
aaatttgcta ttatcattat cttagattta aattattttg aaatagtatt tttaaattag      7200
taactcgttt tatttctata atagaggttc ctatcaacaa taaattaaag gcttcctttg      7260
acttcaatat aaacaacatt ctgttttggt ttcacactga tattagattg ttcaaattcc      7320
attcttggtg tgttttggtt atatcggttg gtataagatt atagttttaa atcaacattt      7380
tcttttatt tttatttaa ttaatatata taaaatagaa aacatttatg agtaccaatt      7440
tcaaaacaaa accacatact cattagatta tttattaagt tctgatttt tttccaatgc      7500
tttcaaaata tgtttatatt tcattttagg tgatggcata gcatgaccga tagtcaaact      7560
gaaatgatag ggctatacat acgtcggccg ttaggtttaa tagctgtttc tttgttgttg      7620
gaagcgaagt caaatatatg catcaatcaa agcatggaga acttttactc atagcttgtt      7680
ggaaattttt tgagtgtatg accaattaag gcatttacta caatacccac gacacaacac      7740
gctagctagc atttatgtct ctaaattaga ttttgatgat ggcttctgct cagaatctat      7800
gttcttccac tacacaaatt tggtgttatt aatgggtgac accactgtct gcaatttatt      7860
ttagatggac tttcaactat gcttgtgtgt acatatagtt ttcttagata aacagagctt      7920
ttgagcttca gttttaacta ctttgtctac tgaaagtcga ttttaagtta attcaggata      7980
tcgtattagt gataaatttt atttatttat taaaggaag gggatgaaat aagaggtttt      8040
tgagaagaca tgcgacttgg tgttttactt gttcaatatg ccatcagtct tacaactctc      8100
gagtatttgg acacttttg ctcc                                              8124
```

<210> SEQ ID NO 21

```
<211> LENGTH: 743
<212> TYPE: PRT
<213> ORGANISM: Gossypium hirsutum

<400> SEQUENCE: 21

Met Arg Phe Gly Pro Ile Phe Gly Arg Ser Ala Trp His Gly Phe Thr
1               5                   10                  15

Leu Asn Ala Asn Glu Asp Glu Val Gly Ser Gly Gln Gly Pro Glu Glu
            20                  25                  30

Ala Val Leu Lys His Ile Cys Arg Arg Ile Asn Val Tyr Pro Ser Ile
        35                  40                  45

Ser Phe Leu His Ser Gln Thr Ile Ser Pro Ala Leu Cys Ser Ser Lys
    50                  55                  60

Asn Met Ala Arg Lys Leu Lys Val Gly Gln Leu Arg Asp Glu Leu Ala
65                  70                  75                  80

Gln Arg Gly Leu Asp Thr Ile Gly Thr Lys Pro Leu Leu Val Leu Arg
                85                  90                  95

Leu Glu Asp Ala Leu Leu Lys Glu Arg Lys Lys Glu Glu Glu Asn Gly
            100                 105                 110

Gly Lys Ala Asn Asn Ala Ile Gly Asn Asn Lys Arg Lys Arg Gly Arg
        115                 120                 125

Glu Ser Asp Val Cys Asn Asn Glu Asp Ser Asp Lys Val Asn Ala Val
    130                 135                 140

Glu Glu Phe Arg Gln Met Asn Val Lys Gln Leu Arg Glu Gln Ala Thr
145                 150                 155                 160

Leu Arg Arg Leu Ser Thr Val Gly Thr Lys Lys Glu Leu Leu Glu Arg
                165                 170                 175

Leu Cys Glu Asp Ala Asp Lys Asn Pro Leu Pro Val Lys Glu Glu Glu
            180                 185                 190

Glu Glu Glu Glu Glu Glu Glu Glu Lys Glu Ser Ser Lys Glu
        195                 200                 205

Glu Lys Ile Val Thr Ala Thr Lys Lys Gly Val Ala Val Leu Asp Gln
    210                 215                 220

Gly Ile Pro Asp Asp Ile Lys Ala His Tyr His Gly Asp Asp Ile Tyr
225                 230                 235                 240

Asp Ala Met Leu Asn Gln Thr Asn Val Gly Gln Asn Asn Lys Phe
                245                 250                 255

Phe Val Ile Gln Leu Leu Glu Ser Asp Asp Ser Lys Thr Tyr Met Val
            260                 265                 270

His Asn Arg Trp Gly Arg Val Gly Val Lys Gly Gln Ile Lys Leu His
        275                 280                 285

Gly Pro Phe Thr Ser Arg Gln Ala Ala Ile Asp Glu Phe Gln Thr Lys
    290                 295                 300

Phe Phe Asn Lys Thr Lys Asn Tyr Trp Tyr Asn Arg Lys Asp Phe Val
305                 310                 315                 320

Cys His Pro Lys Cys Tyr Thr Leu Leu Glu Met Asp Tyr Asp Glu Lys
                325                 330                 335

Glu Lys Glu Ser Asp Val Lys Arg Lys Ala Asn Ser Ser Ile Gly Ala
            340                 345                 350

Gln Leu Arg Glu Thr Lys Leu Glu Gln Arg Val Ala Lys Phe Ile Ser
        355                 360                 365

Ile Ile Cys Asn Ile Ser Met Met Lys Gln Gln Met Met Glu Ile Gly
    370                 375                 380

Tyr Asn Ala Asp Lys Leu Pro Leu Gly Lys Leu Ser Lys Ser Thr Ile
385                 390                 395                 400
```

```
Leu Lys Gly Tyr Asp Val Leu Lys Lys Ile Ala Asp Val Ile Asp Gln
            405                 410                 415

Ser Asn Arg Ser Lys Leu Glu Gln Leu Ser Ser Glu Phe Tyr Thr Val
            420                 425                 430

Ile Pro His Asp Phe Gly Phe Arg Lys Met Arg Glu Ser Ser Ser Ser
            435                 440                 445

Ser Pro Pro Leu Thr Ile Pro Asn Asn Asn Ile Thr Thr Asp Thr Glu
            450                 455                 460

Leu Tyr Val Ala Gly Asp Phe Val Ile Asp Thr Pro Gln Lys Leu Lys
465                 470                 475                 480

Lys Lys Leu Glu Met Val Glu Ala Leu Gly Ile Glu Val Ala Ser
                485                 490                 495

Lys Leu Leu Met Asp Asp Ile Thr Met Glu Glu Asp Pro Leu Tyr Tyr
            500                 505                 510

Arg Tyr Gln Gln Leu His Cys Glu Leu Phe Pro Leu Asp Asn Asp Thr
            515                 520                 525

Glu Glu Phe Ala Met Ile Val Lys Tyr Ile Gln Asn Thr His Ala Gln
            530                 535                 540

Thr His Ser Asn Tyr Thr Val Asp Val Val Gln Ile Phe Ala Val Arg
545                 550                 555                 560

Arg Asp Gly Glu Ser Glu Arg Phe Lys Lys Phe Ser Gly Thr Lys Asn
            565                 570                 575

Arg Met Leu Leu Trp His Gly Ser Arg Leu Thr Asn Trp Thr Gly Ile
            580                 585                 590

Leu Ser Gln Gly Leu Arg Ile Ala Pro Pro Glu Ala Pro Ala Thr Gly
            595                 600                 605

Tyr Met Phe Gly Lys Gly Val Tyr Phe Ala Asp Met Phe Ser Lys Ser
            610                 615                 620

Ala Asn Tyr Cys Tyr Thr Asn Ser Ala Phe Thr Thr Gly Val Leu Leu
625                 630                 635                 640

Leu Cys Glu Val Val Leu Gln Ser Val Gln Met Ile Phe Leu Val Ala
            645                 650                 655

Leu Gly Asp Met Ala Glu Leu Leu Gln Ala Lys Ser Asp Ala Asp Lys
            660                 665                 670

Leu Pro Asp Gly Lys Leu Ser Thr Lys Gly Val Gly Ala Thr Ala Leu
            675                 680                 685

Asp Pro Ser Glu Ala Gln Ser Leu Asp Asp Gly Val Val Pro Leu
            690                 695                 700

Gly Lys Pro Lys Glu Gln Lys Arg Lys Gly Ala Leu Leu Tyr Asn Glu
705                 710                 715                 720

Tyr Val Val Tyr Asn Val Asp Gln Ile Arg Met Arg Tyr Leu Ile Gln
            725                 730                 735

Val Ser Phe Lys Tyr Thr Lys
            740

<210> SEQ ID NO 22
<211> LENGTH: 718
<212> TYPE: PRT
<213> ORGANISM: Gossypium hirsutum

<400> SEQUENCE: 22

Met Ala Ser Lys Leu Lys Ala Gly Gln Leu Arg Asp Glu Leu Ala Gln
1               5                   10                  15

Arg Gly Leu Asp Thr Ile Gly Thr Lys Pro Leu Leu Val Leu Arg Leu
            20                  25                  30
```

-continued

```
Glu Asp Ala Leu Leu Lys Glu Arg Lys Lys Glu Glu Asn Gly Gly
         35                  40                  45
Lys Ala Asn Asn Ala Ile Gly Asn Asn Lys Arg Lys Arg Gly Arg Glu
 50                  55                  60
Ser Asp Val Cys Ser Asn Glu Asp Ser Asp Lys Val Asn Ala Val Glu
 65                  70                  75                  80
Glu Phe Arg Gln Met Asn Val Lys Gln Leu Arg Glu Gln Ala Thr Leu
             85                  90                  95
Arg Gly Leu Ser Thr Val Gly Thr Lys Lys Glu Leu Leu Glu Arg Leu
            100                 105                 110
Cys Glu Asp Ala Asp Lys Asn Pro Leu Pro Val Lys Val Glu Glu Glu
            115                 120                 125
Glu Glu Glu Glu Glu Glu Glu Glu Glu Glu Glu Lys Glu Ser Arg
            130                 135                 140
Lys Glu Glu Lys Ile Val Thr Ala Thr Lys Lys Gly Val Ala Val Leu
145                 150                 155                 160
Asp Gln Gly Ile Pro Asp Glu Ile Lys Ala His Tyr His Val Leu Gln
                165                 170                 175
Lys Ala Ser Leu Cys Cys Leu Asn Ser Ile Phe Glu Pro Val Ile Leu
                180                 185                 190
Lys Asn Ile Leu Pro Ala Cys Phe Ile Leu Cys Tyr Asn Ile His Leu
                195                 200                 205
Gln Asn Arg Arg Ile Asn Ile Leu Ser Ser Val Ile Gln Gly Asp His
                210                 215                 220
Ile Tyr Asp Ala Met Leu Asn Gln Thr Asn Val Gly Gln Asn Asn Asn
225                 230                 235                 240
Lys Phe Phe Val Ile Gln Leu Leu Glu Ser Asp Ser Lys Thr Tyr
                245                 250                 255
Met Val His Asn Arg Trp Gly Arg Val Gly Val Lys Gly Gln Ile Lys
                260                 265                 270
Leu His Gly Pro Phe Thr Ser Arg Gln Ala Ala Ile Asp Val Phe Gln
                275                 280                 285
Thr Lys Phe Phe Asn Lys Thr Lys Asn Tyr Trp Tyr Asn Arg Lys Asp
                290                 295                 300
Phe Val Cys His Pro Lys Cys Tyr Thr Leu Leu Glu Met Asp Tyr Asp
305                 310                 315                 320
Glu Lys Glu Lys Asp Ser Asp Val Lys Arg Lys Ala Asn Ser Ser Ile
                325                 330                 335
Gly Ala Gln Leu Arg Glu Thr Lys Leu Glu Gln Arg Val Ala Lys Phe
                340                 345                 350
Ile Ser Val Ile Cys Asn Ile Ser Met Met Lys Gln Gln Met Met Glu
                355                 360                 365
Ile Gly Tyr Asn Ala Asp Lys Leu Pro Leu Gly Lys Leu Ser Lys Ser
                370                 375                 380
Thr Ile Leu Lys Gly Tyr Asp Ile Leu Lys Lys Ile Ala Asp Val Ile
385                 390                 395                 400
Asp Gln Ser Asn Arg Ser Lys Leu Glu Gln Leu Ser Ser Glu Phe Tyr
                405                 410                 415
Thr Val Ile Pro His Asp Phe Gly Phe Arg Lys Met Arg Glu Ser Ser
                420                 425                 430
Ser Ser Ser Pro Pro Leu Thr Ile Pro Asn Asn Asn Ile Thr Thr Asp
                435                 440                 445
Ala Glu Leu Tyr Val Ala Gly Asp Phe Val Ile Asp Lys Pro Gln Lys
```

```
                450            455            460
Leu Lys Lys Lys Leu Glu Met Val Glu Ala Leu Gly Glu Ile Glu Val
465                 470                 475                 480

Ala Ser Lys Leu Leu Met Asp Asp Ile Thr Met Glu Glu Asp Pro Leu
                485                 490                 495

Tyr Tyr Arg Tyr Gln Gln Leu His Cys Glu Leu Phe Pro Leu Asp Asn
            500                 505                 510

Asp Thr Glu Glu Phe Ala Leu Ile Val Lys Tyr Ile Gln Asn Thr His
        515                 520                 525

Ala Gln Thr His Ser Asn Tyr Thr Val Asp Val Gln Ile Phe Lys
    530                 535                 540

Val Thr Arg Asp Gly Glu Ser Glu Arg Phe Lys Lys Phe Ser Gly Thr
545                 550                 555                 560

Lys Asn Arg Met Leu Leu Trp His Gly Ser Arg Leu Thr Asn Trp Thr
                565                 570                 575

Gly Ile Leu Ser Gln Gly Leu Arg Ile Ala Pro Pro Glu Ala Pro Ala
            580                 585                 590

Thr Gly Tyr Met Phe Gly Lys Gly Val Tyr Phe Ala Asp Met Phe Ser
        595                 600                 605

Lys Ser Ala Asn Tyr Cys Tyr Thr Asn Ser Ala Phe Thr Thr Gly Val
    610                 615                 620

Leu Leu Leu Cys Glu Val Ala Leu Gly Asp Met Ala Glu Leu Leu Gln
625                 630                 635                 640

Ala Lys Ser Asp Ala Asp Lys Leu Pro Asp Gly Lys Leu Ser Thr Lys
                645                 650                 655

Gly Val Gly Ala Thr Ala Pro Asp Pro Ser Glu Ala Gln Ser Leu Asp
            660                 665                 670

Asp Gly Val Val Val Pro Leu Gly Lys Pro Lys Glu Gln Asn Arg Lys
        675                 680                 685

Gly Ala Leu Leu Tyr Asn Glu Tyr Ile Val Tyr Asn Val Asp Gln Ile
    690                 695                 700

Arg Met Arg Tyr Leu Ile Gln Val Ser Phe Lys Tyr Thr Lys
705                 710                 715

<210> SEQ ID NO 23
<211> LENGTH: 2232
<212> TYPE: DNA
<213> ORGANISM: Gossypium hirsutum

<400> SEQUENCE: 23
atgagattcg gccctatatt tggaaggagt gcttggcacg gttttactct taacgcgaac      60
gaggacgaag tcgtagtgg gcagggccca agagggccg ttttgaagca catttgtcgc     120
cgtattaatg tgtatccctc catttccttc ttacattctc aaacgatttc tcccgcactt     180
tgctcatcga gaacatggc aaggaagctg aaagtaggcc agctccgaga cgaactcgcc     240
cagcgtgggc ttgacacaat cgggaccaag cccttactgg tgctgagact ggaggatgct     300
ttgctcaagg agaggaagaa agaagaggaa aatggaggca aggctaataa tgcaatcgga     360
aataacaaga gaaaagagg gagggaatcg gatgtctgta ataacgagga ttcggacaaa     420
gtcaatgccg ttgaggagtt tgacaaaatg aatgtcaagc aattacgcga acaagctact     480
cttcgacgtc tttccactgt tggcaccaaa aaggaacttc tcgagaggct tgtgaagat      540 gccgacaaga atcctcttcc tgttaaagaa gaagaagaag aagaggaaga agaagaagaa     600
gaagagaagg aaagtagcaa ggaggagaaa atcgttacgg ccacaaagaa aggggtggct     660
```

| | |
|---|---|
| gttctggatc aagggatccc agatgacata aaggctcatt atcatggtga tgatatctat | 720 |
| gatgccatgt taaatcagac gaatgttggg caaaacaata acaaattctt tgtgatccag | 780 |
| cttctagaat ctgatgactc gaagacatac atggttcata acagatgggg tagagttggt | 840 |
| gtgaagggtc aaattaagtt acatggcccc tttacttcac gacaagccgc aattgatgag | 900 |
| tttcaaacca aattctttaa caagaccaaa aactattggt acaacagaaa agactttgtt | 960 |
| tgtcacccaa agtgctacac cttgctggag atggactatg atgaaaaaga aaggaatct | 1020 |
| gatgtcaaaa gaaaggctaa ctcttccatt ggtgctcaat tgcgggagac aaagcttgaa | 1080 |
| caacgtgttg ctaagtttat ctctattata tgcaatatca gcatgatgaa gcaacaaatg | 1140 |
| atggaaatag gatacaatgc tgacaagttg cctcttggta agctaagcaa atccacaatt | 1200 |
| ttaaaggggt atgatgtctt aaagaaaatt gctgatgtga ttgaccagtc aaacaggagc | 1260 |
| aagcttgagc aattaagttc ggaatttttac accgtgattc cacatgattt tggatttaga | 1320 |
| aaaatgcgtg agtcttcttc ttcatctcct cctctaacca tacccaataa caatattaca | 1380 |
| actgacacag aactatatgt ggcaggtgat tttgtcatcg acacacctca gaagttgaaa | 1440 |
| aagaagttgg aaatggttga agccctggga gaaatagagg tcgcatcaaa attattaatg | 1500 |
| gatgacatta cgatggagga agatccttta tattatcggt accaacagct tcactgtgaa | 1560 |
| ctgtttcctc ttgacaatga tactgaggag ttcgctatga ttgtaaagta tattcagaat | 1620 |
| actcatgctc agacacattc aaattataca gttgatgttg ttcaaatatt cgcggtgaga | 1680 |
| agagacggtg aaagtgaacg ctttaaaaag ttttctggaa caaaaaatag aatgctgttg | 1740 |
| tggcatggtt ctcggcttac taactggact ggcattctgt cccaaggttt gcgcattgct | 1800 |
| ccacctgaag cgcctgccac gggttacatg tttgggaagg gggtttactt tgctgatatg | 1860 |
| ttctccaaaa gtgcaaatta ttgctatact aattctgcct tcacgactgg ggtgttgctt | 1920 |
| ctatgtgagg tagttcttca atcagttcaa atgatatttt tggttgccct gggagacatg | 1980 |
| gctgagcttc tacaagctaa aagcgatgct gataagctgc cggatgggaa gttgagcaca | 2040 |
| aagggtgttg gtgcaactgc actggatccc tctgaagccc agtcacttga tgatggtgtt | 2100 |
| gtagttcccc taggaaaacc aaaggagcaa aaacggaagg gtgctttatt atacaatgaa | 2160 |
| tatgtagtct acaatgtcga ccagataagg atgcgctact tgattcaagt tagtttcaaa | 2220 |
| tatacaaagt ag | 2232 |

<210> SEQ ID NO 24
<211> LENGTH: 2157
<212> TYPE: DNA
<213> ORGANISM: Gossypium hirsutum

<400> SEQUENCE: 24

| | |
|---|---|
| atggcaagta agctgaaagc aggccagctc cgagacgaac tcgcccagcg tgggcttgac | 60 |
| acaatcggga ccaagcccct tactggtgct gagactggag atgctttgct caaggagagg | 120 |
| aagaaagaag aggaaaatgg aggcaaggct aacaatgcaa tcggaaataa caagagaaaa | 180 |
| agagggaggg agtcggatgt ctgtagtaac gaggattcgg acaaagtcaa tgccgttgag | 240 |
| gagtttcgac aaatgaatgt caagcaatta cgcgaacaag ctactcttcg aggcctttcc | 300 |
| actgttggca ccaaaaagga acttctcgag cggctttgtg aagatgccga caagaatcct | 360 |
| cttcctgtta agtagaagag aagaagaa gaagaagaag aagaagaaga agaagaagag | 420 |
| aaggaaagta ggaaggagga gaaatcgtt acgccacaa agaaagggt ggctgttctg | 480 |
| gatcaaggga tcccagatga gataaaggct cattatcatg ttctacaaaa ggctagtctt | 540 |

```
tgttgtttga attccatttt tgagcctgtc attttgaaaa atattttgcc tgcctgcttt      600
attctttgtt acaatataca tttacagaac agaagaatta atattttaag ttctgtgatt      660
cagggtgatc atatctatga tgccatgtta aatcagacga atgttgggca aaacaataac      720
aagttctttg tgatccagct tctagaatct gatgactcaa agacatacat ggttcataat      780
agatggggta gagttggtgt gaagggtcaa attaagttac atggccccctt tacttcacga     840 caagctgcaa ttgatgtgtt tcaaaccaag ttctttaaca agaccaaaaa ctattggtac      900
aacagaaaag actttgtttg tcacccaaag tgctacacct tgctggagat ggactatgat      960 gaaaagaaa aggattctga tgtcaaaaga aaggctaact cttccattgg tgctcaattg      1020
cgggagacaa agcttgaaca acgtgttgct aagtttatct ctgttatatg caatatcagc     1080
atgatgaagc aacaaatgat ggaaatagga tacaatgctg acaagttgcc tcttggtaag     1140
ctaagcaaat ccacaatttt aaaggggtat gatatcttaa agaaaattgc tgatgtgatt     1200
gaccagtcaa acaggagcaa gcttgagcaa ttaagttcgg aattttacac cgtgattcca     1260
catgattttg gatttagaaa aatgcgtgag tcttcttctt catctcctcc tctaaccata    1320
cccaataaca atattacaac tgacgcagaa ctatatgtgg caggtgattt tgtcatcgac     1380
aaacctcaga agttgaaaaa gaagttggaa atggttgaag ccctgggaga aatagaggtc     1440
gcatcaaaat tattaatgga tgacattacg atggaggaag atcctttata ttatcggtac     1500
cagcagcttc actgtgaact gtttcctctt gacaatgata ctgaggagtt cgctttgatt    1560
gtaaagtata ttcagaatac tcatgctcag acacattcaa attatacagt tgatgttgtt    1620
caaatattca aggtgacaag agacggtgaa agtgaacgct taaaaagtt ttctggaaca     1680 aaaaatagaa tgctgttgtg gcatggttct cggcttacta actggactgg cattctgtcc    1740
caaggtttgc gcattgctcc acctgaagcg cctgccacgg ttatatgtt tgggaagggg    1800 gtttactttg ctgatatgtt ctccaaaagt gcaaattatt gctatactaa ttctgccttc    1860
acaactgggg tgttgcttct atgtgaggtt gccctgggtg acatggctga gcttctacaa    1920
gctaaaagcg atgctgataa gctgccggat gggaagttga gcacaaaagg tgttggtgca    1980
actgcaccgg atccttctga agcccagtca cttgatgatg gtgttgtagt tccctagga    2040 aaaccgaagg agcaaaaccg gaagggtgct ttattataca atgaatatat agtctacaat   2100
gtcgaccaga taaggatgcg ctacttgatt caagttagtt tcaaatatac aaagtag      2157
```

<210> SEQ ID NO 25
<211> LENGTH: 8
<212> TYPE: PRT
<213> ORGANISM: Artificial Sequence
<220> FEATURE:
<223> OTHER INFORMATION: parp signature

<400> SEQUENCE: 25

Thr Gly Tyr Met Phe Gly Lys Gly
1               5

<210> SEQ ID NO 26
<211> LENGTH: 457
<212> TYPE: PRT
<213> ORGANISM: Artificial Sequence
<220> FEATURE:
<223> OTHER INFORMATION: Variant cotton parp2 fragment

<400> SEQUENCE: 26

Tyr Ser Asp Glu Glu Gly Val Ala Val Leu Asp Gln Gly Ile Pro Asp
1               5                   10                  15

-continued

```
Asp Ile Lys Ala His Tyr His Val Leu Gln Lys Gly Asp Ile Tyr
             20                  25                  30

Asp Ala Met Leu Asn Gln Thr Asn Val Gly Gln Asn Asn Lys Phe
             35                  40                  45

Phe Val Ile Gln Leu Leu Glu Ser Asp Ser Lys Thr Tyr Met Val
 50                  55                  60

His Asn Arg Trp Gly Arg Val Gly Val Lys Gly Gln Ile Lys Leu His
 65                  70                  75                  80

Gly Pro Phe Thr Ser Arg Gln Ala Ala Ile Asp Glu Phe Gln Thr Lys
                     85                  90                  95

Phe Phe Asn Lys Thr Lys Asn Tyr Trp Tyr Asn Arg Lys Asp Phe Val
                    100                 105                 110

Cys His Pro Lys Cys Tyr Thr Leu Leu Glu Met Asp Tyr Asp Glu Lys
                    115                 120                 125

Glu Lys Glu Ser Asp Val Lys Arg Lys Ala Asn Ser Ser Ile Gly Ala
                    130                 135                 140

Gln Leu Arg Glu Thr Lys Leu Glu Gln Arg Val Ala Lys Phe Ile Ser
145                 150                 155                 160

Ile Ile Cys Asn Ile Ser Met Met Lys Gln Gln Met Met Glu Ile Gly
                    165                 170                 175

Tyr Asn Ala Asp Lys Leu Pro Leu Gly Lys Leu Ser Lys Ser Thr Ile
                    180                 185                 190

Leu Lys Gly Tyr Asp Val Leu Lys Lys Ile Ala Asp Val Ile Asp Gln
                    195                 200                 205

Ser Asn Arg Ser Lys Leu Glu Gln Leu Ser Ser Glu Phe Tyr Thr Val
                    210                 215                 220

Ile Pro His Asp Phe Gly Phe Arg Lys Met Arg Asp Phe Val Ile Asp
225                 230                 235                 240

Thr Pro Gln Lys Leu Lys Lys Leu Glu Met Val Glu Ala Leu Gly
                    245                 250                 255

Glu Ile Glu Val Ala Ser Lys Leu Leu Met Asp Asp Ile Thr Met Glu
                    260                 265                 270

Glu Asp Pro Leu Tyr Tyr Arg Tyr Gln Gln Leu His Cys Glu Leu Phe
                    275                 280                 285

Pro Leu Asp Asn Asp Thr Glu Glu Phe Ala Leu Ile Val Lys Tyr Ile
                    290                 295                 300

Gln Asn Thr His Ala Gln Thr His Ser Asn Tyr Thr Val Asp Val Val
305                 310                 315                 320

Gln Ile Phe Lys Val Thr Arg Asp Gly Glu Ser Glu Arg Phe Lys Lys
                    325                 330                 335

Phe Ser Gly Thr Lys Asn Arg Met Leu Leu Trp His Gly Ser Arg Leu
                    340                 345                 350

Thr Asn Trp Thr Gly Ile Leu Ser Gln Gly Leu Arg Ile Ala Pro Pro
                    355                 360                 365

Glu Ala Pro Ala Thr Gly Tyr Met Phe Gly Lys Gly Val Tyr Phe Ala
                    370                 375                 380

Asp Met Phe Ser Lys Ser Ala Asn Tyr Cys Tyr Thr Asn Ser Ala Phe
385                 390                 395                 400

Thr Thr Gly Val Leu Leu Leu Cys Glu Val Ala Leu Gly Asp Met Ala
                    405                 410                 415

Glu Leu Leu Gln Ala Lys Ser Asp Ala Asp Lys Leu Pro Asp Gly Lys
                    420                 425                 430

Leu Ser Thr Lys Gly Val Gly Ala Thr Ala Pro Asp Pro Ser Glu Ala
                    435                 440                 445
```

```
Gln Ser Leu Asp Asp Gly Val Val Val
    450                 455
```

STRESS TOLERANT COTTON PLANTS

CROSS-REFERENCE TO RELATED APPLICATIONS

This application is a U.S. national stage application of International Application No. PCT/EP2005/011657, filed on Oct. 27, 2005, which claims the benefit of European Patent Application No. 04077984.5, filed on Oct. 29, 2004, and United States Provisional Patent Application No. 60/628,597, filed on Nov. 17, 2004, the disclosures of each of which are herein incorporated by reference in their entireties.

The following invention relates to modified cotton plants which have a higher degree than counterpart unmodified cotton plants of resistance to adverse growing conditions, particularly abiotic stress conditions such as, but not limited to, low or high temperatures, drought, high light intensities, chemical pollution, flooding, high salinity, high light intensities, high UV irradiation. Such stress tolerant cotton plants may be obtained by lowering the expression of the endogenous cotton parp2 gene(s), particularly under stress conditions, by modifying the activity of endogenous cotton parp2 gene(s), by exchanging the endogenous cotton parp2 gene for another allele of the parp2 gene which provides better stress tolerance, or by any combination thereof.

DESCRIPTION OF RELATED ART

Poly(ADP-ribose) polymerase (PARP), also known as poly(ADP-ribose) transferase (ADPRT) (EC 2.4.2.30), is a nuclear enzyme found in most eukaryotes, including vertebrates, arthropods, mollusks, slime moulds, dinoflagellates, fungi and other low eukaryotes with the exception of yeast. The enzymatic activity has also been demonstrated in a number of plants (Payne et al., 1976; Willmitzer and Wagner, 1982; Chen et al., 1994; O'Farrell, 1995).

PARP catalyzes the transfer of an ADP-ribose moiety derived from NAD+, mainly to the carboxyl group of a glutamic acid residue in the target protein, and subsequent ADP-ribose polymerization. The major target protein is PARP itself, but also histones, high mobility group chromosomal proteins, a topoisomerase, endonucleases and DNA polymerases have been shown to be subject to this modification.

The PARP protein from animals is a nuclear protein of 113-120 kDa, abundant in most cell types, which consist of three major functional domains: an amino-terminal DNA-binding domain containing two Zn-finger domains, a carboxy-terminal catalytic domain, and an internal domain which is auto-modified (de Murcia and Ménissier de Murcia, 1994; Kameshita et al., 1984; Lindahl et al., 1995). The enzymatic activity in vitro is greatly increased upon binding to single-strand breaks in DNA. The in vivo activity is induced by conditions that eventually result in DNA breaks (Alvarez-Gonzalez and Althaus, 1989; Ikejima et al., 1990). Automodification of the central domain apparently serves as a negative feedback regulation of PARP.

PARP activity in plant cells was first demonstrated by examining the incorporation of $^3$H from labeled NAD+ into the nuclei of root tip cells (Payne et al., 1976; Willmitzer and Wagner, 1982). The enzymatic activity was also partially purified from maize seedlings and found to be associated with a protein of an apparent molecular mass of 113 kDa, suggesting that the plant PARP might be similar to the enzyme from animals (Chen et al., 1994; O'Farrell, 1995).

Chen et al. (1994) have reported PARP activity in maize nuclei and associated this enzymatic activity with the presence of an approximately 114 kDa protein present in an extract of maize nuclei.

O'Farrel (1995) reported that RT-PCR-amplification on RNA isolated from maize (using degenerate primers based on the most highly conserved sequences) resulted in a 300 bp fragment, showing 60% identity at the amino acid level with the human PARP protein.

Lepiniec et al. (1995) have isolated and cloned a full length cDNA from *Arabidopsis thaliana* encoding a 72 kDa protein with high similarity to the catalytic domain of vertebrate PARP. The N-terminal domain of the protein does not reveal any sequence similarity with the corresponding domain of PARP from vertebrates but is composed of four stretches of amino acids (named A1, A2, B and C) showing similarity to the N-terminus of a number of nuclear and DNA binding proteins. The predicted secondary structure of A1 and A2 was a helix-loop-helix structure.

Mahajan and Zuo (1998) described the purification and cDNA cloning of a maize poly (ADP)-ribose polymerase. The enzyme is a single polypeptide of approximately 115 kD (980 amino acids) encoded by a 2943 bp open reading frame. The deduced amino acid sequence shows 40 to 42% identity and about 50% similarity to the known vertebrate PARP sequences. The features of the modular structure of the PARP molecule such as two zinc fingers, a putative nuclear localization signal, the automodification domain, and the NAD+-binding domain are conserved in the maize enzyme.

Babiychuk et al. (1998) described that two poly (ADP-ribose) polymerase homologues were found in plants, the classical Zn-finger-containing polymerase and the structurally non-classical PARP proteins, which lack the characteristic N-terminal Zn-finger domain.

Current nomenclature refers to the classical Zn-finger-containing polymerases as PARP1 proteins (and corresponding parp1 genes) whereas the structurally non-classical PARP proteins are currently referred to as PARP2 (and corresponding parp2 genes).

The following database entries identifying experimentally demonstrated and putative poly ADP-ribose polymerase protein sequences, parts thereof or homologous sequences, could be identified: BAD53855 (*Oryza sativa*); BAD52929 (*Oryza sativa*); XP-477671 (*Oryza sativa*); BAC84104 (*Oryza sativa*); AAT25850 (*Zea mays*); AAT25849 (*Zea mays*); NP_197639 (*Arabidopsis thaliana*); NP_850165 (*Arabidopsis thaliana*); NP 188107 (*Arabidopsis thaliana*); NP_850586 (*Arabidopsis thaliana*); BAB09119 (*Arabidopsis thaliana*); AAD20677 (*Arabidopsis thaliana*); Q11207 (*Arabidopsis thaliana*); C84719 (*Arabidopsis thaliana*); T51353 (*Arabidopsis thaliana*); T01311 (*Arabidopsis thaliana*); AAN12901 (*Arabidopsis thaliana*); AAM13882 (*Arabidopsis thaliana*); CAB80732 (*Arabidopsis thaliana*); CAA10482 (*Arabidopsis thaliana*); AAC79704 (*Zea mays*): AAC19283 (*Arabidopsis thaliana*); CAA10888 (*Zea mays*); CAA10889 (*Zea mays*); CAA88288 (*Arabidopsis thaliana*).

Amor et al. (1998) described the involvement of PARP in the oxidative stress response in plants. The authors showed that in cultured soybean cells, PARP is involved in responses to mild and severe abiotic stresses, by mediating DNA repair and programmed cell death processes, respectively.

WO99/37789 describes compositions and methods for influencing the metabolic state of plant cells. The compositions comprise poly ADP-ribose polymerase genes and portions thereof, particularly the maize poly ADP-ribose polymerase gene as well as antisense nucleotide sequences for poly ADP-ribose polymerase genes. The nucleotide sequences find use in transforming plant cells to alter the metabolic state of the transformed plants and plant cells.

WO 00/04173 describes means and methods to modulate programmed cell death (PCD) in eukaryotic cells and organism, particularly plants cells and plants, by introduction of PCD modulating chimeric genes influencing the expression and/or apparent activity of endogenous poly-ADP-ribose polymerase (PARP) genes. Programmed cell death may be inhibited or provoked. The invention particularly relates to the use of nucleotide sequences encoding proteins with PARP activity for modulating PCD, for enhancing growth rate or for producing stress tolerant cells and organisms.

The prior art thus remains deficient in the provision of specific cotton PARP genes useful in the modification of cotton endogenous PARP genes to obtain stress resistant cotton plants.

SUMMARY OF THE INVENTION

In one aspect of the invention, a method to produce a stress tolerant cotton plant comprising the steps of introducing a chimeric gene into a cotton cell, to generate a transgenic cotton cell, the chimeric gene comprising operably linked a plant expressible promoter; a transcribable DNA region comprising a first DNA region comprising a nucleotide sequence of at least 19 out of 20 consecutive nucleotides selected from the nucleotide sequence of a parp2 gene or parp2 cDNA from a cotton species or from a species related to a cotton progenitor species; a second DNA region comprising a nucleotide sequence of at least 19 or 50 or 200 consecutive nucleotides selected from the first DNA region; whereby the first DNA region and the second DNA region are in inverted repeat orientation with regard to each other and wherein an RNA molecule transcribed from the transcribable region is capable of forming a double stranded RNA region between an RNA region transcribed from the first DNA region and an RNA region transcribed from the second DNA region; and a DNA region comprising a transcription termination and polyadenylation signal functional in plants; regenerating the transgenic cotton cell to obtain a transgenic cotton plant; and identifying a transgenic cotton plant which is more resistant to abiotic stress conditions than an untransformed cotton plant, e.g. using a fiber tissue culture assay, using a cold germination assay, by determination of the concentration of any one of reactive oxygen species, NAD or ATP or by any other stress tolerance assay. The nucleotide sequence of the parp2 gene or parp2 cDNA may comprises the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.:18, SEQ ID No.19 or SEQ ID No. 20 or a nucleotide sequence encoding a protein comprising the amino acid sequence of SEQ ID No.: 13, SEQ ID No.:21 or SEQ ID No.:22 or a variant thereof.

It is another object of the invention to provide a method to produce a stress tolerant cotton plant comprising the steps of providing one or more double stranded RNA molecules to cells of the cotton plants, wherein the double stranded RNA molecules comprise two RNA strands, one RNA strand consisting essentially of an RNA nucleotide sequence of 20 to 21 consecutive nucleotides selected from the nucleotide sequence of a parp2 gene or parp2 cDNA from a cotton species or from a species related to a cotton progenitor species; and identifying a cotton plant comprising the double stranded RNA molecule or molecules which is more resistant to abiotic stress conditions than a same cotton plant which does not comprise the double stranded RNA molecule or molecules. The double stranded RNA may be provided to the cells by integrating a chimeric gene into the genome of a cell, the chimeric gene comprising a DNA region comprising at least 20 consecutive nucleotides selected from the nucleotide sequence of a parp2 gene or parp2 cDNA from a cotton species or from a species related to a cotton progenitor species in antisense or sense orientation; operably linked to a plant expressible promoter and a DNA region comprising a transcription termination and polyadenylation signal functional in plants. The nucleotide sequence of the parp2 gene or parp2 cDNA may comprises the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.: 18, SEQ ID No.:19 or SEQ ID No.:20 or a nucleotide sequence encoding a protein comprising the amino acid sequence of SEQ ID No.: 13, SEQ ID No.: 21 or SEQ ID No.:22 or a variant thereof.

It is yet another object of the invention to provide a method to identify cotton parp2 DNA fragments comprising the steps of providing genomic DNA or cDNA obtainable from a cotton species, such as *Gossypium hirsutum, Gossypium barbadense, Gossypium arboreum*, or *Gossypium herbaceum* or from a cotton species related to a cotton progenitor species such as *Gossypium raimondii, Gossypium trilobum* and *Gossypium gossypioides*; selecting a means from the following group: a DNA fragment comprising a nucleotide sequence encoding the amino acid sequence of SEQ ID No.: 13 for use as a probe; a DNA fragment comprising the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.: 18, SEQ ID No.:19 or SEQ ID No 20 for use as a probe; a DNA fragment or oligonucleotide comprising a nucleotide sequence consisting of between 20 to 1382 consecutive nucleotides selected from a nucleotide sequence encoding the amino acid sequence of SEQ ID No.: 13, SEQ ID No.:21 or SEQ ID No.:22 for use as a probe; a DNA fragment or oligonucleotide comprising a nucleotide sequence consisting of between 20 to 1382 consecutive nucleotides selected from a nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.: 18, SEQ ID No.: 19 or SEQ ID No.: 20 for use as a probe; an oligonucleotide sequence having a nucleotide sequence comprising between 20 to 200 consecutive nucleotides selected from a nucleotide sequence encoding the amino acid sequence of SEQ ID No.: 13, SEQ ID No. 21 or SEQ ID No.: 22; an oligonucleotide sequence having a nucleotide sequence comprising between 20 to 200 consecutive nucleotides selected from the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.: 18, SEQ ID No.: 19 or SEQ ID No.:20 for use as a primer in a PCR reaction; or an oligonucleotide having the nucleotide sequence of any one of SEQ ID No.: 1, SEQ ID No.: 2,SEQ ID No.: 3 or SEQ ID No.: 4, SEQ ID No.: 16 or SEQ ID No.17 for use as a primer in a PCR reaction; and utilizing that means to identify the fragment by performing a PCR using the genomic or the cDNA and the primers or by performing hybridization using the genomic or the cDNA and the probes. The identified fragment may subsequently be isolated and used to obtain stress tolerant cotton cells.

The invention also provides a method to identify cotton parp2 alleles correlated with increased stress tolerance comprising the steps of providing a population, optionally a mutagenized population, of different cotton plants lines or plant lines related to cotton progenitor plants; identifying in each plant line of the population a parp2 allele according to the method of claim 21; analyzing the stress resistance of each plant line of the population and identifying those cotton plant lines; and correlating the increased stress resistance in a plant line to the presence of a specific parp2 allele. The cotton parp2 allele may be introduced into a cotton plant line of choice to obtain stress tolerant plants.

Also provided is a method to identify a stress resistant cotton plant comprising the following steps: initiate a fiber tissue culture from the cotton plant; subject the fiber tissue culture to a stress condition, such as increased temperature, preferably in the range of 45 to 50° C., for a selected period of time, preferably in the range of 2 to 4 hours; and compare fiber initiation or elongation in the culture to fiber initiation or elongation in a culture initiated from a control plant and subject to the stresses conditions.

It is yet another object of the invention to provide an isolated DNA fragment encoding a protein comprising the amino acid sequence of SEQ ID No.: 13, SEQ ID No.: 20, SEQ ID No.:21 or SEQ ID No.: 15, or comprising the nucleotide sequence selected from the group of any one of the nucleotide sequences of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.: 18, SEQ ID No.: 19 or SEQ ID No.:20.

The invention further provides a chimeric gene comprising the following operably linked DNA fragments: a plant expressible promoter; a transcribable DNA region comprising a first DNA region comprising at least 20 consecutive nucleotides selected from the nucleotide sequence of a parp2 gene or parp2 cDNA from a cotton species or from a species related to a cotton progenitor species in sense orientation and a second DNA region comprising at least 20 consecutive nucleotides selected from the nucleotide sequence of a parp2 gene or parp2 cDNA from a cotton species or from a species related to a cotton progenitor species in sense orientation, whereby an RNA molecule produced by transcription of the transcribed DNA region is capable of forming a double stranded RNA region by base-pairing between an RNA region corresponding to the first DNA region and an RNA region corresponding to the second RNA region; and a DNA region comprising a transcription termination and polyadenylation signal functional in plants. The chimeric gene may also comprise a plant expressible promoter; a DNA region comprising at least 20 consecutive nucleotides selected from the nucleotide sequence of a parp2 gene or parp2 cDNA from a cotton species or from a species related to a cotton progenitor species in sense or antisense orientation; and a DNA region comprising a transcription termination and polyadenylation signal functional in plants.

Cotton plant cell comprising such chimeric genes and cotton plants consisting essentially of such cotton plant cells, as well as seed thereof are also provided by the invention.

The invention also relates to the use of a nucleotide sequence encoding a protein comprising the amino acid sequence of SEQ ID No.: 13, SEQ ID No. 21, SEQ ID No.: 22 or SEQ ID No.: 15 or a part thereof comprising at least 20 consecutive nucleotides, or to the use of a nucleotide sequence of any one of SEQ ID No.: 5, SEQ ID No.: 6, SEQ ID No.: 7, SEQ ID No.: 8, No.: 9, SEQ ID No.: 10, SEQ ID No.: 11, SEQ ID No.: 12, SEQ: 18, SEQ ID No.: 19 or SEQ ID No.: 20 ID or a part thereof comprising at least 20 consecutive nucleotides to increase the stress tolerance of a cotton plant; to identify a parp2 gene or parp2 cDNA in a cotton species, such as *Gossypium hirsutum, Gossypium barbadense, Gossypium arboreum*, or *Gossypium herbaceum* or from a cotton species related to a cotton progenitor species such as *Gossypium raimondii, Gossypium trilobum* and *Gossypium gossypioides*; to identify a stress tolerant parp2 allele in a cotton species, such as *Gossypium hirsutum, Gossypium barbadense, Gossypium arboreum*, or *Gossypium herbaceum* or from a cotton species related to a cotton progenitor species such as *Gossypium raimondii, Gossypium trilobum* and *Gossypium gossypioides* or to introduce a stress tolerant parp2 allele in a cotton species.

With the foregoing and other objects, advantages and features of the invention that will become hereinafter apparent, the nature of the invention may be more clearly understood by reference to the following detailed description of different embodiments of the invention, the appended claims and the figures.

BRIEF DESCRIPTION OF THE FIGURES

FIG. 4 is an alignment of the various amino acid sequences obtained for parp2 from cotton. GV1: amino acid sequence (SEQ ID NO. 21) encoded by genomic DNA variant one (SEQ ID NO. 19); cDNA: amino acid sequence (SEQ ID NO. 13) encoded by the cDNA of SEQ ID NO. 12; GV2: amino acid sequence (SEQ ID NO 22) encoded by genomic DNA variant two (SEQ ID NO. 20).

DETAILED DESCRIPTION OF DIFFERENT EMBODIMENTS OF THE INVENTION

Figure 1:
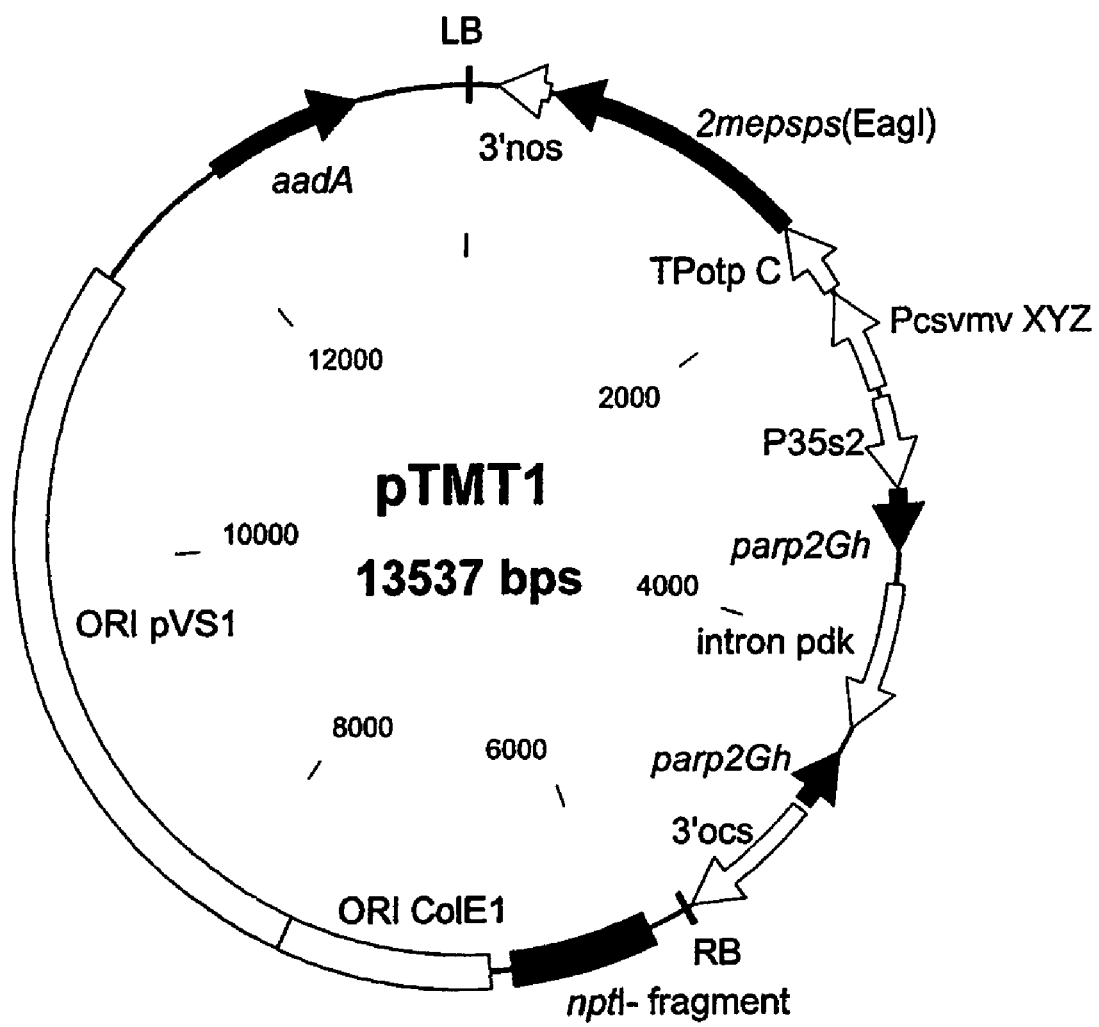
FIG. 1 is a schematic representation of pTMT1, a T-DNA vector comprising a chimeric gene which upon transcription yields a double stranded RNA molecule capable of reducing the expression of cotton PARP2 genes. The following abbreviations are used: LB: left T-DNA border; 3'nos: transcription termination and polyadenylation signal from the nopaline synthase gene of *A. tumefaciens* T-DNA; 2mepsps: double mutant 5-enol-pyruvylshikimate-3-phosphate synthase protein from corn; TPotpC: transit peptide; PcsvmvX, Y, Z: first, second and third part of Cassava vein mosaic virus promoter; P35S2: Cauliflower mosaic virus 35S promoter; parp2Gh: part of the cotton parp2 nucleotide sequence; Pdk-intron: Intron 2 from the pdk-intron of *Flaveria trinervia*; OCS-terminator: transcription termination and polyadenylation signal from the octopine synthase gene of *A. tumefaciens* T-DNA; RB: right T-DNA border; NPTI-fragment: portion of the nptI antibiotic resistance gene; ORI ColE1: origin of replication of ColE1 plasmid; ORI pVS1: origin of replication of pVS1 replicon.
Figure 2:
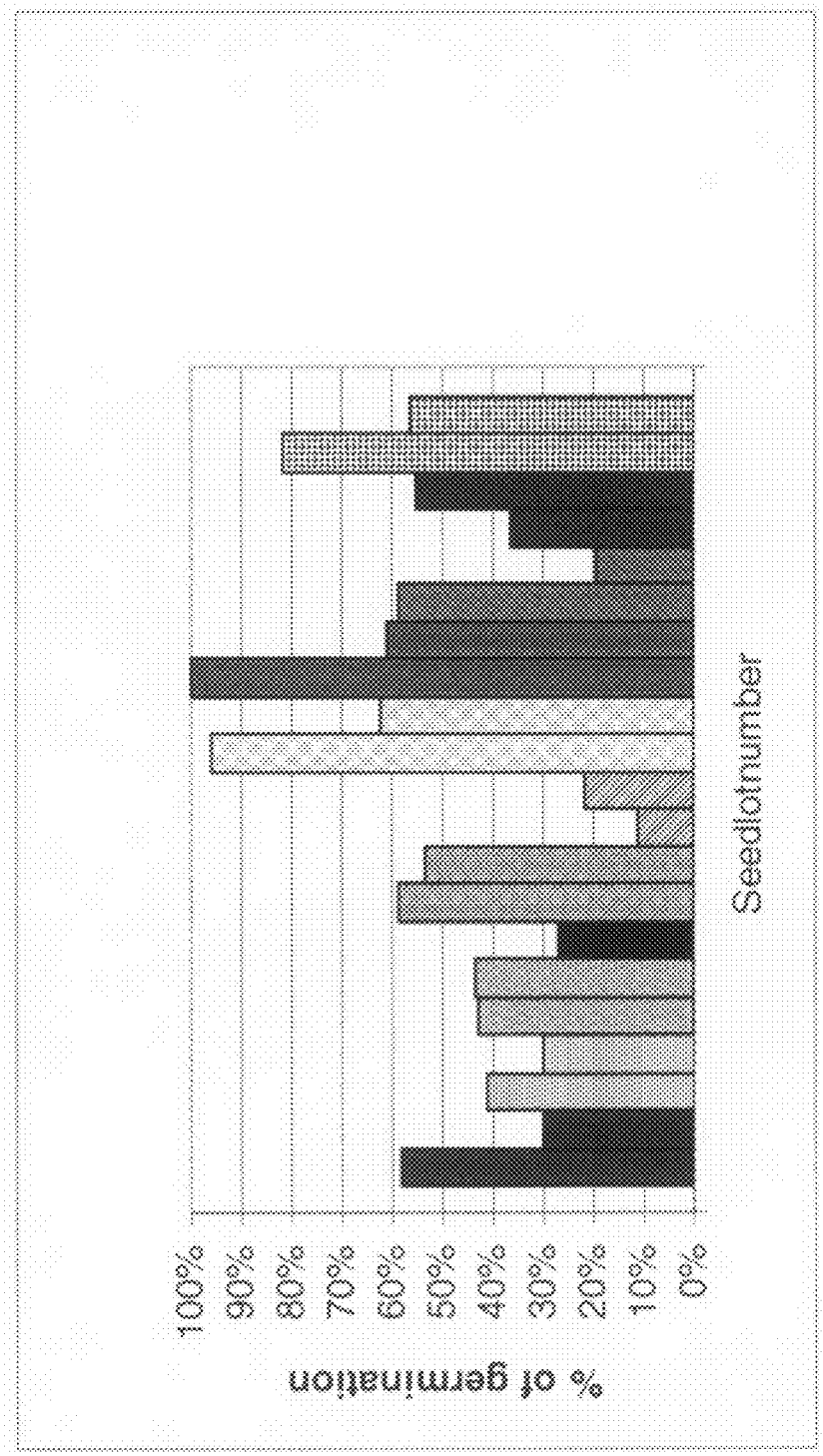
FIG. 2: Graphical representation of the cold germination assay. For each transgenic event (indicated by the number on the X-axis and by the pattern) the percentage of seedlings germinating at 16° C. are indicated for the homozygous (H) and azygous (h) segregated populations.

The current invention is based on the finding that cotton parp2 genes or cotton parp2 cDNAs are excellent source nucleotide sequences to obtain stress tolerant cotton plants by modifying the activity of endogenous cotton parp2 gene(s), by exchanging the endogenous cotton parp2 gene for another allele of the parp2 gene which provides better stress tolerance, or by any combination thereof.

In one embodiment, the invention is related to a method for obtaining a stress tolerant cotton plant by reducing the expression of the endogenous parp2 gene in cells of a cotton plant, by producing a transgenic plant comprising a chimeric gene capable of producing a double stranded RNA ("dsRNA") molecule wherein the complementary RNA strands of such a dsRNA molecule comprises a part of the nucleotide sequence of a parp2 gene or a parp2 cDNA obtained from a cotton species of from a species related to a cotton progenitor species or a part of a nucleotide sequence encoding a PARP2 protein from a cotton species or cotton progenitor-related species.

"Cotton," as used herein, includes the allotetraploid species *Gossypium hirsutum*, *Gossypium barbadense* (AD-genome allopolyploids) and the diploid species *Gossypium arboreum* and *Gossypium* herbaceum (A-genome diploids). *Gossypium* species related to the cotton progenitors are *Gossypium raimondii*, *Gossypium trilobum* and *Gossypium gossypioides* (D-genome diploids).

A parp2 gene or a parp2 cDNA obtained from a cotton species or from a species related to a cotton progenitor species refers to the parp2 gene that naturally occurs in that species or to cDNA corresponding to the mRNA of the parp2 gene that naturally occurs in that species. Similarly, a PARP2 protein obtained from a cotton species or from cotton progenitor-related species refers to the protein as it naturally occurs in that species.

Examples of such parp2 cotton or cotton progenitor-related nucleotide sequences include those comprising the nucleotide sequence set forth in any one of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.: 19 or SEQ ID No.: 20. Other examples of such parp2 cotton sequences include the nucleotide sequences encoding a cotton PARP2 gene comprising e.g. the amino acid sequence of SEQ ID No.: 13 or of SEQ ID No.: 21 or of SEQ ID No.:22.

However, it will be immediately clear to the person skilled in the art that the exemplified nucleotide sequences or parts thereof can be used to identify further parp2 genes or parp2 cDNAs in other cotton plants, in cotton varieties other than Coker312 or in cotton-progenitor related plants, and that such nucleotide sequences or parts thereof may also be used e.g. to increase the stress tolerance in cotton plants. The exemplified nucleotide sequences could be used to select:

i) a DNA fragment comprising a nucleotide sequence encoding the amino acid sequence of SEQ ID No.: 13 for use as a probe;

ii) a DNA fragment comprising the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.: 19 or SEQ ID No.: 20 for use as a probe;

iii) a DNA fragment or oligonucleotide comprising a nucleotide sequence consisting of between 20 to 1382 consecutive nucleotides selected from a nucleotide sequence encoding the amino acid sequence of SEQ ID No.: 13 for use as a probe;

iv) a DNA fragment or oligonucleotide comprising a nucleotide sequence consisting of between 20 to 2000 consecutive nucleotides selected from a nucleotide sequence encoding the amino acid sequence of SEQ ID Nos: 21 or 22 for use as a probe v) a DNA fragment or oligonucleotide comprising a nucleotide sequence consisting of between 20 to 2000 consecutive nucleotides selected from a nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.: 19 or SEQ ID No.: 20 for use as a probe;

vi) an oligonucleotide sequence having a nucleotide sequence comprising between 20 to 200 consecutive nucleotides selected from a nucleotide sequence encoding the amino acid sequence of SEQ ID No.: 13 for use as a primer in a PCR reaction;

vii) an oligonucleotide sequence having a nucleotide sequence comprising between 20 to 200 consecutive nucleotides selected from a nucleotide sequence encoding the amino acid sequence of SEQ ID Nos: 21 or 22 for use as a primer in a PCR reaction;

viii) an oligonucleotide sequence having a nucleotide sequence comprising between 20 to 200 consecutive nucleotides selected from the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.: 19 or SEQ ID No.: 20 for use as a primer in a PCR reaction; or ix) an oligonucleotide having the nucleotide sequence of any one of SEQ ID No.: 1, SEQ ID No.: 2, SEQ ID No.: 3, SEQ ID No.: 4, SEQ ID No.: 16 or SEQ ID No.: 17 for use as a primer in a PCR reaction.

x) a fragment which can be amplified from cotton genomic or cDNA using as primers an oligonucleotide as described in vi, vii, viii or ix, such as a fragment comprising the nucleotide sequence of SEQ ID No.: 18 for use as a probe.

By performing a PCR using genomic or cDNA from cotton species, varieties or cotto-progenitor related plants and the mentioned oligonucleotides as primers or by performing hybridization, preferably under stringent conditions between genomic or cDNA from cotton species, varieties or cotton-progenitor related plants and the mentioned probes, such other parp2 genes or cDNA or fragments thereof can be identified and/or isolated. It will be clear that for the purposes of obtaining stress tolerant cotton plants, it may not be required to identify the actual nucleotide sequence of the isolated DNA fragment. However, optionally, the nucleotide sequence of the identified and/or isolated DNA fragments or the amino acid sequence of the potential coding frames can be aligned against the available nucleotide or amino acid sequences. The presence of the so-called PARP signature (TGYMFGKG) (SEQ ID No. 25) or a nucleotide sequence encoding such a DNA sequence in the thus obtained sequence can also be verified. The enzymatic activity (polyadenylribosylation) can be assayed as described in WO 00/04173.

"Stringent hybridization conditions" as used herein means that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5× Denhardt's solution, 10% dextran sulfate, and 20 µg/ml denatured, sheared carrier DNA such as salmon sperm DNA, followed by washing the hybridization support in 0.1×SSC at approximately 65° C., e.g. for about 10 min (twice). Other hybridization and wash conditions are well known and are exemplified in Sambrook et al, Molecular Cloning: A Laboratory Manual, Second Edition, Cold Spring Harbor, N.Y. (1989), particularly chapter 11.

Using the exemplified parp2 nucleotide sequences or the PARP2 amino acid sequences, variant sequences can also be made by insertion, deletion or substitution of nucleotides or amino acids. Variant PARP2 cotton proteins can be described as those proteins which comprise an amino acid sequence based upon the amino acid sequence of any one of SEQ ID Nos.: 13, 21 or 22 wherein one, two, three, four, five or more of the amino acids in variant positions are replaced by functionally similar amino acid sequences. The following groups of interchangeable amino acids can be distinguished:

aliphatic amino acids (Glycine (G), Alanine (A), Valine (V) Leu (L) and Isoleucine (I))

aromatic amino acids (Phenylalanine (F), tyrosine (Y), Tryptophane (W))

aliphatic hydroxyl containing amino acids (Serine (S), Threonine (T))

basic amino acids (Lysine (K), Arginine (R), Histidine (H))

acidic amino acids (Aspartic acid (D), Glutamic acid (E))

amide containing amino acids (Asparagine (N), Glutamine (Q))

Conserved amino acid residues are considered to be the following: the amino acids at position 372-380, 15, 35, 63, 82, 113, 115, 117, 123, 163, 167, 168, 172, 173, 183, 189, 226, 234, 242, 251, 266, 271, 275, 285, 289, 344, 367, 368, 371, 386, 394, 408, 415, 429, 443 and 445 of SEQ ID No.: 15. All other amino acids positions may be considered variant positions. Thus, variant PARP2 proteins may include the amino acid sequence of SEQ ID No.: 15.

Other variant proteins are those which contain at least the following amino acids from SEQ ID 13, which are the amino acids conserved between the parp2 encoded protein from mouse, corn, rice *Arabidopsis* and cotton: the amino acids of position 9, 11, 14, 22, 31-32, 35-36, 40-43, 47-50, 55, 57, 58, 60, 67, 70-75, 78-79, 82, 91, 96, 99, 100, 103, 104, 106, 108, 111, 114, 121, 124, 126, 127, 128, 154, 157, 165, 166, 167, 171, 175, 177, 180, 186, 187, 189, 195, 198, 199, 202, 203, 205, 209, 217, 223, 224, 225, 226, 228, 229, 230, 231, 232, 233, 242, 244, 248, 251, 256, 257, 258, 259, 261, 262, 264, 266, 267, 278, 279, 281, 286, 292, 299, 306, 310, 311, 314, 315, 318, 319, 326, 333, 337, 345-352, 353-355, 357, 358, 360, 361-363, 365, 366, 367, 369, 370, 371, 372-374, 376-383, 385-389, 391-397, 406, 408-410, 412-416, 420-422, 431, 434-435, 439, 440, 442, 446, 457 and 460. These variant proteins may either have in the other positions amino acids selected from the alternatives provided in SEQ ID No.: 15 or they may even have other amino acids at those variant positions.

The part of the nucleotide sequence of the parp2 gene or parp2 cDNA which is comprised within one strand of the double stranded RNA molecule should be at least 19 nucleotides long, but may vary from about 19 nucleotides (nt) up to a length equaling the length (in nucleotides) of the parp2 cDNA or gene. The total length of the sense or antisense nucleotide sequence may thus be at least at least 25 nt, or at least about 50 nt, or at least about 100 nt, or at least about 150 nt, or at least about 200 nt, or at least about 500 nt. It is expected that there is no upper limit to the total length of the sense or the antisense nucleotide sequence. However for practical reason (such as e.g. stability of the chimeric genes) it is expected that the length of the sense or antisense nucleotide sequence should not exceed 5000 nt, particularly should not exceed 2500 nt and could be limited to about 1000 nt.

It will be appreciated that the longer the total length of the part of the parp2 or parp2 cDNA (sense or antisense region) the less stringent the requirements for sequence identity between these regions and the corresponding sequence in the endogenous parp2 gene its complement. Preferably, the nucleic acid of interest should have a sequence identity of at least about 75% with the corresponding target sequence, particularly at least about 80%, more particularly at least about 85%, quite particularly about 90%, especially about 95%, more especially about 100%, quite especially be identical to the corresponding part of the target sequence or its complement. However, it is preferred that the nucleic acid of interest always includes a sequence of about 19 consecutive nucleotides, particularly about 25 nt, more particularly about 50 nt, especially about 100 nt, quite especially about 150 nt with 100% sequence identity to the corresponding part of the target nucleic acid. Preferably, for calculating the sequence identity and designing the corresponding sense or antisense sequence, the number of gaps should be minimized, particularly for the shorter sense sequences.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madision, Wis., USA) using the default scoring matrix with a gap creation penalty of 50 and a gap extension penalty of 3.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

It has been demonstrated that the minimum requirement for silencing a particular target gene is the presence in the silencing chimeric gene nucleotide sequence of a nucleotide sequence of about 20-21 consecutive nucleotides long corresponding to the target gene sequence, in which at least 19 of the 20-21 consecutive nucleotides are identical to the corresponding target gene sequence. "19 out of 20 consecutive nucleotides" as used herein refers to a nucleotide sequence of 20 consecutive nucleotides selected from the target gene having one mismatch nucleotide. As used herein "a stress tolerant cotton plant" or "a cotton plant tolerant to stress conditions or adverse growing conditions" is a plant (particularly a cotton plant obtained according to the methods of the invention), which, when subjected to adverse growing conditions for a period of time, such as but not limited to drought, high temperatures, limited supply of nutrients (particularly nitrogen), high light intensities, grows better than a control plant not treated according to the methods of the invention. This will usually be apparent from the general appearance of the plants and may be measured e.g., by increased biomass production, continued vegetative growth under adverse conditions or higher seed yield. Stress tolerant plants have a broader growth spectrum, i.e. they are able to withstand a broader range of climatological and other abiotic changes, without yield penalty. Biochemically, stress tolerance may be apparent as the higher $NAD^+$-NADH/ATP content and lower production of reactive oxygen species of stress tolerant plants compared to control plants under stress condition. Stress tolerance may also be apparent as the higher chlorophyll content, higher photosynthesis and lower chlorophyll fluorescence under stress conditions in stress tolerant plants compared to control plants under the same conditions. Stress tolerant cotton plants may also be recognized by analyzing the impact of stress conditions on fiber initiation and/or elongation under stress conditions, including increased temperature, in fiber tissue cultures.

It will be clear that it is also not required that the plant be grown continuously under the adverse conditions for the stress tolerance to become apparent. Usually, the difference in stress tolerance between a plant or plant cell according to the invention and a control plant or plant cell will become apparent even when only a relatively short period of adverse conditions is encountered during growth.

dsRNA encoding cotton parp2 expression reducing chimeric genes according to the invention may comprise an intron, such as a heterologous intron, located e.g. in the spacer sequence between the sense and antisense RNA regions in accordance with the disclosure of WO 99/53050 (incorporated herein by reference).

It has recently become apparent that double stranded RNA molecules, such as the ones described above, are cleaved in plant cells into small RNA fragments of about 20-21 nucleotides, which serve as guide sequence in the degeneration of the corresponding mRNA (reviewed by Baulcombe, 2004). Thus, in another embodiment, the invention is drawn to a method for producing a stress tolerant cotton plant comprising the steps of:
  a) providing one or more double stranded RNA molecules to cells of the cotton plants, wherein the double stranded RNA molecules comprise two RNA strands, one RNA strand consisting essentially of an RNA nucleotide sequence of 20 to 21 consecutive nucleotides selected from the nucleotide sequence of a parp2 gene or parp2 cDNA from a cotton species or from a species related to a cotton progenitor species; and
  b) identifying a cotton plant comprising these double stranded RNA molecule or molecules which is more resistant to abiotic stress conditions than a same cotton plant which does not comprise the double stranded RNA molecule or molecules.

The mentioned 20-21 nt long dsRNA sequences are also generated in the course of conventional antisense RNA mediated silencing or sense RNA mediated silencing. Thus, in another embodiment of the invention, a method is provided for producing stress tolerant cotton plants, comprising the step of providing to cells of the cotton plant a chimeric gene comprising, operably linked, the following DNA fragments
  a) a plant expressible promoter;
  b) a DNA region comprising at least 20 consecutive nucleotides selected from the nucleotide sequence of a parp2 gene or parp2 cDNA from a cotton species or from a species related to a cotton progenitor species in antisense or in sense orientation;
  c) a DNA region comprising a transcription termination and polyadenylation signal functional in plants.

The mentioned antisense or sense nucleotide regions may thus be about from about 21 nt to about 5000 nt long, such as 21 nt, 40 nt, 50 nt, 100 nt, 200 nt, 300 nt, 500 nt, 1000 nt, or even about 2000 nt or larger in length. Moreover, it is not required for the purpose of the invention that the nucleotide sequence of the used inhibitory parp2 gene molecule or the encoding region of the chimeric gene, is completely identical or complementary to the endogenous cotton parp2 gene the expression of which is targeted to be reduced in the cotton plant cell. The longer the sequence, the less stringent the requirement for the overall sequence identity is. Thus, the sense or antisense regions may have an overall sequence identity of about 40% or 50% or 60% or 70% or 80% or 90% or 100% to the nucleotide sequence of the endogenous parp2 gene or the complement thereof. However, as mentioned, antisense or sense regions should preferably comprise a nucleotide sequence of 19-20 consecutive nucleotides having about 100% sequence identity to the nucleotide sequence of the parp2 gene. Preferably the stretch of about 100% sequence identity should be about 50, 75 or 100 nt.

The efficiency of the above mentioned chimeric genes for antisense RNA or sense RNA mediated gene silencing may be further enhanced by inclusion of DNA elements which result in the expression of aberrant, unpolyadenylated parp2 inhibitory RNA molecules. One such DNA element suitable for that purpose is a DNA region encoding a self-splicing ribozyme, as described in WO 00/01133. The efficiency may also be enhanced by providing the generated RNA molecules with nuclear localization or retention signals as described in WO 03/076619.

The exemplified cotton parp2 cDNA nucleotide sequences can also be used to identify cotton parp2 alleles in a population of cotton plants or cotton progenitor plants which are correlated with increased stress tolerance. The population of cotton plant may be a population which has been previously mutagenized. The identified cotton parp2 alleles may than be introduced into a cotton plant line of choice using conventional breeding techniques.

Methods to transform cotton plants are also well known in the art. Agrobacterium-mediated transformation of cotton has been described e.g. in U.S. Pat. No. 5,004,863 or in U.S. Pat. No. 6,483,013 and cotton transformation by particle bombardment is reported e.g. in WO 92/15675.

The described methods and means may be used in cotton plants, such as Coker 312, Coker310, Coker SAcala SJ-5, GSC25110, FIBERMAX varieties such as FIBERMAX 819, Siokra 1-3, T25, GSA75, Acala SJ2, Acala SJ4, Acala SJ5, Acala SJ-C1, Acala B1644, Acala B1654-26, Acala B1654-43, Acala B3991, Acala GC356, Acala GC510, Acala GAM1, Acala Cl, Acala Royale, Acala Maxxa, Acala Prema, Acala B638, Acala B1810, Acala B2724, Acala B4894, Acala B5002, non Acala "picker" Siokra, "stripper" variety FC2017, Coker 315, STONEVILLE 506, STONEVILLE 825, DP50, DP61, DP90, DP77, DES119, McN235, HBX87, HBX191, HBX107, FC 3027, CHEMBRED A1, CHEMBRED A2, CHEMBRED A3, CHEMBRED A4, CHEMBRED Bi, CHEMBRED B2, CHEMBRED B3, CHEMBRED Cl, CHEMBRED C2, CHEMBRED C3, CHEMBRED C4, PAYMASTER 145, HS26, HS46, SICALA, PIMA S6 and ORO BLANCO PIMA and plants with genotypes derived thereof.

The obtained transformed cotton plant according to the invention, or the obtained stress tolerant cotton plants wherein the endogenous parp2 gene has been replaced by a stress tolerant parp2 allele can be used in a conventional breeding scheme to produce more plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

It will further be clear to the person skilled in the art that a parp2 cDNA or a parp2 genomic DNA, or a part thereof as herein described can also be used for enhancing the growth rate of any plant or to increase the stress tolerance in cells of any plant in accordance with the teaching of WO 00/04173.

Furthermore, it is known that introduction of antisense, sense or doublestranded RNA or the encoding chimeric genes may lead to a distribution of phenotypes, ranging from almost no or very little suppresion of the expression of the target gene to a very strong or even a 100% suppression of the expression of the target gene. However, a person skilled in the art will be able to select those plant cells, plants, events or plant lines leading to the desired degree of silencing and desired phenotype.

It will also be clear to the person skilled in the art that parp2 genes or cDNAs isolated from different varieties, or parts thereof, may differ in nucleotide sequence or in the amino acid of the encoded polypeptide, yet be significant similar or even identical in particular regions. In other words, the different variants of parp2 genes can share similar or identical stretches of contiguous 20-200 nucleotide sequences. Therefore, whenever the specification or the claims refer to a DNA region comprising at least x consecutive nucleotides from a particular nucleotide sequence, or from a nucleotide sequence encoding a particular amino acid sequence, it will be clear that what is referred to are the at least x consecutive nucleotides as such without reference to the origin of the nucleotide sequence.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region, which is functionally or structurally defined, may comprise additional DNA regions etc.

The following non-limiting Examples describe chimeric genes for the alteration of stress tolerance characteristics in cotton and uses thereof. Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK.

Throughout the description and Examples, reference is made to the following sequences represented in the sequence listing:

SEQ ID No 1: nucleotide sequence of the oligonucleotide P1a suitable to amplify a part of cotton parp2 gene or cDNA.

SEQ ID No 2: nucleotide sequence of the oligonucleotide P1b suitable to amplify a part of cotton parp2 gene or cDNA.

SEQ ID No 3: nucleotide sequence of the oligonucleotide P1c suitable to amplify a part of cotton parp2 gene or cDNA.

SEQ ID No 4: nucleotide sequence of the oligonucleotide P1x suitable to amplify a part of cotton parp2 gene or cDNA.

SEQ ID No 5: partial cDNA sequence of cotton parp2 gene (containing PARP signature) variant 1.

SEQ ID No 6: partial cDNA sequence of cotton parp2 gene (containing PARP signature) variant 2.

SEQ ID No 7: partial cDNA sequence of cotton parp2 gene (containing PARP signature) variant 3.

SEQ ID No 8: partial cDNA sequence of cotton parp2 gene (part 2) variant 1.

SEQ ID No 9: partial cDNA sequence of cotton parp2 gene (part 2) variant 2.

SEQ ID No 10: partial cDNA sequence of cotton parp2 gene (part 2) variant 3.

SEQ ID No 11: partial cDNA sequence of cotton parp2 gene (part 2) variant 4.

SEQ ID No 12: partial nucleotide sequence of cotton parp2 cDNA (fused).

SEQ ID No 13: partial amino acid sequence of cotton PARP2 protein.

SEQ ID No 14: nucleotide sequence of T-DNA region of vector pTMT01.

SEQ ID No 15: variants of the partial amino acid sequence of cotton PARP2 protein.

SEQ ID No 16: oligonucleotide primer 1 used for the preparation of a cotton parp2 specific probe.

SEQ ID No 17: oligonucleotide primer 2 used for the preparation of a cotton parp2 specific probe.

SEQ ID No 18: nucleotide sequence of a cotton parp2 specific probe.

SEQ ID No 19: nucleotide sequence of genomic DNA comprising a cotton parp2 gene variant 1.

SEQ ID No 20: nucleotide sequence of genomic DNA comprising a cotton parp2 gene variant 2.

SEQ ID No 21: amino acid sequence of the protein structure which can be encoded by SEQ ID No 19.

SEQ ID No 22: amino acid sequence of the protein structure which can be encoded by SEQ ID No 20.

SEQ ID No 23: cDNA copy of the mRNA of cotton parp2 gene variant 1

SEQ ID No 24: cDNA copy of the mRNA of cotton parp2 gene variant 2

EXAMPLES

Example 1

Isolation of cDNA Sequences for Cotton Parp2

Oligonucleotide sequences to be used as degenerate primers in a PCR amplification of part of cotton parp2 gene were designed by comparison of the available nucleotide sequences for parp2 genes from *Arabidopsis thaliana, Zea mays* and *Oryza sativa*. Primers were designed using regions of highest homology in exons. In this way the following degenerated primers were generated:

```
                                            (SEQ ID No.: 1)
    P1a:  5'-GGTyGCCAAGkGGAACAACAACACC-3'

(SEQ ID No.: 2)
    P1b:  5'-GGATGATCCdTTrTATkmTCrmTACmAGC-3'

(SEQ ID No.: 3)
    P1c:  5'-GAGAArATbGTwAChGCsACrArGAArGG-3'
```

RNA was extracted from cotton callus (Coker 312) based on the protocol described by Jones et al. (1985) and used for cDNA synthesis using SuperScript™ First-strand synthesis System for RT-PCR (Invitrogen Life Technologies) according to the manufacturer's instructions.

Using the cDNA as template, and primer pair P1a/P1b PCR amplification was performed under the following conditions:

|  | |
|---|---|
|  | 5 min at 95° C. |
| Annealing | 35 sec at 52° C. |
| Elongation | 35 sec at 72° C. |
| Denaturation | 1 min at 92° C. |
|  | for 50 cycles |
|  | followed by 40 sec at 52° C. and 10 min at 72° C. |

A DNA fragment of about 580 bp was amplified, cloned and several clones were sequenced (comprising the sequences of SEQ ID 5, 6 and 7). All of the predicted amino acid sequences encoded by the variant sequences contained the so-called PARP signature (TGYMFGKG) (SEQ ID No. 25) which is conserved in all PARP proteins.

On the basis of the amplified sequences, a new (non-degenerated) primer was designed which would allow amplification of the upstream part of the parp2 cDNA:

```
                                           (SEQ ID No.: 4)
P1x:  5'-CAAGAGGAAACAGTTCACAGTGAAGC-3'.
```

Using cDNA and PCR conditions as described above, with the exception that only 35 cycles were performed, and oligonucleotides P1x and P1c as primers, a DNA fragment of about 600 bp was amplified, which overlapped with the previously amplified part of the parp2 cDNA, and constituted the part of the cDNA of parp2 upstream of the previously amplified fragment. Again, variant sequences were identified (SEQ ID Nos 8-11).

SEQ ID No. 12 represents the nucleotide sequence of the fused parp2 gene parts. SEQ ID No. 13 includes the amino acid sequence of the encoded protein PARP2 by the nucleotide sequence of SEQ ID No. 12.

Southern hybridizations were performed with genomic DNA of A-genome diploid cotton plants, and AD tetraploid plants. Two bands of which only one was present in the A-genome diploids, could be observed using several restriction enzyme digestions.

Example 2

Construction of a T-DNA Vector containing a PARP2 Silencing Gene

An amplified DNA fragment comprising the PARP signature as described in Example 1 was used to construct a chimeric gene which upon transcription yields an RNA molecule comprising a sense and antisense DNA sequence from the amplified DNA fragment, and which could basepair to form a double stranded RNA molecule. Such a chimeric gene can be used to reduce the expression of parp2 in cotton. To this end the following DNA fragments were operably linked using standard recombinant DNA techniques:

- a fragment including the promoter region of the Cauliflower Mosaic Virus 35S transcript (Odell et al., 1985) (SEQ ID No.: 14 from nucleotide 2686 to nucleotide 3191)
- fragment including a C-terminal part including the PARP signature of the coding sequence of the *Gossypium hirsutum* (cotton) non classical-type poly(ADP-ribose) polymerase parp2 cDNA cloned in sense orientation (SEQ ID No.:14 from nucleotide 3192 to nucleotide 3617).
- fragment containing the second intron of the pyruvate orthophosphate dikinase gene from *Flaveria trinervia* as described by Rosche and Westhoff (1995) (SEQ ID No.: 14 from nucleotide 3649 to nucleotide 4423).
- fragment including a C-terminal part including the PARP signature of the coding sequence of the *Gossypium hirsutum* (cotton) non classical-type poly(ADP-ribose) polymerase parp2 cDNA cloned in antisense orientation (SEQ ID No.: 14 from nucleotide 4424 to nucleotide 4851).
- fragment including the 3' untranslated region of the octopine synthase gene of *Agrobacterium tumefaciens* as described by De Greve et al. (1982) (SEQ ID No.: 14 from nucleotide 4852 to nucleotide 5591).

This chimeric gene was introduced between the T-DNA borders of a T-DNA vector together with a chimeric gene encoding a selectable marker to yield pTMT1 (see FIG. 1; sequence of the T-DNA of pTMT1 is represented in SEQ ID No.: 14). The vector pTMT1 is derived from pGSC1700 (Cornelissen and Vandewiele, 1989). The vector backbone contains the following genetic elements:

- the plasmid core comprising the origin of replication from the plasmid pBR322 (Bolivar et al., 1977) for replication in *Escherichia coli* (ORI ColE1) and a restriction fragment comprising the origin of replication from the *Pseudomonas* plasmid pVS1 (Itoh et al., 1984) for replication in *Agrobacterium tumefaciens* (OR1 pVS1).
- a selectable marker gene conferring resistance to streptomycin and spectinomycin (aadA) for propagation and selection of the plasmid in *Escherichia coli* and *Agrobacterium tumefaciens*.
- a DNA region consisting of a fragment of the neomycin phosphotransferase coding sequence of the nptI gene from transposon Tn903 (Oka et al., 1981).

The T-DNA vector was introduced into *Agrobacterium tumefaciens* comprising a helper Ti-plasmid. Cotton plants were transformed using the obtained *A. tumefaciens* strain, according to the protocol as described in U.S. Pat. No. 6,483, 013.

Example 3

Analysis of Transgenic Cotton Plants Harboring a PARP2 Silencing Gene

Different transgenic cotton lines, comprising the chimeric gene as described in Example 1 were obtained. Transgenic plant lines were analyzed on molecular level using Southern blot analysis. Similarly, the plant lines are analyzed for parp2 RNA expression using Northern blot and for presence of PARP2 protein using e.g. ELISA or Western blotting. An indication of PARP activity can be obtained using e.g. the TUNEL assay which visualizes single stranded DNA breaks.

Transgenic plant lines of T0 generation were backcrossed with Coker 312 plants, to reduce potential somaclonal variation in the resulting transformed plant lines.

The segregating populations of selfed transgenic cotton lines were analysed for the presence of the transgene in homozygous, or heterozygous form, or the absence of the transgene using real-time PCR.

The different plant lines are subjected to various forms of stresses. Either homologous populations of transgenic plants are compared to untransformed reference plants, or segregating populations are used, followed by determination of the homozygous, heterozygous and azygous plant lines using standard techniques.

A first assay is the "cold germination assay" whereby seeds are germinated on sandy soil at a temperature of 5° C. Similar test may also be used as described by Schulze et al., 1996, Schulze et al., 1996, Duesterhaus et al., 1999 or Duesterhaus et al., 2000

A further assay is to subject the growing plants to various periods of drought or increased temperature (or a combination thereof) followed by a period of growth under standard greenhouse conditions for cotton, prior to the visual scoring of the plants.

As it is also known that cotton fiber initiation and/or elongation is subject to various stress conditions, including e.g. cold, an assay is developed whereby the influence of decreased temperature or increased temperature on fiber tissue cultures initiated from the different transgenic plant lines is analyzed. To this end, fiber tissue cultures are initiated, essentially as described by Beasly and Ting, 1974. The cultures are then subjected to a period of modified temperature (e.g. 2 hrs-4 hrs at 45-50° C.), and the effect on the fiber initiation is recorded.

A further assay is the fitness assay essentially as described in WO02/066972 (incorporated herein by reference) whereby the stress conditions imposed upon the explant material as described therein, can be replaced or supplemented by additional stress conditions such as cultivation under decreased or increased temperature.

The transgenic plant lines are also analyzed to determine the level of reactive oxygen species in plants or explants, under stress conditions compared to the level of reactive oxygen species in similar plant material under normal conditions, essentially as described in European patent application EP04077624.7 (incorporated herein by reference). Similarly, the transgenic plant lines are also analyzed to determine the level of ATP and/or NAD(H) in plants or explants, under stress conditions compared to the level of ATP and/or NAD (H) in similar plant material under normal conditions, essentially as described in EP04077624.7.

The different transgenic plant lines are also used in field trials, whereby irrigated plots are compared to non-irrigated plots. The plants are visually scored for agronomical fitness and damage, as compared to azygous plants as well as reference cotton plants.

Several transgenic plant lines are observed that contain an increased tolerance to adverse growing conditions or to the imposed stress conditions in one or more of the above described assays.

Example 4

Field Trials with Transgenic Cotton Lines

Different homozygous transgenic cotton lines, as well as corresponding null lines, identified as described in Example 3, were used in field trials comparing plots which received full-time irrigation were compared with plots which were only irrigated in the beginning of the growth season, thereby subjecting the cotton plants to significant heat stress. A hail storm destroyed part of the field, making interpretation of the results difficult. Nevertheless, it appeared that a few transgenic lines looked healthier and had more vegetative growth, i.e. appeared more vigorous.

Example 5

Analysis of Transgenic Cotton Lines Using a Cold Germination Assay

Transgenic cotton lines were selfed and the segregating progeny population was analyzed as described in Example 3 for progeny plants which were either homozygous or which were azygous. 50 seeds from either homozygous plants or from azygous plants for each event were sown in sand. The trays were incubated at a constant temperature of 16° C. for 21 days, when germinated seedlings were counted. Germination of cotton seeds is sensitive to temperatures lower than 18° C. At the same time 50 seeds from the same seedlots as mentioned above were grown on sand but incubated at 26° C. during the day and 21° C. at night for 12 days. The number of emerging seedlings was counted and used to correct the data for the cold germination test for any effect of seed lot quality.

FIG. 4 represents data for 11 different events comparing the homozygous lines with azygous lines. Particularly the homozygous transgenic lines indicated as line 7, 9 and 11 performed very well as almost no loss of germination during the stress could be observed.

Example 6

Analysis of Transgenic Cotton Lines for Tolerance to of Paraquat Treatment

Figure 3A:
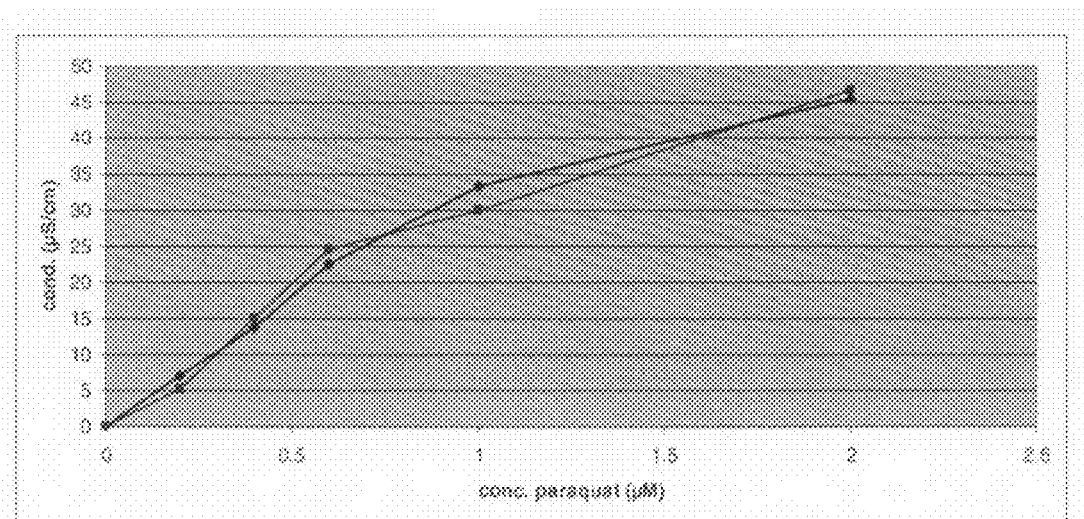
FIG. 3: Graphical representation of the conductivity of the medium after incubation in the presence of different concentrations of paraquat for control cotton plants (♦) or for transgenic cotton lines comprising a parp2 silencing construct (■) for three different transgenic lines each represented in panel 3A, 3B, 3C.
Figure 3B:
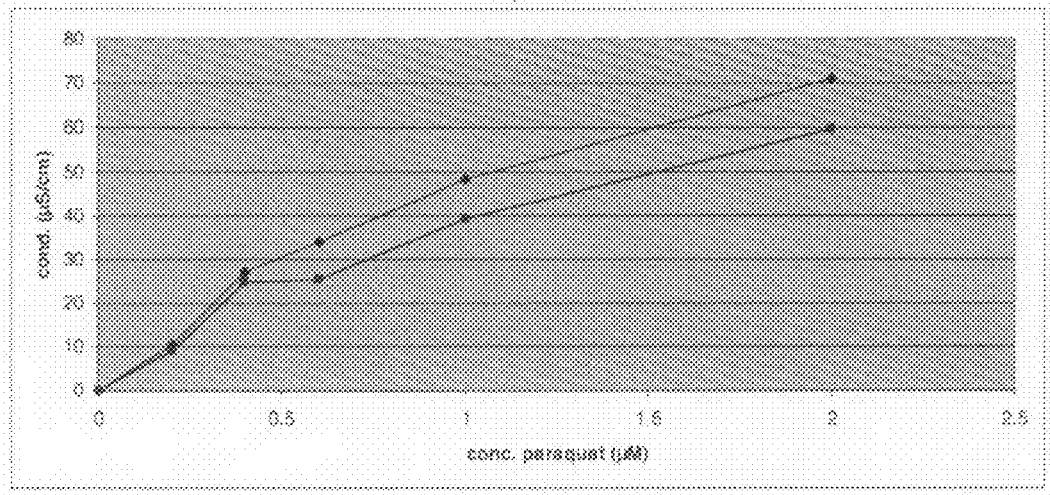
Figure 3C:
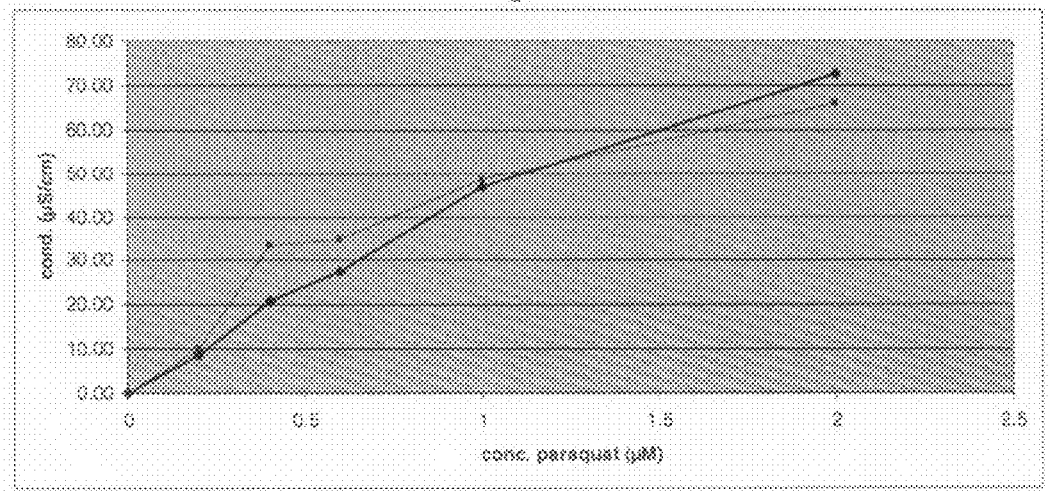

Leaves from the three transgenic cotton lines identified in Example 5 as performing well in the cold germination assay were subjected to a paraquat tolerance assay, in comparison with leaves from non-transgenic Coker312. To this end, leaf discs of about 1 square cm were incubated in different petri dishes containing solution of paraquat at different concentrations (6 repeats per concentration). The petri dishes were incubated in the dark for 4 hours, followed by a 2 hours incubation under high light intensity. Thereafter, plates were incubated in the dark overnight. Paraquat damage to the cell membranes was estimated the next day by measuring the conductivity of the incubation medium. The results of these measurements are summarized in FIG. 3. As can be seen from that FIG. 3B, at least one transgenic line showed more tolerance to paraquat treatment than the control line.

Example 7

Isolation of Genomic Clones Encoding Cotton parp2

Cotton parp2 genomic clones were isolated using standard recombinant techniques from a *Gossypium hirsutum* BAC library. Briefly, a commercially available BAC library from *Gossypium hirsutum* cultivar Maxxa was screened using a probe obtained by PCR amplification using cotton cDNA as template and oligonucleotides having the sequence of SEQ ID No. 16 and SEQ ID No. 17 as primers. The sequence of the oligonucleotides was derived from the cDNA sequence of SEQ ID No.: 12. The sequence of the amplified DNA fragment, which represents a cotton parp2 specific cDNA based probe, is provided as SEQ ID No.: 18. 12 BAC clones were identified as putative positive candidates. Analysis of the restriction fragment pattern of these clones revealed two types of clones. Genomic variant 1 was the most abundant representative in the library. A representative of each clone was subjected to nucleotide sequence determination by primer walking. The nucleotide sequence for the relevant part of both clones is provided as SEQ ID No. 19 and SEQ ID No. 20 respectively. The amino acid sequences of the polypeptides which can be encoded by these nucleotide sequences are provided as SEQ ID No. 21 and SEQ ID No. 22, respectively. The nucleotide sequence of the mRNAs after transcription and splicing is provided as SEQ ID No. 23 and SEQ ID No. 24. The polypeptides which can be encoded by the two variants of the genomic clones (from cv Maxxa; SEQ ID Nos. 20 and 21) were aligned and compared with the polypeptide by the cDNA clone (from Coker312; SEQ ID No. 13) as illustrated in FIG. 4.

As expected the three polypeptides share significant sequence identity or sequence homology.

The main difference between the polypeptides encoded by the genomic clones and the (incomplete) polypeptide encoded by the cDNA clone is the presence of an additional 26 amino acids stretch in the polypeptides encoded by the genomic clones (both variants) (SEQ ID No.: 21 from AA 444 to AA 469).

GV1 polypeptide moreover has an N-terminal extension (SEQ ID No 21 from AA 1 to AA 65) while it lacks a stretch of 48 amino acids present in GV2 (SEQ ID No 22 from AA 174 to AA 221). A similar stretch of amino acids (except the 4 AA; VLQK) are also absent from the polypeptide encoded by the cDNA clone. In addition the GV1 polypeptide has an insertion of about 11 amino acids in its C-terminal part (SEQ ID No 21 from AA 644 to AA 664)

Preferred target regions to include into the silencing constructs according to the invention may therefore be the nucleotide sequences encoding a polypeptide having the amino acid sequence of SEQ ID No.: 13 from 7 to 26; SEQ ID No.: 13 from 31 to 238; SEQ ID No.: 13 from 239 to 412; SEQ ID No.: 13 from 413 to 423; SEQ No.: ID 13 from 425 to 460.

REFERENCES

Alvarez-Gonzalez and Althaus (1989) *Mut. Res.* 218, 67-74
Amor et al. (1998) *FEBS Letters* 440, 1-7
Babiychuk et al (1997) *Proc. Natl. Acad. Sci. USA*, 94, 12722-12727
Baulcombe (2004) *Nature* 431, 356-363
Bolivar, F et al. (1977). *Gene* 2, 95-113
Chen et al. (1994) *Eur. J. Biochem* 224, 135-142
Cornelissen, M., Vandewiele, M. (1989). *Nucleic Acids Research*, 17, 19-25.
De Greve et al. (1982). *J. Mol. Appl. Genetics*, 1 (6), 499-511.
de Murcia and Ménissier de Murcia (1994) *Trends Biochem. Sci.* 19, 172-176.
Duesterhaus et al. (1999) *Proceedings of the Beltwide Cotton Conference* 1: 621-623
Duesterhaus et al. (2000) *Proceedings of the Beltwide Cotton Conference* 1: 596-599
Ikajima et al. (1990) *J. Biol. Chem.* 265, 21907-21913
Itoh et al. (1984). *Plasmid,* 11, 206
Jones et al. (1985) *EMBO J.* 4, 2411-2418
Kameshita et al. (1984) *J. Biol. Chem.* 259, 4770-4776
Lebrun et al. (1996). U.S. Pat. No. 5,510,471
Lebrun et al. (2003) U.S. Pat. No. 6,566,587B1
Lepiniec et al. (1995) *FEBS Letters* 364, 103-108
Lindahl et al. (1995) *Trends Biochem. Sci.* 20, 405-411
Mahajan and Zuo (1998) *Plant Physiology* 118, 895-905
Needleman and Wunsch (1970) *J. Mol. Biol.* 48: 443-453
O'Farrel (1995) *Biochimie* 77, 486-491
Odell et al. (1985) *Nature* 313, 810
Oka et al. (1981). *Journal of Molecular Biology,* 147, 217-226
Payne et al. (1976) *Exp. Cell Res.* 99, 428-432
Rosche, E., Westhoff, P. (1995). *Plant Molecular Biology,* 29 (4), 663-678
Schulze et al. (1996) *Proceedings of the Beltwide Cotton Conference* 2: 1240-1243
Schulze et al. (1997) *Proceedings of the Beltwide Cotton Conference* 1: 1383-1385
Verdaguer et al. (1998). *Plant Mol Biol,* 37, 1055-1067
Willmitzer and Wagner (1982) In *ADP-Ribosylation Reactions* (Hayashi, O. and Ueda, K., eds). New York: Academic Press, pp. 241-252
Zambryski (1988). *Ann. Rev. Genet.* 22: 1-30

What is claimed is:

1. A method of producing a cotton plant which has a higher yield under adverse growing conditions comprising the steps of
   a) introducing a chimeric gene into a cotton cell, to generate a transgenic cotton cell, said chimeric gene comprising the following operably linked DNA fragments:
      i) a plant expressible promoter;
      ii) a transcribable DNA region comprising;
         (1) a first DNA region comprising a nucleotide sequence of at least 100 consecutive nucleotides selected from the nucleotide sequence of a parp2 gene or of a parp2, cDNA wherein said nucleotide sequence of said parp2 gene or parp2 cDNA comprises the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11 or SEQ ID No.: 12 or comprises a nucleotide sequence encoding a protein comprising the amino acid sequence of SEQ ID No.: 13;
         (2) a second DNA region comprising a nucleotide sequence of at least 100 consecutive nucleotides selected from said first DNA region; whereby said first DNA region and said second DNA region are in inverted repeat orientation with each other and wherein an RNA molecule transcribed from said transcribable region is capable of forming a double stranded RNA region between an RNA region transcribed from said first DNA region and an RNA region transcribed from said second DNA region; and
      iii) a DNA region comprising a transcription termination and polyadenylation signal functional in plants;
   b) regenerating said transgenic cotton cell to obtain a transgenic cotton plant; and
   c) identifying a transgenic cotton plant which has a higher yield under adverse growing conditions than an untransformed cotton plant under said adverse growing conditions,
   wherein said adverse growing conditions are drought, high temperatures, limited supply of nutrients or high light intensities.

2. The method according to claim 1, wherein said first and said second DNA region comprise at least 200 consecutive nucleotides.

3. The method according to claim 1, wherein said transgenic cotton plant which has a higher yield under adverse growing conditions than an untransformed cotton plant under said adverse growing conditions is identified using a fiber tissue culture assay.

4. The method according to claim 1, wherein said transgenic cotton plant which has a higher yield under adverse growing conditions than an untransformed cotton plant under said adverse growing conditions is identified using a cold germination assay.

5. The method according to claim 1, wherein said transgenic cotton plant which has a higher yield under adverse growing conditions than an untransformed cotton plant under said adverse growing conditions is identified by determination of the concentration of any one of reactive oxygen species, NAD or ATP.

6. A method to produce a cotton plant which has a higher yield under adverse growing conditions comprising the steps of:
   a) providing one or more double stranded RNA molecules to cells of cotton plants, wherein said double stranded RNA molecules comprise two RNA strands, one RNA strand consisting essentially of an RNA nucleotide sequence of at least 100 consecutive nucleotides selected from the nucleotide sequence of a parp2 gene or of a parp2 cDNA wherein said nucleotide sequence of said parp2 gene or parp2 cDNA comprises the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11 or SEQ ID No.: 12 or comprises a nucleotide sequence encoding a protein comprising the amino acid sequence of SEQ ID No.: 13; and
   b) identifying a cotton plant comprising said double stranded RNA molecule or molecules which has a higher yield under adverse growing conditions than a same cotton plant which does not comprise said double stranded RNA molecule or molecules under said adverse growing conditions,
   wherein said adverse growing conditions are drought, high temperatures, limited supply of nutrients or high light intensities.

7. The method according to claim 6, wherein said double stranded RNA is provided to said cells by integrating a chimeric gene into the genome of a said cell, said chimeric gene comprising the following operably linked DNA fragments:
   a) a plant expressible promoter;
   b) a transcribable DNA region comprising;
      i) a first DNA region comprising at least 100 consecutive nucleotides selected from the nucleotide sequence of said parp2 gene or of said parp2 cDNA in sense orientation;
      ii) a second DNA region comprising at least 100 consecutive nucleotides selected from the nucleotide sequence of said parp2 gene or of said parp2 cDNA in antisense orientation,
      whereby an RNA molecule produced by transcription of said transcribed DNA region is capable of forming a double stranded RNA region by base-pairing between an RNA region corresponding to said first DNA region and an RNA region corresponding to said second DNA region; and
   c) a DNA region comprising a transcription termination and polyadenylation signal functional in plants.

8. A method of identifying parp2 DNA fragments from *Gossypium hirsutum, Gossypium barbadense, Gossypium arboreum, Gossypium herbaceum, Gossypium raimondii, Gossypium trilobum* or *Gossypium gossypioides* comprising the steps of:
   a) providing genomic DNA or cDNA obtainable from *Gossypium hirsutum, Gossypium barbadense, Gossypium*

*arboreum, Gossypium herbaceum, Gossypium raimondii, Gossypium trilobum* or *Gossypium gossypioides*, and b) identifying said fragment by performing hybridization under stringent hybridization conditions using said genomic DNA or said cDNA and a probe, wherein said probe is
i) a DNA fragment comprising a nucleotide sequence encoding the amino acid sequence of SEQ ID No.: 13;
ii) a DNA fragment comprising the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11, SEQ ID No.: 12, SEQ ID No.: 19 or SEQ ID No.: 20; or
iii) a fragment comprising the nucleotide sequence of SEQ ID No.: 18 for use as a probe;
wherein stringent hybridization conditions include overnight incubation in a solution comprising 50% formamide, 5× standard sodium citrate buffer (SSC), 50 mM sodium phosphate, 5× Denhardt's solution, 10% dextran sulfate and 20μg/ml denatured sheared carrier DNA, followed by washing twice the hybridization support in 0.1×SSC at approximately 65° C. for about 10 minutes.

9. A method of isolating a cotton parp2 DNA fragment comprising the steps of:
a) identifying said cotton parp2 fragment according to the method of claim 8; and
b) isolating said cotton parp2 fragment.

10. An isolated DNA fragment encoding a protein comprising the amino acid sequence of SEQ ID No.: 13.

11. An isolated DNA fragment encoding a protein comprising the amino acid sequence of SEQ ID No.: 21 or SEQ ID No.: 22.

12. An isolated DNA fragment comprising the nucleotide sequence of any one of the nucleotide sequences of SEQ ID No.: 5, SEQ ID No.: 6, SEQ ID No.: 7, SEQ ID No.: 8, SEQ ID No.: 9, SEQ ID No.: 10, SEQ ID No.: 11, or SEQ ID No.: 12.

13. An isolated DNA fragment comprising the nucleotide sequence of SEQ ID No.: 19 or SEQ ID No.: 20.

14. A chimeric gene comprising the following operably linked DNA fragments:
a) a plant expressible promoter;
b) a transcribable DNA region comprising;
i) a first DNA region comprising at least 100 consecutive nucleotides selected from the nucleotide sequence of a parp2 gene or of a parp2 cDNA, wherein said nucleotide sequence of said parp2 gene or parp2 cDNA comprises the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11 or SEQ ID No.: 12 or comprises a nucleotide sequence encoding a protein comprising the amino acid sequence of SEQ ID No.: 13 in sense orientation;
ii) a second DNA region comprising at least 100 consecutive nucleotides selected from the nucleotide sequence of a parp2 gene or of a parp2 cDNA wherein said nucleotide sequence of said parp2 gene or parp2 cDNA comprises the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11 or SEQ ID No.: 12 or comprises a nucleotide sequence encoding the amino acid sequence of SEQ ID No.: 13 in antisense orientation,
whereby an RNA molecule produced by transcription of said transcribed DNA region is capable of forming a double stranded RNA region by base-pairing between an RNA region corresponding to said first DNA region and an RNA region corresponding to said second DNA region; and
c) a DNA region comprising a transcription termination and polyadenylation signal functional in plants.

15. A chimeric gene comprising the following operably linked DNA fragments
a) a plant expressible promoter;
b) a DNA region comprising at least 100 consecutive nucleotides selected from the nucleotide sequence of a parp2 gene or of a parp2 cDNA wherein said nucleotide sequence of said parp2 gene or parp2 cDNA comprises the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11 or SEQ ID No.: 12 or comprises a nucleotide sequence encoding a protein comprising the amino acid sequence of SEQ ID No.: 13 in sense orientation; and
c) a DNA region comprising a transcription termination and polyadenylation signal functional in plants.

16. A chimeric gene comprising the following operably linked DNA fragments
a) a plant expressible promoter;
b) a DNA region comprising at least 100 consecutive nucleotides selected from the nucleotide sequence of a parp2 gene or of a parp2 cDNA wherein said nucleotide sequence of said parp2 gene or parp2 cDNA comprises the nucleotide sequence of any one of SEQ ID No.: 5, SEQ ID No.: 6, SEQ ID No.: 7, SEQ ID No.: 8, SEQ ID No.: 9, SEQ ID No.: 10, SEQ ID No.: 11 or SEQ ID No.: 12 or comprises a nucleotide sequence encoding a protein comprising the amino acid sequence of SEQ ID No.: 13 in antisense orientation; and
c) a DNA region comprising a transcription termination and polyadenylation signal functional in plants.

17. A cotton plant cell comprising the chimeric gene of claim 14.

18. A cotton plant consisting essentially of the cotton plant cells of claim 17.

19. A seed of the cotton plant according to claim 18, wherein the seed comprises the chimeric gene.

20. The method according to claim 1, wherein said transcribable DNA region comprises the nucleotide sequence of SEQ ID No.: 14 from nucleotide 3192 to nucleotide 4851.

21. A method of producing a cotton plant which has a higher yield under adverse growing conditions comprising the steps of
a) introducing a chimeric gene into a cotton cell, to generate a transgenic cotton cell, said chimeric gene comprising the following operably linked DNA fragments:
i) a plant expressible promoter;
ii) a transcribable DNA region comprising;
(1) a first DNA region comprising a nucleotide sequence of at least 100 consecutive nucleotides selected from a nucleotide sequence encoding a protein consisting of the amino acid sequence of any one of SEQ ID No.: 21 from amino acid position 444 to amino acid position 469, SEQ ID No.: 21 from amino acid position 1 to amino acid position 65, SEQ ID No.: 22 from amino acid position 174 to 331 or SEQ ID No.: 21 from amino acid position 644 to 664;
(2) a second DNA region comprising a nucleotide sequence of at least 100 consecutive nucleotides selected from said first DNA region; whereby said first DNA region and said second DNA region are in inverted repeat orientation with each other and wherein an RNA molecule transcribed from said transcribable region is capable of forming a double stranded RNA region between an RNA region transcribed from said first DNA region and an RNA region transcribed from said second DNA region; and iii) a DNA region comprising a transcription termination and polyadenylation signal functional in plants;

b) regenerating said transgenic cotton cell to obtain a transgenic cotton plant; and c) identifying a transgenic cotton plant which has a higher yield under adverse growing conditions than an untransformed cotton plant under said adverse growing conditions, wherein said adverse growing conditions are drought, high temperatures, limited supply of nutrients or high light intensities.

22. A method to produce a cotton plant which has a higher yield under adverse growing conditions comprising the steps of:

a) providing one or more double stranded RNA molecules to cells of cotton plants, wherein said double stranded RNA molecules comprise two RNA strands, one RNA strand consisting essentially of an RNA nucleotide sequence of at least 100 consecutive nucleotides selected from a nucleotide sequence encoding a protein consisting of the amino acid sequence of any one of SEQ ID No.: 21 from amino acid position 444 to amino acid position 469, SEQ ID No.: 21 from amino acid position 1 to amino acid position 65, SEQ ID No.: 22 from amino acid position 174 to 331 or SEQ ID No.: 21 from amino acid position 644 to 664; and b) identifying a cotton plant comprising said double stranded RNA molecule or molecules which has a higher yield under adverse growing conditions than a same cotton plant which does not comprise said double stranded RNA molecule or molecules under said adverse growing conditions, wherein said adverse growing conditions are drought, high temperatures, limited supply of nutrients or high light intensities.

23. A chimeric gene comprising the following operably linked DNA fragments:

a. a plant expressible promoter;

b. a transcribable DNA region comprising;

i. a first DNA region comprising a nucleotide sequence of at least 100 consecutive nucleotides selected from a nucleotide sequence encoding a protein consisting of the amino acid sequence of any one of SEQ ID No.: 21 from amino acid position 444 to amino acid position 469, SEQ ID No.: 21 from amino acid position 1 to amino acid position 65, SEQ ID No.: 22 from amino acid position 174 to 331 or SEQ ID No.: 21 from amino acid position 644 to 664 in sense orientation;

ii. a second DNA region comprising a nucleotide sequence of at least 100 consecutive nucleotides selected from said first DNA region;

whereby said first DNA region and said second DNA region are in inverted repeat orientation with each other and wherein an RNA molecule transcribed from said transcribable region is capable of forming a double stranded RNA region between an RNA region transcribed from said first DNA region and an RNA region transcribed from said second DNA region, and c. a DNA region comprising a transcription termination and polyadenylation signal functional in plants.

24. A cotton plant cell comprising the chimeric gene of claim 23.

25. A cotton plant cell comprising the chimeric gene of claim 15.

26. A cotton plant cell comprising one or more double stranded RNA molecules, wherein said double stranded RNA molecules comprise two RNA strands, one RNA strand consisting essentially of an RNA nucleotide sequence of at least 100 consecutive nucleotides selected from a nucleotide sequence encoding a protein consisting of the amino acid sequence of any one of SEQ ID No.: 21 from amino acid position 444 to amino acid position 469, SEQ ID No.: 21 from amino acid position 1 to amino acid position 65, SEQ ID No.: 22 from amino acid position 174 to 331 or SEQ ID No.: 21 from amino acid position 644 to 664.

27. A cotton plant cell comprising one or more double stranded RNA molecules, wherein said double stranded RNA molecules comprise two RNA strands, one RNA strand consisting essentially of an RNA nucleotide sequence of at least 100 consecutive nucleotides selected from the nucleotide sequence of a parp2 gene or of a parp2 cDNA wherein said nucleotide sequence of said parp2 gene or parp2 cDNA comprises the nucleotide sequence any one of SEQ ID No.: 5, SEQ ID No.: 6, SEQ ID No.: 7, SEQ ID No.: 8, SEQ ID No.: 9, SEQ ID No.: 10, SEQ ID No.: 11 or SEQ ID No.: 12 or comprises a nucleotide sequence encoding a protein comprising the amino acid sequence of SEQ ID No.: 13.

28. A cotton plant consisting essentially of the cotton plant cells of claim 24.

29. A cotton plant consisting essentially of the cotton plant cells of claim 26.

30. A cotton plant consisting essentially of the cotton plant cells of claim 27.

31. A seed of the cotton plant according to claim 28, wherein the seed comprises the chimeric gene.

32. A seed of the cotton plant according to claim 29, wherein the seed comprises the double stranded RNA molecules.

33. A seed of the cotton plant according to claim 30, wherein the seed comprises the double stranded RNA molecules.

* * * * *